US012760118B2

(12) United States Patent
Chyung et al.

(10) Patent No.: US 12,760,118 B2
(45) Date of Patent: Oct. 13, 2026

(54) METHOD FOR PREVENTING HEREDITARY ANGIOEDEMA ATTACK

(71) Applicant: Takeda Pharmaceutical Company Limited, Osaka (JP)

(72) Inventors: Yung Chyung, Lexington, MA (US); Burt Adelman, Concord, MA (US); Daniel J. Sexton, Melrose, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 184 days.

(21) Appl. No.: 17/500,214

(22) Filed: Oct. 13, 2021

(65) Prior Publication Data

US 2022/0169749 A1 Jun. 2, 2022

Related U.S. Application Data

(63) Continuation of application No. 15/562,671, filed as application No. PCT/US2016/024921 on Mar. 30, 2016, now abandoned.

(60) Provisional application No. 62/214,293, filed on Sep. 4, 2015, provisional application No. 62/140,277, filed on Mar. 30, 2015, provisional application No. 62/140,289, filed on Mar. 30, 2015.

(51) Int. Cl.
*C07K 16/40* (2006.01)
*A61P 7/10* (2006.01)
*A61K 39/00* (2006.01)

(52) U.S. Cl.
CPC ................ *C07K 16/40* (2013.01); *A61P 7/10* (2018.01); *A61K 2039/505* (2013.01); *A61K 2039/54* (2013.01); *A61K 2039/545* (2013.01); *C07K 2317/21* (2013.01); *C07K 2317/565* (2013.01); *C07K 2317/76* (2013.01); *C07K 2317/94* (2013.01)

(58) Field of Classification Search
None
See application file for complete search history.

(56) References Cited

U.S. PATENT DOCUMENTS 3,682,776 A 8/1972 Grundmann et al.
3,691,016 A 9/1972 Patel
3,969,287 A 7/1976 Jaworek et al.
4,118,481 A 10/1978 Schnabel et al.
4,153,687 A 5/1979 Schnabel et al.
4,179,337 A 12/1979 Davis et al.
4,195,128 A 3/1980 Hildebrand et al.
4,229,537 A 10/1980 Hodgins et al.
4,247,642 A 1/1981 Hirohara et al.
4,330,440 A 5/1982 Ayers et al.
4,377,572 A 3/1983 Schwarz et al.
4,399,216 A 8/1983 Axel et al.
4,595,674 A 6/1986 Tschesche et al.
4,609,725 A 9/1986 Brady et al.
4,634,665 A 1/1987 Axel et al.
4,657,893 A 4/1987 Krantz et al.
4,845,242 A 7/1989 Powers et al.
4,881,175 A 11/1989 Ladner
4,946,778 A 8/1990 Ladner et al.
4,966,852 A 10/1990 Wun et al.
5,045,452 A 9/1991 Spragg et al.
5,106,833 A 4/1992 Broze, Jr. et al.
5,118,668 A 6/1992 Auerswald et al.
5,166,133 A 11/1992 Houston et al.
5,179,017 A 1/1993 Axel et al.
5,212,091 A 5/1993 Diaz-Collier et al.
5,223,409 A 6/1993 Ladner et al.
5,260,203 A 11/1993 Ladner et al.
5,278,144 A 1/1994 Wolf
5,278,285 A 1/1994 Ebbers et al.
5,312,736 A 5/1994 Rasmussen et al.
5,372,933 A 12/1994 Zamarron et al.
5,373,090 A 12/1994 Norris et al.
5,378,614 A 1/1995 Petersen et al.
5,407,915 A 4/1995 Fritz et al.
5,409,895 A 4/1995 Morishita et al.
5,426,224 A 6/1995 Lee et al.
5,441,931 A 8/1995 Sprecher et al.
5,444,156 A 8/1995 Veloso et al.
5,446,090 A 8/1995 Harris
5,455,338 A 10/1995 Sprecher et al.
5,466,783 A 11/1995 Wun et al.
5,563,123 A 10/1996 Innis et al.
5,576,294 A 11/1996 Norris et al.
5,583,107 A 12/1996 Wolf et al.
5,585,089 A 12/1996 Queen et al.
5,589,359 A 12/1996 Innis et al.
5,618,696 A 4/1997 Norris et al.

(Continued)

FOREIGN PATENT DOCUMENTS

AT 275583 T 9/2004
BR 112015017195 A2 7/2017

(Continued)

OTHER PUBLICATIONS

Extended European Search Report mailed Oct. 29, 2021 for Application No. EP 21167802.4.

(Continued)

*Primary Examiner* — Sharon X Wen
(74) *Attorney, Agent, or Firm* — Wolf, Greenfield & Sacks, P.C.

(57) ABSTRACT

Provided herein are plasma kallikrein antibodies binding to active plasma kallikrein and methods of using such antibodies in preventing hereditary angioedema attack or reducing the rate of hereditary angioedema attack.

17 Claims, 13 Drawing Sheets

Specification includes a Sequence Listing.

(56) References Cited

U.S. PATENT DOCUMENTS

| | | | |
|---|---|---|---|
| 5,629,176 | A | 5/1997 | Bjørn et al. |
| 5,635,187 | A | 6/1997 | Bathurst et al. |
| 5,648,331 | A | 7/1997 | Koudsi et al. |
| 5,663,143 | A | 9/1997 | Ley et al. |
| 5,672,662 | A | 9/1997 | Harris et al. |
| 5,677,146 | A | 10/1997 | Sprecher et al. |
| 5,693,761 | A | 12/1997 | Queen et al. |
| 5,693,762 | A | 12/1997 | Queen et al. |
| 5,695,760 | A | 12/1997 | Faanes et al. |
| 5,696,088 | A | 12/1997 | Innis et al. |
| 5,719,041 | A | 2/1998 | Lazarus et al. |
| 5,736,364 | A | 4/1998 | Kelley et al. |
| 5,739,208 | A | 4/1998 | Harris |
| 5,747,449 | A | 5/1998 | Lasters et al. |
| 5,770,568 | A | 6/1998 | Auerswald et al. |
| 5,780,265 | A | 7/1998 | Dennis et al. |
| 5,786,328 | A | 7/1998 | Dennis et al. |
| 5,795,865 | A | 8/1998 | Markland et al. |
| 5,795,954 | A | 8/1998 | Lazarus et al. |
| 5,800,385 | A | 9/1998 | Demopulos et al. |
| 5,804,376 | A | 9/1998 | Braxton et al. |
| 5,834,244 | A | 11/1998 | Dennis et al. |
| 5,843,895 | A | 12/1998 | Lazarus et al. |
| 5,849,992 | A | 12/1998 | Meade et al. |
| 5,853,723 | A | 12/1998 | Jacobs et al. |
| 5,863,893 | A | 1/1999 | Dennis et al. |
| 5,869,637 | A | 2/1999 | Au-Young et al. |
| 5,874,407 | A | 2/1999 | Kelley et al. |
| 5,880,256 | A | 3/1999 | Dennis et al. |
| 5,900,461 | A | 5/1999 | Harris |
| 5,914,316 | A | 6/1999 | Brown et al. |
| 5,932,462 | A | 8/1999 | Harris et al. |
| 5,951,974 | A | 9/1999 | Gilbert et al. |
| 5,962,266 | A | 10/1999 | White et al. |
| 5,990,237 | A | 11/1999 | Bentley et al. |
| 5,994,125 | A | 11/1999 | Markland et al. |
| 6,001,596 | A | 12/1999 | Hillman et al. |
| 6,004,579 | A | 12/1999 | Bathurst et al. |
| 6,008,196 | A | 12/1999 | Curran et al. |
| 6,010,880 | A | 1/2000 | Markland et al. |
| 6,013,448 | A | 1/2000 | Braxton et al. |
| 6,013,763 | A | 1/2000 | Braisted et al. |
| 6,017,723 | A | 1/2000 | Rao et al. |
| 6,057,287 | A | 5/2000 | Markland et al. |
| 6,063,764 | A | 5/2000 | Creasey et al. |
| 6,071,723 | A | 6/2000 | Markland et al. |
| 6,087,473 | A | 7/2000 | Conklin et al. |
| 6,090,916 | A | 7/2000 | Vlasuk et al. |
| 6,103,499 | A | 8/2000 | Markland et al. |
| 6,103,500 | A | 8/2000 | Innis et al. |
| 6,113,896 | A | 9/2000 | Lazarus et al. |
| 6,126,933 | A | 10/2000 | Warne et al. |
| 6,159,938 | A | 12/2000 | Gyorkos et al. |
| 6,171,587 | B1 | 1/2001 | Wun et al. |
| 6,174,721 | B1 | 1/2001 | Innis et al. |
| 6,180,607 | B1 | 1/2001 | Davies et al. |
| 6,214,966 | B1 | 4/2001 | Harris |
| 6,242,414 | B1 | 6/2001 | Johnson et al. |
| 6,258,351 | B1 | 7/2001 | Harris |
| 6,261,279 | B1 | 7/2001 | Demopulos et al. |
| 6,306,884 | B1 | 10/2001 | Buckman et al. |
| 6,333,402 | B1 | 12/2001 | Markland et al. |
| 6,348,558 | B1 | 2/2002 | Harris et al. |
| 6,362,254 | B2 | 3/2002 | Harris et al. |
| 6,362,276 | B1 | 3/2002 | Harris et al. |
| 6,376,604 | B2 | 4/2002 | Kozlowski |
| 6,407,213 | B1 | 6/2002 | Carter et al. |
| 6,413,507 | B1 | 7/2002 | Bentley et al. |
| 6,423,498 | B1 | 7/2002 | Markland et al. |
| 6,432,397 | B1 | 8/2002 | Harris |
| 6,455,639 | B1 | 9/2002 | Yasukohchi et al. |
| 6,472,195 | B2 | 10/2002 | Hillman et al. |
| 6,515,100 | B2 | 2/2003 | Harris |
| 6,534,276 | B1 | 3/2003 | Wun et al. |
| 6,548,262 | B2 | 4/2003 | Gentz et al. |
| 6,576,235 | B1 | 6/2003 | Williams et al. |
| 6,583,108 | B1 | 6/2003 | Tamburini et al. |
| 6,610,281 | B2 | 8/2003 | Harris |
| 6,624,246 | B2 | 9/2003 | Kozlowski |
| 6,664,331 | B2 | 12/2003 | Harris et al. |
| 6,689,582 | B1 | 2/2004 | Davies et al. |
| 6,710,125 | B2 | 3/2004 | Kozlowski |
| 6,774,180 | B2 | 8/2004 | Kozlowski et al. |
| 6,783,960 | B2 | 8/2004 | Innis et al. |
| 6,783,965 | B1 | 8/2004 | Sherman et al. |
| 6,806,360 | B2 | 10/2004 | Wun et al. |
| 6,814,982 | B2 | 11/2004 | Poncin et al. |
| 6,914,135 | B2 | 7/2005 | Sheppard et al. |
| 6,953,674 | B2 | 10/2005 | Markland et al. |
| 6,989,369 | B2 | 1/2006 | Ladner et al. |
| 7,064,107 | B2 | 6/2006 | Ladner et al. |
| 7,067,144 | B2 | 6/2006 | Demopulos et al. |
| 7,078,383 | B2 | 7/2006 | Ley et al. |
| 7,153,829 | B2 | 12/2006 | Ladner et al. |
| 7,166,576 | B2 | 1/2007 | Cicardi et al. |
| 7,235,530 | B2 | 6/2007 | Blair et al. |
| 7,276,480 | B1 | 10/2007 | Ladner et al. |
| 7,550,427 | B2 | 6/2009 | Ley et al. |
| 7,628,983 | B2 | 12/2009 | Markland et al. |
| 7,704,949 | B2 | 4/2010 | Ladner et al. |
| 7,718,617 | B2 | 5/2010 | Cicardi et al. |
| 7,811,991 | B2 | 10/2010 | Ladner et al. |
| 7,851,442 | B2 | 12/2010 | Ladner et al. |
| 7,919,462 | B2 | 4/2011 | Markland et al. |
| 8,034,775 | B2 | 10/2011 | Ladner et al. |
| 8,124,586 | B2 | 2/2012 | Ladner et al. |
| 8,188,045 | B2 | 5/2012 | Blair et al. |
| 8,283,321 | B2 | 10/2012 | Markland et al. |
| 8,816,055 | B2 | 8/2014 | Sexton et al. |
| 8,822,653 | B2 | 9/2014 | Sexton et al. |
| 9,266,964 | B2 | 2/2016 | Sexton et al. |
| 10,316,095 | B2 | 6/2019 | Fowler et al. |
| 10,336,832 | B2 | 7/2019 | Sexton et al. |
| 10,370,453 | B2 | 8/2019 | Sexton et al. |
| 10,428,158 | B2 | 10/2019 | Conley et al. |
| 10,648,990 | B2 | 5/2020 | Sexton et al. |
| 11,046,785 | B2 | 6/2021 | Conley et al. |
| 11,084,884 | B2 | 8/2021 | Sexton et al. |
| 11,156,612 | B2 | 10/2021 | Sexton et al. |
| 11,286,307 | B2 | 3/2022 | Adelman et al. |
| 11,299,553 | B2 | 4/2022 | Nixon et al. |
| 11,340,237 | B2 | 5/2022 | Sexton et al. |
| 11,372,002 | B2 | 6/2022 | Sexton et al. |
| 11,401,346 | B2 | 8/2022 | Sexton et al. |
| 11,505,620 | B2 | 11/2022 | Sexton et al. |
| 11,892,450 | B2 | 2/2024 | Kusumam et al. |
| 12,084,515 | B2 | 9/2024 | Conley et al. |
| 12,110,343 | B2 | 10/2024 | Nixon et al. |
| 12,384,854 | B2 | 8/2025 | Sexton et al. |
| 12,460,016 | B2 | 11/2025 | Sexton et al. |
| 12,528,880 | B2 | 1/2026 | Nurse et al. |
| 2001/0027180 | A1 | 10/2001 | Isaacs |
| 2002/0102703 | A1 | 8/2002 | Sheppard et al. |
| 2002/0111460 | A1 | 8/2002 | Holloway |
| 2003/0012969 | A1 | 1/2003 | Clark |
| 2003/0096733 | A1 | 5/2003 | Ny et al. |
| 2003/0100070 | A1 | 5/2003 | Holloway |
| 2003/0113726 | A1 | 6/2003 | Tsuchihashi et al. |
| 2003/0114372 | A1 | 6/2003 | White et al. |
| 2003/0138417 | A1 | 7/2003 | Kaisheva et al. |
| 2003/0148271 | A1 | 8/2003 | Hillman et al. |
| 2003/0153046 | A1 | 8/2003 | Jensen et al. |
| 2003/0175919 | A1 | 9/2003 | Ley et al. |
| 2003/0223977 | A1 | 12/2003 | Ley et al. |
| 2004/0038893 | A1 | 2/2004 | Ladner et al. |
| 2004/0049018 | A1 | 3/2004 | Bailon et al. |
| 2004/0053206 | A1 | 3/2004 | Cicardi et al. |
| 2004/0062746 | A1 | 4/2004 | Martinez et al. |
| 2004/0062748 | A1 | 4/2004 | Martinez et al. |
| 2004/0106747 | A1 | 6/2004 | Bailon et al. |
| 2004/0126361 | A1 | 7/2004 | Saifer et al. |
| 2004/0152633 | A1 | 8/2004 | Jorgensen et al. |
| 2004/0171794 | A1 | 9/2004 | Ladner et al. |
| 2004/0180827 | A1 | 9/2004 | Chen et al. |

(56) References Cited

U.S. PATENT DOCUMENTS

| | | | |
|---|---|---|---|
| 2004/0209243 | A1 | 10/2004 | Nixon et al. |
| 2005/0004021 | A1 | 1/2005 | Sprecher et al. |
| 2005/0075665 | A1 | 4/2005 | Brenzel et al. |
| 2005/0089515 | A1 | 4/2005 | Ley et al. |
| 2005/0164928 | A1 | 7/2005 | Ladner et al. |
| 2005/0164945 | A1 | 7/2005 | Nixon et al. |
| 2005/0180977 | A1 | 8/2005 | Nixon et al. |
| 2006/0069020 | A1 | 3/2006 | Blair et al. |
| 2006/0194727 | A1 | 8/2006 | Ladner et al. |
| 2006/0228331 | A1 | 10/2006 | Peschke et al. |
| 2006/0264603 | A1 | 11/2006 | Markland et al. |
| 2007/0004910 | A1 | 1/2007 | Sexton et al. |
| 2007/0020252 | A1 | 1/2007 | Ladner et al. |
| 2007/0041959 | A1 | 2/2007 | Ley et al. |
| 2007/0049522 | A1 | 3/2007 | Ladner et al. |
| 2007/0065407 | A1 | 3/2007 | Patten et al. |
| 2007/0079096 | A1 | 4/2007 | Chen |
| 2007/0100133 | A1 | 5/2007 | Beals et al. |
| 2007/0117752 | A1 | 5/2007 | Larsen et al. |
| 2007/0213275 | A1 | 9/2007 | Clark et al. |
| 2007/0249807 | A1 | 10/2007 | Ladner et al. |
| 2007/0253949 | A1 | 11/2007 | Golz et al. |
| 2008/0038276 | A1 | 2/2008 | Sinha et al. |
| 2008/0038748 | A1 | 2/2008 | Kojima et al. |
| 2008/0050716 | A1 | 2/2008 | Cicardi et al. |
| 2008/0064637 | A1 | 3/2008 | Ladner et al. |
| 2008/0076712 | A1 | 3/2008 | Ladner et al. |
| 2008/0131426 | A1 | 6/2008 | Ladner et al. |
| 2008/0139473 | A1 | 6/2008 | Ladner et al. |
| 2008/0152656 | A1 | 6/2008 | Ladner et al. |
| 2008/0182283 | A1 | 7/2008 | Markland et al. |
| 2008/0188409 | A1 | 8/2008 | Blair et al. |
| 2008/0200646 | A1 | 8/2008 | Ladner et al. |
| 2008/0221031 | A1 | 9/2008 | Blair et al. |
| 2008/0226655 | A1 | 9/2008 | Ladner et al. |
| 2008/0255025 | A1 | 10/2008 | Ladner |
| 2008/0260752 | A1 | 10/2008 | Ladner et al. |
| 2008/0299050 | A1 | 12/2008 | Bortz et al. |
| 2009/0023651 | A1 | 1/2009 | Markland et al. |
| 2009/0062195 | A1 | 3/2009 | Ladner et al. |
| 2009/0075887 | A1 | 3/2009 | McPherson |
| 2009/0082267 | A1 | 3/2009 | Ladner et al. |
| 2009/0105142 | A1 | 4/2009 | Moscicki |
| 2009/0117130 | A1 | 5/2009 | Ladner et al. |
| 2009/0123475 | A9 | 5/2009 | Siegel |
| 2009/0215119 | A1 | 8/2009 | Ladner |
| 2009/0221480 | A1 | 9/2009 | Blair et al. |
| 2009/0227494 | A1 | 9/2009 | Blair et al. |
| 2009/0227495 | A1 | 9/2009 | Blair et al. |
| 2009/0233852 | A1 | 9/2009 | Blair et al. |
| 2009/0234009 | A1 | 9/2009 | Blair et al. |
| 2009/0247452 | A1 | 10/2009 | Ellis et al. |
| 2009/0247453 | A1 | 10/2009 | Blair et al. |
| 2009/0264350 | A1 | 10/2009 | Blair et al. |
| 2010/0034805 | A1 | 2/2010 | Ladner et al. |
| 2010/0183625 | A1 | 7/2010 | Sternlicht |
| 2010/0273721 | A1 | 10/2010 | Belichard |
| 2010/0285507 | A1 | 11/2010 | Cho et al. |
| 2010/0286061 | A1 | 11/2010 | Devy et al. |
| 2011/0008762 | A1 | 1/2011 | Cicardi et al. |
| 2011/0086801 | A1 | 4/2011 | Ladner et al. |
| 2011/0136746 | A1 | 6/2011 | Markland et al. |
| 2011/0142851 | A1 | 6/2011 | Misher et al. |
| 2011/0200611 | A1 | 8/2011 | Sexton |
| 2012/0201756 | A1 | 8/2012 | Sexton |
| 2012/0264798 | A1 | 10/2012 | Sinha et al. |
| 2012/0328517 | A1 | 12/2012 | Markland et al. |
| 2013/0012438 | A1 | 1/2013 | Blair et al. |
| 2013/0216556 | A1 | 8/2013 | Fowler et al. |
| 2014/0302048 | A1 | 10/2014 | Sexton et al. |
| 2014/0303357 | A1 | 10/2014 | Lim et al. |
| 2014/0335023 | A1 | 11/2014 | Sexton et al. |
| 2015/0274841 | A1 | 10/2015 | Conley et al. |
| 2015/0362492 | A1 | 12/2015 | Joseph et al. |
| 2015/0362493 | A1 | 12/2015 | Sexton et al. |
| 2016/0017055 | A1 | 1/2016 | Nixon et al. |
| 2016/0102150 | A1 | 4/2016 | Sexton et al. |
| 2017/0002094 | A1 | 1/2017 | Sexton et al. |
| 2018/0002447 | A1 | 1/2018 | Sexton et al. |
| 2018/0002448 | A1 | 1/2018 | Sexton et al. |
| 2018/0002449 | A1 | 1/2018 | Sexton et al. |
| 2018/0037664 | A1 | 2/2018 | Sexton et al. |
| 2018/0037665 | A1 | 2/2018 | Sexton et al. |
| 2018/0037666 | A1 | 2/2018 | Sexton et al. |
| 2018/0298110 | A1 | 10/2018 | Chyung et al. |
| 2018/0362664 | A1 | 12/2018 | Adelman et al. |
| 2019/0185580 | A1 | 6/2019 | Nixon et al. |
| 2020/0017602 | A1 | 1/2020 | Sexton et al. |
| 2020/0109213 | A1 | 4/2020 | Sexton et al. |
| 2020/0109214 | A1 | 4/2020 | Peng et al. |
| 2020/0115469 | A1 | 4/2020 | Conley et al. |
| 2020/0317815 | A1 | 10/2020 | Mendivil Medina |
| 2021/0087293 | A1 | 3/2021 | Sexton et al. |
| 2022/0033521 | A1 | 2/2022 | Conley et al. |
| 2022/0315668 | A1 | 10/2022 | Adelman et al. |
| 2023/0002509 | A1 | 1/2023 | Nixon et al. |
| 2023/0104754 | A1 | 4/2023 | Lu et al. |
| 2023/0112931 | A1 | 4/2023 | Sexton et al. |
| 2023/0192889 | A1 | 6/2023 | Nurse et al. |
| 2023/0340150 | A1 | 10/2023 | Sexton et al. |
| 2025/0129182 | A1 | 4/2025 | Nixon et al. |
| 2026/0035482 | A1 | 2/2026 | Chyung et al. |

FOREIGN PATENT DOCUMENTS

| | | | |
|---|---|---|---|
| BR | 112017020864 | A2 | 7/2018 |
| BR | 112013017080 | B1 | 4/2025 |
| CA | 2180950 | A1 | 8/1995 |
| CN | 1233256 | A | 10/1999 |
| CN | 101928346 | A | 12/2010 |
| CN | 103635489 | A | 3/2014 |
| CN | 105051068 | A | 11/2015 |
| CN | 105073778 | A | 11/2015 |
| CN | 106459210 | A | 2/2017 |
| CN | 108602893 | A | 9/2018 |
| CN | 109716129 | A | 5/2019 |
| DE | 69533472 | T2 | 1/2006 |
| EA | 2016/91470 | A1 | 12/2016 |
| EA | 2017/92161 | A1 | 4/2018 |
| EP | 0 132 732 | A2 | 2/1985 |
| EP | 0 210 029 | | 1/1987 |
| EP | 0 255 011 | A2 | 2/1988 |
| EP | 0 274 826 | | 7/1988 |
| EP | 0 285 123 | A2 | 10/1988 |
| EP | 0 301 122 | | 2/1989 |
| EP | 0 307 592 | A2 | 3/1989 |
| EP | 0 318 451 | | 5/1989 |
| EP | 0 401 508 | A2 | 12/1990 |
| EP | 0 486 001 | A1 | 5/1992 |
| EP | 0 621 870 | B1 | 11/1994 |
| EP | 0 621 871 | B1 | 11/1994 |
| EP | 0 739 355 | B1 | 10/1996 |
| EP | 1 288 305 | A2 | 3/2003 |
| EP | 1 484 339 | A2 | 12/2004 |
| JP | 7504891 | | 6/1995 |
| JP | H9-509838 | | 10/1997 |
| JP | 9511131 | | 11/1997 |
| JP | 10503375 | | 3/1998 |
| JP | 2002-524076 | A | 8/2002 |
| JP | 2006-501168 | A | 1/2006 |
| JP | 2008-514624 | | 5/2008 |
| JP | 2009-529553 | A | 8/2009 |
| JP | 2013-516478 | A | 5/2013 |
| JP | 2014-506257 | A | 3/2014 |
| JP | 2014-515763 | A | 7/2014 |
| JP | 2016-536012 | A | 11/2016 |
| JP | 2017-503820 | A | 2/2017 |
| JP | 2019-501886 | A | 1/2019 |
| JP | 6845012 | B2 | 3/2021 |
| JP | 7585193 | B2 | 11/2024 |
| KR | 10-2016-0122169 | A | 10/2016 |
| KR | 10-2799778 | B1 | 4/2025 |
| MX | 2017/012423 | A | 1/2018 |
| WO | WO 87/05396 | A1 | 9/1987 |

(56) References Cited

FOREIGN PATENT DOCUMENTS

| | | |
|---|---|---|
| WO | WO 1989/010374 A1 | 11/1989 |
| WO | WO 1990/002809 | 3/1990 |
| WO | WO 1992/006111 A1 | 4/1992 |
| WO | WO 1993/009233 A2 | 5/1993 |
| WO | WO 1993/014120 A1 | 7/1993 |
| WO | WO 1993/014121 A1 | 7/1993 |
| WO | WO 1993/014122 A1 | 7/1993 |
| WO | WO 1995/018830 A2 | 7/1995 |
| WO | WO 1995/021601 A2 | 8/1995 |
| WO | WO 1995/023860 | 9/1995 |
| WO | WO 1996/004378 | 2/1996 |
| WO | WO 1996/020278 | 7/1996 |
| WO | WO 1996/035788 A2 | 11/1996 |
| WO | WO 1997/033996 | 9/1997 |
| WO | WO 1998/052976 A1 | 11/1998 |
| WO | WO 1999/063090 A2 | 12/1999 |
| WO | WO 2000/014235 A1 | 3/2000 |
| WO | WO 2000/034317 A2 | 6/2000 |
| WO | WO 2001/009968 | 2/2001 |
| WO | WO 2001/014424 A2 | 3/2001 |
| WO | WO 2001/068707 | 9/2001 |
| WO | WO 2001/079480 A1 | 10/2001 |
| WO | WO 2002/006334 | 1/2002 |
| WO | WO 2002/006539 | 1/2002 |
| WO | WO 2002/092147 | 11/2002 |
| WO | WO 2002/094200 | 11/2002 |
| WO | WO 2003/066824 A2 | 8/2003 |
| WO | WO 2003/103475 A2 | 12/2003 |
| WO | WO 2004/019968 A1 | 3/2004 |
| WO | WO 2004/062646 A1 | 7/2004 |
| WO | WO 2004/062689 A1 | 7/2004 |
| WO | WO 2005/021556 | 3/2005 |
| WO | WO 2005/021557 A2 | 3/2005 |
| WO | WO 2005/075665 | 8/2005 |
| WO | WO 2006/017538 | 2/2006 |
| WO | WO 2006/036860 A2 | 4/2006 |
| WO | WO 2006/066878 A1 | 6/2006 |
| WO | WO 2006/089005 A2 | 8/2006 |
| WO | WO 2006/091459 A2 | 8/2006 |
| WO | WO 2007/079096 A2 | 7/2007 |
| WO | WO 2007/104541 A2 | 9/2007 |
| WO | WO 2007/106746 | 9/2007 |
| WO | WO 2008/000833 | 1/2008 |
| WO | WO 2009/026334 A2 | 2/2009 |
| WO | WO 2009/026539 A1 | 2/2009 |
| WO | WO 2009/102927 A1 | 8/2009 |
| WO | WO 2010/003475 | 1/2010 |
| WO | WO 2010/006746 | 1/2010 |
| WO | WO 2010/080833 | 7/2010 |
| WO | WO 2011/085103 | 7/2011 |
| WO | WO 2012/094587 | 7/2012 |
| WO | WO 2013/186700 A1 | 12/2013 |
| WO | WO 2014/113701 A1 | 7/2014 |
| WO | WO 2014/113712 A1 | 7/2014 |
| WO | WO 2014/152232 A2 | 9/2014 |
| WO | WO 2015/112578 A1 | 7/2015 |
| WO | WO 2016/160926 A1 | 10/2016 |
| WO | WO 2017/070170 A1 | 4/2017 |
| WO | WO 2017/100679 A1 | 6/2017 |
| WO | WO 2019/028362 A1 | 2/2019 |
| WO | WO 2019/048961 A1 | 3/2019 |
| WO | WO 2020/047352 A1 | 3/2020 |
| WO | WO 2020/186132 A1 | 9/2020 |

OTHER PUBLICATIONS

International Search Report and Written Opinion mailed Jun. 30, 2016 for Application No. PCT/US2016/024921.

International Preliminary Report on Patentability mailed Oct. 12, 2017 for Application No. PCT/US2016/024921.

Partial Supplementary European Search Report for Application No. EP 16774069.5 mailed Jul. 19, 2018.

Supplementary European Search Report for Application No. EP 16774069.5 mailed Oct. 26, 2018.

[No Author Listed] Dyax's DX-2930 granted Orphan Drug designation in hereditary angioedema. Dec. 6, 2013.

[No Author Listed] Efficacy and Safety Study of DX-2930 to prevent acute angioedema attacks in patients with Type I and Type II HAE. Study NCT02586805. ClinicalTrials.gov Apr. 9, 2019. 7pgs.

[No Author Listed] Fair Disclosure Wire, "Dyax Corp. announces positive results from phase la clinical trial of DX2930" dated Feb. 25, 2014. Last accessed from http://dialog.proquest.com/professional/printviewfile?accountid=157282 on May 20, 2016. p. 1-15.

Abdel-Salam et al., "Expression of mouse anticreatine kinase (MAK33) monoclonal antibody in the yeast Hansenula polymorpha", Appl. Microbiol. Biotechnol, vol. 56, p. 157-164 (2001).

Abuchowski et al., "Alteration of immunological properties of bovine serum albumin by covalent attachment of polyethylene glycol," J. Bio. Chem., 1977, vol. 252, pp. 3578-3581.

Abuchowski et al., "Cancer therapy with chemically modified enzymes, I., Antitumor properties of polyethylene glycol-asparaginase conjugates," Cancer Biochem. Biophys., 1984, vol. 7, pp. 175-186.

Abuchowski et al., "Effect of covalent attachment of polyethylene glycol on immunogenicity and circulating life of bovine," J. Biol. Chem., 1977, vol. 252, pp. 3582-3586.

Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs)and NSAIDs alone", Osteoarthritis and Cartilage, Bailliere Tindall, London, GB, vol. 3, No. 4, pp. 213-225, (Dec. 1, 1995).

Adelman et al., Proteolysis of Platelet Glycoprotein lb by Plasmin Is Facilitated by Plasmin Lysine-Binding Regions, Blood, vol. 68 (6): 1280-1284, (Dec. 1986).

Albrecht et al., Elastase inhibition by the inter-alpha-trypsin inhibitor and derived inhibitors of man and cattle. Hoppe Seylers Z Physiol Chem. Dec. 1983;364(12):1703-8.

Albrecht et al., Kunitz-type proteinase inhibitors derived by limited proteolysis of the inter-alpha-trypsin inhibitor, IX. Isolation and characterization of the inhibitory parts of inter-alpha-trypsin inhibitors from several mammalian sera. Hoppe Seylers Z Physiol Chem. Dec. 1983;364(12):1697-702.

Almagro et al., Humanization of antibodies. Front Biosci. Jan. 1, 2008;13:1619-33. doi: 10.2741/2786.

Altschul et al. "Gapped BLAST and PSI-BLAST: a new generation of protein database search programs." (1997) Nucleic Acids Res. 25:3389-3402.

Anba et al., Improving the Stability of a Foreign Protein in the Periplasmic Space of *Escherichia coli*, Biochimie, vol. 70(6): 727-733, (1988).

Angliker et al., The Synthesis of Lysylflouromethanes and their Properties as Inhibitors of Trypsin, Plasmin and Cathepsin B, Biochemistry, 241:871-875, (1987).

Asano et al., "Effects of a nonpeptide bradykinin B2 receptor antagonist, FR167344, on different in vivo animal models of inflammation", Br J Pharmacol, vol. 122, p. 1436-1440 (1997).

Asano M. et al., Br J Pharmacol, vol. 122, p. 1436-1440 (1997).

Atherton et al., Peptide Synthesis. Part 2. Procedures for Solid Phase Synthesis using Nα-Fluorenylmethycarbonylamino-acids on Polyamide Supports. Synthesis of Substance P and of Acyl Carrier Protein 65-74 Decapeptide, J. Chem. Soc. Perkins Trans, 1:538-546, (1981).

Attwood, The Babel of Bioinformatics; Science, vol. 290, pp. 471-473 (2000).

Auerswald et al., Expression, Isolation and Characterization of Recombinant [Arg15, Glu52] Aprotinin, Bio. Chem. Hoppe-Seyler, 369:(Suppl)27-35 (1988).

Baba et al., States of Tyrosyl Residues and Circular Dichroism of Kunitz Trypsin Inhibitor, J. Biochem 65 (1):113-121 (1969).

Bagdasarian et al., Immunochemical studies of plasma kallikrein. J Clin Invest. Dec. 1974;54(6):1444-54.

Balduyck et al., Human Urinary Proteinase Inhibitor: Inhibitory Properties and Interaction with Bovine Trypsin, Bio. Chem. Hoppe-Seyler, vol. 366: 9-14, (1985).

(56) References Cited

OTHER PUBLICATIONS

Banerji et al., Effect of Lanadelumab Compared With Placebo on Prevention of Hereditary Angioedema Attacks: A Randomized Clinical Trial. JAMA. Nov. 27, 2018;320(20):2108-2121. doi: 10.1001/jama.2018.16773.
Banerji et al., Inhibiting Plasma Kallikrein for Hereditary Angioedema Prophylaxis. N Engl J Med. Feb. 23, 2017;376(8):717-728. doi: 10.1056/NEJMoa1605767.
Banerji et al., Lanadelumab 300mg every 2 weeks effectively prevented hereditary angioedema attacks in the help study. Ann Allerg Asthma Im. Nov. 1, 2018;121(5):S5.
Baneyx et al., "In Vivo Degradation of Secreted Fusion Proteins by the *Escherichia coli* Outer Membrane Protease OmpT", J. Bacteriol., 172:491-494, (1990).
Baneyx et al., Construction and Characterization of *Escherichia coli* Strains Deficient in Multiple Secreted Proteases: Protease III Degrades High-Molecular-Weight Substrates In Vivo, J Bacteriol., 173:2696-2703 (1991).
Basu et al., "Structure-function engineering of interferon-b-1b for improving stability, solubility, potency, immunogenicity, and pharmacokinetic properties by site-selective mono-PEGylation," Bioconjugate Chemistry, 2006, vol. 17, pp. 618-630.
Baumann, "A multi-level study of recombinant Pichia pastoris in different oxygen conditions", BMC Syst Biol. 4:141 (Oct. 22, 2010).
Bayes et al., "Gateways to Clinical Trials" Methods Find Exp. Clin. Pharmacol., vol. 28(3): pp. 185-206 (2006).
Beckmann et al., "Preparation of chemically mutatedaprotinin homologues by semisynthesis-P1 substitutions change inhibitory specificity," Eur. J. Biochem., vol. 176, pp. 675-682 (1988).
Beech et al., "Further characterisation of a thromboembolic model of stroke in the rat" Brain Res, vol. 895, p. 18-24 (2001).
Bendig, Humanization of Rodent Monoclonal Antibodies by CDR Grafting. Companion to Methods in Enzymology. 1995;8:83-93.
Berge et al., "Pharmaceutical salts", J. Pharm. Sci. 66:1-19 (1977).
Bergthorsdottir et al., "Signals that initiate somatic hypermutation of B cell in vitro", J. Immunol., p. 166:2228 (2001).
Berndt et al., "Designed Replacement of an Internal Hydration Water Molecule in BPTI: Structural and Functional Implications of a Glycine-to-Serine Mutation," Biochemistry, 32: 4564-4570 (1993).
Bhoola et al., "Bioregulation of Kinins: Kallikreins, Kininogens and Kininases," Pharmacological Reviews, 44 :1-80 (1992).
Bird et al. "Single chain antigen binding proteins", Science 242:423-426 (1988).
Blaber et al., "Targeting kallikrein 6-proteolysis attenuates CNS inflammatory disease," FASEB J. May 2004; 18(7):920-2. Epub Mar. 19, 2004.
Blijlevens et al., Palifermin (recombinant keratinocyte growth factor-1): a pleiotropic growth factor with multiple biological activities in preventing chemotherapy- and radiotherapy-induced mucositis. Ann Oncol. May 2007;18(5):817-26. Epub Oct. 9, 2006.
Bodanszky et al., The Practice of Peptide Synthesis (Springer-Verlag, New York, 1984).
Bork, "Powers and pitfalls in sequence analysis: the 70% hurdle," Genome Research, vol. 10, pp. 398-400 (2000).
Borregaard et al., "Granules of the human neutrophilic polymorphonuclear leukocyte," Blood, 1997, vol. 89, No. 10, pp. 3503-3521.
Bova et al., Lanadelumab Injection Treatment for the Prevention of Hereditary Angioedema (HAE): Design, Development and Place in Therapy. Drug Des Devel Ther. Oct. 22, 2019;13:3635-3646. doi: 10.2147/DDDT.S192475.
Bowdish et al., "Yeast expression of a catalytic antibody with chorismate mutase activity.", J Biol Chem.; 266 (18):11901-8 (Jun. 25, 1991).
Bowie et al. "Deciphering the message in protein sequences: tolerance to amino acid substitutions." Science 247:1306-1310 (1990).
Branden et al., "Prediction, Engineering, and Design of Protein," Introduction to Protein Structure, 1991, p. 247, Garland Publishing Inc., New York.
Breedveld, Therapeutic monoclonal antibodies. Lancet. Feb. 26, 2000;355(9205):735-40. Review.
Brenner, "Errors in genome annotation," Trends in Genetics, vol. 15, No. 4, pp. 132-133 (1999).
Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).
Browne et al., "Expression of Recombinant Human Plasminogen and Aglycoplasminogen in HeLa Cells," Genebank, Accession No. M74220 (1991).
Broze et al., "Regulation of Coagulation by a Multivalent Kunitz-Type Inhibitor," Biochemistry, 29:7539-7546, (1990).
Brus et al., "Disease Severity Is Correlated with Plasma Clotting and Fibrinolytic and Kinin- Kallikrein Activity in Neonatal Respiratory Distress Syndrome," Pediatric Research, 41:120-127, (1997).
Buchan et al., "A new model of temporary focal neocortical ischemia in the rat", Stroke 23 (2): 273-9 (1992).
Budavari, ed., Merck index, 11th ed., ISBN 911910-28-X, entries 923, 1745, 2740, 7425, (1989).
Buras et al., "Animal models of sepsis: setting the stage", Nat Rev Drug Discov. 4(10):854-65 (2005).
Burrage et al., "Matrix metalloproteinases: role in arthritis," Frontiers in Bioscience, 2006, vol. 11, pp. 529-543.
Burton et al. "Human Antibody Effector Function", Adv. Immunol. 51:1-84 (1992).
Busse et al., Efficacy and safety of lanadelumab for prophylactic treatment in adolescents with hereditary angioedema (HAE). Feb. 2019;143(2):AB43.
Cantor et al., "Elastin and Elastases in Lung Disease", Elastin and Elastases, Chapter 16, vol. II, pp. 159-168 (1989).
Carey et al., Advanced Organic Chemistry, 3rd Edition, Part B: Reactions and Synthesis, Plenum Press, New York: 678-686 (1990).
Carmichael, "Rodent models of focal stroke: size, mechanism, and purpose", NeuroRx 2: 396-409 (2005).
Carpenter et al., "Rational design of stable lyophilized protein formulations: theory and practice," Pharmaceutical Biotechnology, vol. 13, pp. 109-133 (2002).
Casati et al., Tranexamic acid compared with high-dose aprotinin in primary elective heart operations: effects on perioperative bleeding and allogeneic transfusions. J Thorac Cardiovasc Surg. Sep. 2000;120(3):520-7.
Casset et al., A peptide mimetic of an anti-CD4 monoclonal antibody by rational design. Biochem Biophys Res Commun. Jul. 18, 2003;307(1):198-205.
Cassim et al., "Kallikrein cascade and cytokines in inflamed joints," Pharmacology and Therapeutics, 2002, vol. 94, pp. 1-34.
Cernak, "Animal models of head trauma", NeuroRx. 2(3): 410-422 (2005).
Chen et al., "A model of focal ischemic stroke in the rat: reproducible extensive cortical infarction", Stroke 17 (4): 738-43 (1986).
Chen et al., "Establishment of an animal model of oral mucositis induced by conditioning regimen of haematopoietic stem cell transplantation" Zhonghua Kou Qiang Yi Xue Za Zhi. 42(11):672-6 (2007). (Abstract only).
Chen et al., "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol., 164:283-311 (1983).
Chen et al., Selection and analysis of an optimized anti-VEGF antibody: crystal structure of an affinity-matured Fab in complex with antigen. J Mol Biol. Nov. 5, 1999;293(4):865-81.
Chen et al., Solution Structure of a Kunitz-type Chymotrypsin Inhibitor Isolated from the Elapid Snake Bungarus Fasciatus, J. Biological Chemistry 276:45079-45087 (2001).
Chothia et al. "Canonical structures for the hypervariable regions of immunoglobulins." (1987) J. Mol. Biol. 196:901-917 (1987).

(56) References Cited

OTHER PUBLICATIONS

Chothia et al. "Structural Repertoire of the Human VH Segments", J. Mol. Biol. 227:799-817 (1992).
Chung et al., "Human plasma prekallikrein, a zymogen to a serine protease that contains four tandem repeats," GenBank, Accession #P03952 (1986).
Churg et al., "Proteases and emphysema," Curr. Opin. Pulm. Med., 2005, vol. 11, pp. 153-159.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Colman et al., "Contact System: A Vascular Biology Modulator With Anticoagulant, Profibrinolytic, Antiadhesive, and Proinflammatory Attributes" Blood, 90, 3819-3843 (1997).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).
Colman et al., Hemostasis and Thrombosis Basic Principles and Clinical Practice, Chapter 1, 2nd Edition, 3-17 (1987).
Colman R. W., "Plasma and tissue Kallikrein in Arthritis and Inflammatory Bowel Disease", Immunopharmacology, Jan. 1, 1999, pp. 103-108, vol. 43, No. 2/03, Elsevier Science Publishers, BV.
Colman RW et al., "Activation of the kallikrein-kinin system in arthritis and enterocolitis in genetically susceptible rats: modulation by a selective plasma kallikrein inhibitor", Proceedings of the Association of American Physicians, Jan. 1, 1997,pp. 10-22, vol. 109, No. 1, Cambridge, MA US.
Cook et al., The human immunoglobulin VH repertoire. Immunol Today. May 1995; 16(5):237- 42.
Corpet, et al. "Recent improvements of the ProDom database of protein domain families" Nucl. Acids Res. 27:263-267 (1999).
Cumming et al., "Hemodynamic, Renal, and Hormonal Aprotinin in an Ovine Model of Septic Shock," Critical Care Medicine, 20:1134-1139 (1992).
Cunningham et al., "Structural and functional characterization of tissue factor pathway inhibitor following degradation by matrix metalloproteinase-8," Biochem. J., 2002, vol. 367, pp. 451-458.
Current Protocols in Molecular Biology, John Wiley & Sons, N.Y. (1989) 6.3.1-6.3.6.
Currie et al., "Design and Synthesis of a Bicyclic Non-Peptide B-Bend Mimetic of Enkephalin," Tetrahedron, 49:3489-3500 (1993).
De Agostini et al., Human plasma kallikrein and C1 inhibitor form a complex possessing an epitope that is not detectable on the parent molecules: demonstration using a monoclonal antibody. Proc Natl Acad Sci U S A. Aug. 1985;82(15):5190-3.
De Campos et al., "Antioedematogenic and antinociceptive actions of NPC 18521, a novel bradykinin B2 receptor antagonist", Eur J Pharmacol. 316, 277-286 (1996).
De Haard et al. "A large non-immunized human Fab fragment phage library that permits rapid isolation and kinetic analysis of high affinity antibodies". J. Biol. Chem 274:18218-30, (1999).
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
De Wildt et al. "Antibody arrays for high-throughput screening of antibody-antigen interactions", Nat. Biotechnol. 18:989-994 (2000).
De Wildt et al., "Characterization of human variable domain antibody fragments against the U1 RNA-associated A protein, selected from a synthetic and patient-derived combinatorial V gene library" Eur J Immunol. 26(3):629-39 (1996).
Debiopharm brochure, "Engineering protein inhibitor of human neutrophil elastase EPIO-hNE4 (DX-890)," Dated Oct. 2004, printed from www.debio.com/e/pdf/fiche.sub.--epi.sub.--hne4.sub.--e.pdf.
Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).
Dela Cadena, et al., "Inhibition of Plasma Kallikrein Prevents Peptidoglycan-Induced Arthritis in the Lewis Rat," FASEB Journal, 9:446-452 (1995).
Delacourt et al., "Protection against acute lung injury by intravenous or intratracheal pretreatment with EPI-HNE-4, a new potent neutrophil elastase inhibitor," Am. J. Respir. Cell Mol. Biol., Mar. 26, 2002, vol. 26, No. 3, pp. 290-297.
Delaria et al., "Characterization of placental bikunin, a novel human serine protease inhibitor," J. Biological Chemistry, May 2, 1997, vol. 272, No. 18, pp. 12209-12214.
Delgado et al., "The uses and properties of PEG-linked proteins," Critical Review in Therapeutic Drug Carrier Systems, 1992, vol. 9, No. 3,4, pp. 249-304.
Deng et al., "Production of recombinant humanized anti-HBsAg Fab antibody by fermentation" Sheng Wu Gong Cheng Xue Bao, 20(5):800-4 (Sep. 2004) (Abstact Only).
Dennis et al., "Kunitz Domain Inhibitors of Tissue Factor-Factor VIIa (I. Potent Inhibitors Selected from Libraries by Phage Display)," Journal of Biological Chemistry 269:22129-22136 (1994).
Dennis et al., "Kunitz Domain Inhibitors of Tissue Factor-Factor Vila (II. Potent and Specific Inhibitors by Competitive Phage Selection)," Journal of Biological Chemistry, 269:22137-22144 (1994).
Dennis et al., "Potent and Selective Kunitz Domain Inhibitors of Plasma Kallikrein Designed by Phage Display," J. Biol. Chem., 270:25411-25417 (1995).
Devani et al., "Kallikrein-kinin system in inflammatory bowel disease: intestinal involvement and correlation with the degree of tissue inflammation," Digestive and Liver Disease, 2005, vol. 37, pp. 665-673.
Dhalluin et al., "Structural, kinetic, and thermodynamic analysis of the binding of the 40kDa PEG-interferon-a-2a and its individual positional isomers to the extracellular domain of the receptor IFNAR2," Bioconjugate Chemistry, 2005, vol. 16, pp. 518-527.
Diaz et al., "The Design of Water Soluble β-Sheet Structure Based on a Nucleation Strategy," Tetrahedron, 49:3533-3545 (1993).
Dimaio et al., "A New Class of Potent Thrombin Inhibitors That Incorporates a Scissile Pseudopeptide Bond," FEBS Lett, 282(1):47-52 (1991).
Dittmar et al., "External carotid artery territory ischemia impairs outcome in the endovascular filament model of middle cerebral artery occlusion in rats" Stroke 34: 2252-7 (2003).
Dittmar et al., "Fischer-344 rats are unsuitable for the MCAO filament model due to their cerebrovascular anatomy" J Neurosci Methods 156: 50 (2006).
Doerks et al., "Protein annotation: detective work for function prediction," Trends in Genetics, vol. 14, No. 6, pp. 248-250 (1998).
Donnelly et al., "Therapy for chronic obstructive pulmonary disease in the 21st century," Drugs, 2003, vol. 63, pp. 1973-1998.
Dragosits et al., "The effect of temperature on the proteome of recombinant Pichia pastoris", J Proteome Res. Mar. 2009;8(3):1380-92. 16 pages.
Dragosits et al., "The response to unfolded protein is involved in osmotolerance of Pichia pastoris" BMC Genomics. Mar. 26, 2010;11:207.
Druar et al., Analysis of the expressed heavy chain variable-region genes of Macaca fascicularis and isolation of monoclonal antibodies specific for the Ebola virus' soluble glycoprotein Immunogenetics, 57(10):730-8 (2005).
Dufton, "Protein inhibitors and dendrotoxins," Eur. J. Biochem., vol. 153, pp. 647-654. (1985).
Edqvist, et al., "Production of functional IgM Fab fragments by *Saccharomyces cerevisiae*", J Biotechnol 20 (3):291-300 (1991).
Eigenbrot et al., "Structural Effects Induced by Removal of a Disulfide-Bridge: The X-ray Structure of the C30A/C51A Mutant of Basic Pancreatic Trypsin Inhibitor at 1.6 A," Protein Engineering, 3:591-598 (1990).
Ellis et al., "The Urokinase Receptor: Involvement in Cell Surface Proteolysis and Cancer Invasion," Ann. NY. Acad. Sci., 667:13-31 (1992).
Enzon Pharmaceuticals, Macromolecular Engineering Technologies, 2004, pp. 1-14.
Falquet et al., "The PROSITE database, its status in 2002." (2002) Nucleic Acids Res. 30:235-238.
Faucette et al., Biomarker Assay for the detection of contact system activation. Ameri Soc. Hemato. Nov. 15, 2013; 122(21):2347. 55th

(56) References Cited

OTHER PUBLICATIONS

Annual Meeting of the American Society-of-Hematology. New Orleans, LA, USA. Dec. 7-10, 2013.
Feener, Plasma kallikrein and diabetic macular edema. Curr Diab Rep. Aug. 2010;10(4):270-5. doi: 10.1007/s11892-010-0127-1.
Ferrara et al., Recombinant renewable polyclonal antibodies. MAbs. 2015;7(1):32-41. doi: 10.4161/19420862.2015.989047.
Fidler et al., "The Implications of Angiogenesis for the Biology and Chemistry of Cancer Metastasis," Cell, 79:185-188 (1994).
Fields et al., "Solid Phase Peptide Synthesis Utilizing 9-fluorenylmethocarbonyl Amino Acids," Int. J. Peptide Protein Research, 35:161-214 (1990).
Fife et al., "Cartilage matrix glycoprotein is present in serum in experimental canine osteoarthritis" J Clin Invest. 84(5):1432-1439 (1989).
Fink et al., Cellular expression of plasma prekallikrein in human tissues. Biol Chem. Sep. 2007;388(9):957-63.
Fraedrich et al., "Reduction of Blood Transfusion requirement in Open Heart Surgery by Administration of High Doses of Aprotinin-Preliminary Results," Thorac Cardiovasc Surgeon, 37:89-91 (1989).
Frank, 8. Hereditary angioedema. J Allergy Clin Immunol. Feb. 2008;121(2 Suppl):S398-401; quiz S419. doi: 10.1016/j.jaci.2007.07.057.
Fredrich et al., "A new animal model of venous thrombosis in rats with low flow conditions in the venous blood stream" Blood Coagul Fibrinolysis. 5(2):243-8 (1994).
Freidinger et al., "Protected Lactam-Bridged Dipeptides for Use as Conformational Constraints in Peptides," Journal of Organic Chemistry, 47:104-109 (1982).
Fries et al., "Inter-a-inhibitor, hyaluronan and inflammation," Acta Biochimica Polonica, 2003, vol. 50, No. 3, pp. 735-742.
Frisbie, "An animal model for venous thrombosis and spontaneous pulmonary embolism." Spinal Cord 43, 635-639 (2005).
Galeffi et al., "Functional expression of a single-chain antibody to ErbB-2 in plants and cell- free systems" J Transl Med. Sep. 29, 2006;4:39. 13 pages.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Gardell et al., "The Search for the Ideal Thrombolytic Agent: Maximize the Benefit and Minimize the Risk," Toxicologic Pathology, 21(2):190-198 (1993).
Gasser et al., "Engineering of Pichia pastoris for improved production of antibody fragments" Biotechnol Bioeng. Jun. 5, 2006;94(2):353-61.
GENBANK Submission; NIH/NCBI, Accession No. NM_008455.2 (GI: 236465804): "Plasma kallikrein precursor", GenBank Record created on Dec. 29, 2010.
GENBANK Submission; NIH/NCBI, Accession No. NM_012725.2 (GI:162138904): "Plasma kallikrein precursor", GenBank Record created on Dec. 26, 2010.
GENBANK Submission; NIH/NCBI, Accession No. NP_000217.2 (GI:55956899): "keratin, type I cytoskeletal 9 ", GenBank Record created on Dec. 27, 2010.
GENBANK Submission; NIH/NCBI, Accession No. NP_000418.2 (GI:109255251): "loricrin", GenBank Record created on Nov. 3, 2010.
GENBANK Submission; NIH/NCBI, Accession No. NP_000883.2 (GI: 78191798): "Plasma kallikrein preproprotein", GenBank Record created on Nov. 21, 2010.
GENBANK Submission; NIH/NCBI, Accession No. NP_000892 (GI: 158508572): "mineralocorticoid receptor isoform 1", GenBank Record created on Dec. 27, 2010.
GENBANK Submission; NIH/NCBI, Accession No. NP_005850.1 (GI:5032007): "transcriptional activator protein Pur-alpha", GenBank Record created on Dec. 28, 2010.
GENBANK Submission; NIH/NCBI, Accession No. NP_006228.3 (GI:110347449): "POU domain, class 4, transcription factor 1", GenBank Record created on Dec. 27, 2010.
GENBANK Submission; NIH/NCBI, Accession No. NP_009060.2 (GI:22547197): "zinc finger protein ZIC 2", GenBank Record created on Dec. 24, 2010.
GENBANK Submission; NIH/NCBI, Accession No. NP_031393.2 (GI:21396480): "RNA-binding protein Raly isoform 2", GenBank Record created on Dec. 25, 2010.
GENBANK Submission; NIH/NCBI, Accession No. NP_032481.2 (GI: 236465805): "Plasma kallikrein precursor", GenBank Record created on Dec. 29, 2010.
GENBANK Submission; NIH/NCBI, Accession No. NP_036857.2 (GI:162138905): "Plasma kallikrein precursor", GenBank Record created on Dec. 26, 2010.
GENBANK Submission; NIH/NCBI, Accession No. NP_056932.2 (GI:153791670): "Plasma kallikrein preproprotein", GenBank Record created on Dec. 27, 2010.
GENBANK Submission; NIH/NCBI, Accession No. NP_061856.1 (GI:9506713): "H/ACA ribonucleoprotein complex subunit 1", GenBank Record created on Dec. 24, 2010.
GENBANK Submission; NIH/NCBI, Accession No. NP_065104.1 (GI:9966841): "cell death regulator Aven", GenBank Record created on Dec. 26, 2010.
GENBANK Submission; NIH/NCBI, Accession No. NP_115818.2 (GI:53829370): "neuralized-like protein 4 isoform 1", GenBank Record created on Dec. 27, 2010.
GENBANK Submission; NIH/NCBI, Accession No. NP_476429.2 (GI:109148552): "keratin, type II cytoskeletal 3", GenBank Record created on Dec. 24, 2010.
GENBANK Submission; NIH/NCBI, Accession No. NP_631961.1 (GI:21327701): "TATA-binding protein-associated factor 2N isoform 1", GenBank Record created on Dec. 25, 2010.
GENBANK Submission; NIH/NCBI, Accession No. NP_787059.2 (GI:40068462): "At-rich interactive domain-containing protein 1B isoform 3", GenBank Record created on Mar. 4, 2010.
GENBANK Submission; NIH/NCBI, Accession No. XP_376532.2 (GI:51465288): "Predicted: KIAA0408", GenBank Record created on Aug. 19, 2004.
Gerriets et al., "Complications and pitfalls in rat stroke models for middle cerebral artery occlusion: a comparison between the suture and the macrosphere model using magnetic resonance angiography", Stroke 35: 2372-2377 (2004).
Gerriets et al., "The macrosphere model: evaluation of a new stroke model for permanent middle cerebral artery occlusion in rats" J Neurosci Methods 122: 201-11 (2003).
Girard et al., "Functional Significance of the Kunitz-type Inhibitory Domains of Liporotein-Associated Coagulation Inhibitor," Nature, 338:518-520 (1989).
Girard et al., "Structure of the Human Lipoprotein-associated Coagulation Inhibitor Gene," The Journal of Biological Chemistry, 266:5036-5041 (1991).
Goldenberg et al., "Circular and circularly permuted forms of bovine pancreatic trypsin inhibitor," J. Mol. Biol., vol. 165, pp. 407-413 (1983).
Gomez-Jorge et al., "The Double-Tuck Model: A New Animal Model of Arterial Thrombosis" J. Vasco Inter. Rad. 9 (4): 633-638 (1998).
Gonzalez-Quevedo et al., The Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Gouzy et al. "Whole genome protein domain analysis using a new method for domain clustering" (1999) Computers and Chemistry 23:333-340.
Graham et al., "Animal models of ischemic stroke: balancing experimental aims and animal care", Comp Med 54: 486-496 (2004).
Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.
Greilich et al., "Antigibrinolytic therapy during cardiopulmonary bypass reduces proinflammatory cytokine levels: a randomized,

(56) References Cited

OTHER PUBLICATIONS double-blind, placebo-controlled study of x-aminocaproic acid and aprotinin," J. Thorac. Cardiovasc. Surg., 2003, vol. 126, pp. 1498-1503.
Gribskov et al. "Profile analysis." (1990) Meth. Enzymol. 183:146-159.
Gribskov et al. "Profile analysis: detection of distantly related proteins." (1987) Proc. Natl. Acad. Sci. USA 84:4355-4358.
Grimaldi et al., "Trasylol in the treatment of acute arthritis due to microcrystals," Reumatismo, vol. 23, No. 5, pp. 217-221, (1971) (Abstract only).
Gullberg et al., "Biosynthesis, processing and sorting of neutrophil proteins: insight into neutrophil granule development," Eur. Journal of Haematology, 1997, vol. 58, pp. 137-153.
Guzman et al. "Mono-iodoacetate-induced histologic changes in subchondral bone and articular cartilage of rat femorotibial joints: an animal model of osteoarthritis." Toxicol Pathol. 31(6):619-24 (2003).
Hagihara et al., "Screening for stable mutants with amino acid pairs substituted for the disulfide bond between residues 14 and 38 of bovine pancreatic trypsin inhibitor (BPTI)," The Journal of Biological Chemistry, 2002, vol. 277, No. 52, pp. 51043-51048.
Han et al., Increased Vascular Permeability in C1 Inhibitor-Deficient Mice Mediated by the Bradykinin Type 2 Receptor, J. Clinical Investigation 109(8):1057-1063 (2002).
Han, Reversal of the Increased Vascular Permeability in C1 Inhibitor Deficient Mice: Therapeutic Approaches, International Immunopharmacology 2(9):1315 Abstract 176 (2002).
Hanes et al., "Picomolar affinity antibodies from a fully synthetic naive library selected and evolved by ribosome display" Nat Biotechnol. 18:1287-92 (2000).
Hanes et al., "Selecting and evolving functional proteins in vitro by ribosome display" Methods Enzymol. 328:404-30 (2000).
Harvey et al., "Engineering of recombinant antibody fragments to methamphetamine by anchored periplasmic expression" J Immunol Methods. Jan. 20, 2006;308(1-2):43-52. Epub Nov. 22, 2005.
Herter et al., "Hepatocyte growth factor is a preferred in vitro substrate for the human hepsin, a membrane-anchored serine protease implicated in prostate and ovarian cancers," Biochem. J., 2005, vol. 390, pp. 125-136.
Hoet et al., "Generation of high-affinity human antibodies by combining donor-derived and synthetic complementarity-determining-region diversity" Nat Biotechnol. 23(3)344-8 (2005).
Holliger et al., Engineered antibody fragments and the rise of single domains. Nat Biotechnol. Sep. 2005;23(9):1126-36.
Hoogenboom et al., "Antibody phage display technology and its applications" Immunotechnology 4:1-20 (1998).
Hoogenboom et al., "Natural and designer binding sites made by phage display technology" Immunol Today 2:371-8 (2000).
Hoover et al., "Amino Acids of the Recombinant Kringle 1 Domain of Human Plasminogen that Stabilize Its Interaction w-Amino Acids," Biochemistry, 32:10936-10943 (1993).
Hortin et al., "Allosteric Changes in Thrombin's Activity Produced by peptides Corresponding to Segments of Natural Inhibitors and Substrates," The Journal of Biological Chemistry, 266:6866-6871 (1991).
Horwitz et al., "Secretion of functional antibody and Fab fragment from yeast cells.", Proc Natl Acad Sci U S A. 85 (22):8678-82 (Nov. 1988).
Hostomsky et al., "Solid Phase Assembly of Cow Colostrum Trypsin Inhibitor Gene," Nucleic Acids Research, 15:4849-4856 (1987).
Huang et al., "Kinetics of factor Xa inhibition by tissue factor pathway inhibitor," The Journal of Biological Chemistry, 1993, vol. 268, No. 36, pp. 26950-26955.
Huang et al., "Novel peptide inhibitors of angiotensin-converting enzyme 2," The Journal of Biological Chemistry, 2003, vol. 278, No. 18, pp. 15532-15540.
Huge et al., "A model to investigate postoperative ileus with strain gauge transducers in awake rats" J Surg Res. 74 (2):112-8 (1998). (Abstact Only).
Huston et al., "Protein engineering of antibody binding sites: Recovery of specific activity in anti-digoxin single-chain Fv analogue produced in *Escherichia coli*", Proc. Natl. Acad. Sci. USA 85:5879-5883 (1988).
Hynes et al., X-ray crystal structure of the protease inhibitor domain of Alzheimer's amyloid beta-protein precursor. Biochemistry, 29:10018-10022 (1990).
Janeway et al., The interaction of the antibody molecule with specific antigen. Immunobiology: The Immune System in Health and Disease.5th edition. New York: Garland Science; 2001. NCBI Bookshelf. 5 pages.
Jefferis et al., "IgG-Fc-mediated effector functions: Molecular definition of interaction site for effector ligands and the role of gylcosylation", Immunol. Rev. 163:59-76, (1998).
Jones et al., "Severe prekallikrein deficiency associated with homozygosity for an Arg94Stop nonsense mutation" Br J Haematol, 2004. 127(2): p. 220-3.
Jonkam et al., "Effects of the bradykinin B2 receptor antagonist icatibant on microvascular permeability after thermal injury in sheep" Shock, 28:704-709 (2007).
Jorg et al., Kinetic analysis of plasminogen activation by purified plasma kallikrein. Thromb Res. Aug. 1, 1985;39(3):323-31.
Jostock et al., "Rapid generation of functional human IgG antibodies derived from Fab-on-phage display libraries" J. Immunol. Methods, 289(1-2):65-80 (2004).
Jul.; 55(7):439-448. doi: 10.1358/dot.2019.55.7.2985293.
Kabet et al. Sequences of Proteins of Immunological Interest, Fifth Edition, U.S. Dept. of Health and Human Services, NIH Publication No. 91-3242 (1991).
Kantor et al., "The experimental animal models for assessing treatment of restenosis" Cardiovasc Radiat Med. 1 (1):48-54 (1999).
Kaplan et al., A prealbumin activator of prekallikrein. 3. Appearance of chemotactic activity for human neutrophils by the conversion of human prekallikrein to kallikrein. J Exp Med. Jan. 1972;135(1):81-97.
Katre et al., "Chemical modification of recombinant interleukin 2 by polyethylene glycol increases its potency in the murine Meth A sarcoma model," Pnas USA, 1987, vol. 84, pp. 1487-1491.
Katre et al., "Immunogenicity of recombinant IL-2 modified by covalent attachment of polyethylene glycol," J. Immunol., 1990, vol. 144, pp. 209-213.
Katz et al., "Animal models of vasculitides" Clin Rev Allergy Immunol. 35(1-2): 11-8 (2008).
Kaufman et al., "Amplification and expression of sequences cotransfected with a modular dihydrofolate reductase complementary dna gene", Mol. Biol. 159:601 621 (1982).
Kelly et al., "Diabetes insipidus in uricase-deficient mice: a model for evaluating therapy with poly(ethylene glycol)-modified," J. Am. Soc. Nephrol., 2001, vol. 12, pp. 1001-1009.
Kemp et al., "Synthesis of Peptide-Functionalized Daicylaminoepinodolidiones," Tetrahedron Letters, 29:5077-5080 (1988).
Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.
Kettleborough et al., Humanization of a mouse monoclonal antibody by CDR-grafting: the importance of framework residues on loop conformation. Protein Eng. Oct. 1991;4(7):773-83.
Kido et al., "Kunitz-type Protease Found in Rat Mast Cells," J. Biol. Chem. 263(34): 18104-18107 (1988).
Kido et al., "Protease Specificity of Kunitz Inhibitor Domain of Alzheimer's Disease Amyloid Protein Precursor," Biochem Biophys Res Commun. Mar. 16, 1990;167(2):716-21.
Kirchhofer et al., "Hepsin activates pro-hepatocyte growth factor and is inhibited by hepatocyte growth factor activator-1B (HAI-1B) and HAI-2," Febs Letters, 2005, vol. 579, pp. 1945-1950.
Kirchhoff et al., "A Major Human Epididymis-Specific cDNA Encodes a Protein with Sequence Homology to Extracellular Proteinase Inhibitors," Biology of Reproduction, 45:350-357 (1991).

(56) References Cited

OTHER PUBLICATIONS

Kline et al. "Hirulog Peptides with Scissile Bond Replacements Resistant to Thrombin Cleavage," Biochem. Biophys. Res. Comm., 177:1049-1055 (1991).
Knappik et al., "Fully synthetic human combinatorial antibody libraries (HuCAL) based on modular consensus frameworks and CDRs randomized with trinucleotides", J. Mol. Biol. 296:57-86 (2000).
Ko et al., "Biotransformation of uridine monophosphate (UMP) and glucose to uridine diphosphate-glucose (UDPG) by Candida saitoana KCTC7249 cells." Appl Biochem Biotechnol.; 60(1):41-8 (Jul. 1996).
Kobayashi et al., "Amended structure of side chains in a cell wall mannan from Candida albicans serotype A strain grown in yeast extract—Sabouraud liquid medium under acidic conditions: detection of the branched side chains corresponding toantigenic factor 4.", FEMS Microbiol Lett.; 152(2):235-42 (Jul. 15, 1997).
Koizumi et al., Experimental studies of ischemic brain edema. 1. A new experimental model of cerebral embolism in rats in which recirculation can be introduced in the ischemic area. Jpn J Stroke 1986;8:1-8.
Kozyr et al., "Production of DNA-hydrolyzing antibody BV04-01 Fab fragment in methylotrophic yeast Pichia pastoris" Mol Biol (Mosk). Nov.-Dec. 2004;38(6):1067-75.
Krogh et al. "Hidden Markov models in computational biology. Applications to protein modeling." (1994) J. Mol. Biol. 235:1501-1531.
Kuno et al., "Possible involvement of neutrophil elastase in impaired mucosal repair in patients with ulcerative colitis," Journal of Gastroenterology, 2002, vol. 37, Supple XIV, pp. 22-32.
Kurjan et al., Structure of a yeast pheromone gene (MF alpha): a putative alpha-factor precursor contains four tandem copies of mature alpha-factor. Cell. Oct. 1982;30(3):933-43.
Lamminmaki et al., Crystal structure of a recombinant anti-estradiol Fab fragment in complex with 17beta-estradiol. J Biol Chem. Sep. 28, 2001;276(39):36687-94. Epub Jul. 12, 2001.
Laskowski et al., "Inhibitors with Class-Specific Reactive Sites," Ann. Rev. Biochem., 49:593-626 (1980).
Leatherbarrow et al., "Design of a Small Peptide-Based Proteinase Inhibitor by Modeling the Active-Site Region of Barley Chymotrypsin Inhibitor 2," Biochemistry, 30:10717-10721 (1991).
Lederman et al., A Single Amino Acid Substitution in a Common African Allele of the CD4 Molecule Ablates Binding of the Monoclonal Antibody, OKT4. Molecular Immunology. 1991;28(11):1171-1181.
Leeb-Lundberg et al. "International union of pharmacology. XLV. Classification of the kinin receptor family: from molecular mechanisms to pathophysiological consequences", (2005) Pharmacol Rev 57, 27-77.
Leonetti et al., "Increasing immunogenicity of antigens fused to Ig-binding proteins by cell surface targeting," The Journal of Immunology, 1998, vol. 160, pp. 3820-3827.
Levy et al., The therapeutic potential of a kallikrein inhibitor for treating hereditary angioedema. Expert Opin Investig Drugs. Sep. 2006;15(9):1077-90.
Ley et al., "Obtaining a Family of High-Affinity, High Specificity Protein Inhibitors of Plasmin and Plasma Kallikrein," Molecular Diversity, 2:119-124, (1996).
Li et al., B-Endorphin omission analogs: Dissociation of immunoreactivity from other biological activities. Proc. Natl. Acad. Sci. USA. Jun. 1980;77(6):3211-3214.
Lilla et al., "Active plasma kallikrein localizes to mast cells and regulates epithelial cell apoptosis, adipocyte differentiation, and stromal remodeling during mammary gland involution" J Biol Chem. 284(20):13792-13803 (2009).
Liu et al., Plasma kallikrein-kinin system and diabetic retinopathy. Biol Chem. Mar. 2013;394(3):319-28. doi: 10.1515/hsz-2012-0316. Author manuscript.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Lohmann et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993).
Longa et al., "Reversible middle cerebral artery occlusion without craniectomy in rats" Stroke 20 (1): 84-91 (1989).
Lucas et al., "The Binding of Human Plasminogen to Fibrin and Fibrinogen," J. Biol. Chem., 258:4249-4256 (1983).
Lumry et al., Interim Results of EDEMA2, A Multicenter, Open-Label, Repeat-Dosing Study of Intravenous and Subcutaneous Administration of Ecallantide (DX-88) in Hereditary Angioedema. J. Allergy and Clinical Immunology 117(2)(Suppl. 1):S179 Abstract699 (2006).
Lumry et al., Subcutaneous self-administration of lanadelumab for prophylactic treatment in patients with hereditary angioedema (HAE). Ann Allerg Asthma Im. Nov. 2018;121(5):S57.
MacCallum et al., Antibody-antigen interactions: contact analysis and binding site topography. J Mol Biol. Oct. 11, 1996;262(5):732-45.
MacGilchrist, "Effect of the Serine Protease Inhibitor, Aprotinin, on Systemic Haemodynamics and Renal Function in Patients with Hepatic Cirrhosis and Ascites," Clin. Sci., 87:329-335 (1994).
Magklara et al., "Characterization of the enzymatic activity of human kallikrein 6: autoactivation, substrate specificity and regulation by inhibitors," Biochem. Biophys. Res. Commun., Aug. 8, 2003, vol. 307, No. 4, pp. 948-955, Abstract Only.
Mann et al., Hemostasis and Thrombosis, Chapter 10, 2nd Edition, Basic Principles and Clinical Practice: 148-161 (1987).
Mannucci, "Hemostatic Drugs" New England Journal of Medicine, Drug Therapy, 339(4):245-253 (1998).
March, Advanced Organic Chemistry, 3rd Edition, Reactions, Mechanisms, and Structure, John Wiley and Sons, New York: 396-398; 1057-1060; 1099-1100 (1985).
Markland et al., "Iterative Optimization of High-Affinity Protease Inhibitors Using Phage Display. 1. Plasmin," Biochemistry, 35:8045-8057 (1996).
Markland et al., "Iterative Optimization of High-Affinity Protease Inhibitors Using Phage Display. 2. Plasma Kallikrein and Thrombin," Biochemistry 35(24):8058-67 (1996).
Markland et al., "Selection for Protease Inhibitors Using Bacteriophage Display," Methods Enzymol., 267:28-51 (1996).
Markland, Cell. Biochem. Supp., 1994, O, vol. 18D, p. 157, Abstract S 331.
Martin et al., "Animal models of neuropathic pain" Methods Mol Med. 84:233-42 (2003).
Mathews et al., Biochemistry, The Benjamin Cummins Publishing Co., Inc. Redwood City CA: 208-212 (1990).
Mattheakis et al. "An in vitro polysome display system for identifying ligands from very large peptide libraries" Proc. Natl. Acad. Sci. USA 91:9022 (1994).
Maxfield et al., "Conformation of poly(ethylene oxide) in the solid state, melt and solution measured by Raman scattering," Polymer, 1975, vol. 16, pp. 505-509.
Mayzel-Oreg, "Microsphere-induced embolic stroke: an MRI study" Magn Reson Med 51: 1232-8 (2004).
McCarty, "Crystal-induced inflammation of the joints," Annual Reviews of Medicine, vol. 21, pp. 357-366 (1970).
McConnell et al., "New Leupeptin Analogues: Synthesis and Inhibition Data," J. Med. Chem., 33:86-93 (1990).
Merriam-Webster reference for the term "prevent." web date: 2010. 2 pages.
Merrifield, "Solid Phase Peptide Synthesis. I. The Synthesis of a Tetrapeptide," Am. Chem. Soc. 85:2149-2154 (1963).
Migliore et al: "Open pilot study of ultrasound-guided intra-articular injection of hylan G-F 20 (Synvisc) in the treatment of symptomatic hip osteoarthritis", Clinical Rheumatology; Journal of the International League of Associations for Rheumatology, Springer-Verlag, LO, vol. 24, No. 3, pp. 285-289 (Jun. 1, 2005).

(56) References Cited

OTHER PUBLICATIONS

Mine et al., "Structural mechanism for heparin-binding of the third Kunitz domain of human tissue factor pathway inhibitor," Biochemistry, 2002, vol. 41, pp. 78-85.
Miyajima et al., Secretion of mature mouse interleukin-2 by *Saccharomyces cerevisiae*: use of a general secretion vector containing promoter and leader sequences of the mating pheromone alpha-factor. Gene. 1985;37(1-3):155-61.
Molineux, "Pegylation: engineering improved pharmaceuticals for enhanced therapy," Cancer Treatment Reviews, 2002, vol. 28, pp. 13-16.
Monteseirin et al., "Plasma Kallikrein Amidolytic Activity in Bronchial Asthma," Allergol. Immunopathol., (Madr)., 20:211-214 (1992).
Moreland, "Intra-articular hyaluronan (hyaluronic acid) and hylans for the treatment of osteoarthritis: mechanisms of action," Arthritis Res. Ther, 2003, vol. 5, pp. 54-67.
Morishita et al., "Novel factor Xa and plasma kallikrein inhibitory-activities of the second Kunitz-type inhibitory domain of urinary trypsin inhibitor" Thromb Res, 73(3-4): p. 193-204 (1994).
Morrison "Transfectomas provide novel chimeric antibodies." (1985) Science 229:1202-1207.
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Nadkarni et al., "Optimization of a mouse recombinant antibody fragment for efficient production from *Escherichia coli*" 2007 Protein Expr Purif 52(1):219-29.
Naess et al., "Effects of a Combined Drug Regimen on Tumour Necrosis Factor and Plasma Kallikrein Activity in Experimental Endotoxaemia," Eur. J. Surg., 160:77-86 (1994).
Nagai et al., Bicyclic turned dipeptide (BTD) as a β-turn mimetic; its design, synthesis and incorporation into bioactive peptides Tetrahedron, 49:3577-3592 (1993).
Nagai et al., Synthesis of a bicyclic dipeptide with the shape of β-turn central part. Tetrahedron Letters, 26 (5):647-650 (1985).
Needleman et al. "A general method applicable to the search for similarities in the amino acid sequences of two proteins" (1970) J. Mol. Biol. 48:444-453.
Nektartm—Transforming Therapeutics, Nektar Advanced PEGylation: Polyethylene Glycol and Derivatives for Advanced PEGylation, pp. 1-24, catalogue 2004.
Nektartm—Transforming Therapeutics, Nektar Molecule Engineering: Polyethylene Glycol and Derivatives for Advanced PEGylation, pp. 1-20, catalogue-2003.
Neuhaus et al., "Effect of Aprotinin on Intraoperative Bleeding and Fibrinolysis in Liver Transplantation," Lancet, 2: 924-925 (1989).
Ngo et al., "The protein folding problem and tertiary structure prediction, Chapter 14: Computational complexity protein structure prediction, and the Levinthal paradox," pp. 433-440 and 492-495 only (1994).
Ning et al., "Production of recombinant humanized anti-HBsAg Fab fragment from Pichia pastoris by fermentation.", J Biochem Mol Biol. ;38(3):294-9. (May 31, 2005).
Nof Corporation, "PEG Derivatives, Phospholipid and Drug Delivery Materials for Pharmaceutical Products and Formulations," pp. 1-59, catalogue Ver. 8—Apr. 2006.
Nof Corporation, "PEG Derivatives, Phospholipid and Drug Delivery Materials for Pharmaceuticals," pp. 1-46, catalogue—2003, 1st.
Nof Corporation, "PEG Derivatives, Phospholipid and Drug Delivery Materials for Pharmaceuticals," pp. 1-50, catalogue—2003 2nd.
Novotney et al., "Purification and Characterization of the Lipoprotein-associated Coagulation Inhibitor from Human Plasma," J. Biol. Chem. 264:18832-18837 (1989).
Nwariaku et al., "Effect of a bradykinin antagonist on the local inflammatory response following thermal injury" Burns, 22:324-327 (1996). (Abstract only).
Oi et al. "Chimeric Antibodies" (1986) BioTechniques 4:214.
Okamoto et al., "A Finding of Highly Selective Synthetic Inhibitor of Plasma Kallikrein; Its Action to Bradykinin Generation, Intrinsic Coagulation and Experimental DIC," Agents Actions Suppl., 38(I):198-205 (1992).
Okano et al., Chapter 9.1.2 Drug Action and Blood Concentration. Shin Yakuzaiaku Soron, revised 3rd Edition, Apr. 10, 1987:250-253.
O'Reilly et al., "Angiostatin: A Novel Angiogenesis Inhibitor That Mediates the Suppression of Metastases by a Lewis Lung Carcinoma," Cell, 79 317-328 (1994).
Padlan et al., Structure of an antibody-antigen complex: crystal structure of the HyHEL-10 Fab-lysozyme complex. Proc Natl Acad Sci U S A. Aug. 1989;86(15):5938-42.
Pan et al., "Reperfusion injury following cerebral ischemia: pathophysiology, MR imaging, and potential therapies," Neuroradiology, 2007, vol. 49, pp. 93-102.
Park et al., "Three Dimensional Structure of the Kringle Sequence: Structure of Prothrombin Fragment 1," Biochemistry, 25:3977-3982 (1986).
Paul. Fv Structure and Diversity in Three Dimensions. Fundamental Immunology, 3rd Edition. 1993: 292-5.
Peng, "Experimental use of murine lupus models" Methods Mol Med. 102:227-72 (2004).
Petersen et al., "Inhibitory properties of separate recombinant Kunitz-type-protease-inhibitor domains from tissue-factor-pathway inhibitor," Eur. J. Biochem., 1996, vol. 235, pp. 310-316.
Phillips, "The challenge of gene therapy and DNA delivery," J. Pharm. Pharmacology, vol. 53, pp. 1169-1174 (2001).
Phipps et al., Plasma kallikrein mediates angiotensin II type 1 receptor-stimulated retinal vascular permeability. Hypertension. Feb. 2009;53(2):175-81. doi:10.1161/HYPERTENSIONAHA.108.117663. Epub Jan. 5, 2009. With 5 page Online Supplement.
Pintigny et al., "Aprotinin can inhibit the proteolytic activity of thrombin: a fluorescence and an enzymatic study," Eur. J. Biochem., 1992, vol. 207, pp. 89-95.
Piro et al., "Role for the Kunitz-3 domain of tissue factor pathway inhibitor-a in cell surface binding," Circulation, 2004, vol. 110, pp. 3567-3572.
Pirollo et al., "Targeted delivery of small interfering RNA: approaching effective cancer therapies," Cancer Res., 2008, vol. 68, No. 5, pp. 1247-1250.
Pitt et al., Rabbit monoarticular arthritis as a model for intra-articular drug injections. The local action of administered cortisol and alpha-1 proteinase inhibitor. Agents Actions. Dec. 1984;15(5-6):541-8.
Polypure, Products; PEG amines; PEG acids and amino acids, PEG thils and disulfides; Biotins, Apr. 2005.
Polypure, Products; PEG amines; PEG acids and amino acids; PEG thiols and disulfides; Biotins, Apr. 2004.
Powers et al., "Expression of Single-Chain Fv-Fc Fusions in Pichia pastoris", J. Immunol. Methods. 251:123-35 (2001).
Poznansky et al., "Growth hormone-albumin-conjugates reduced renal toxicity and altered plasma clearance," 1988, vol. 239, pp. 18-22.
Putterman, "Aprotinin Therapy in Septic Shock," ACTA Chir. Scand., 155:367 (1989).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse discrete PEGTM (dPEGTM) derivatives, Product Catalogue, pp. 1-51, Updated: Nov. 17, 2005.
Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Raspi, Kallikrein and kallikrein-like proteinases: purification and determination by chromatographic and electrophoretic methods. J Chromatogr B Biomed Appl. Sep. 20, 1996;684(1-2):265-87.

(56) References Cited

OTHER PUBLICATIONS

Reginato et al., "Genetics and experimental models of crystal-induced arthritis. Lessons learned from mice and men: is it crystal clear?" Curr Opin Rheumatol. 19(2):134-45 (2007).
Reichert, "Technology evaluation: lumiliximab, Biogen Idec" Curr Opin Mol Ther., 6(6):675-83 (2004). (Abstract only).
Ren et al., "Inflammatory Models of Pain and Hyperalgesia" Ilar J. 40(3): 111-118 (1999).
Riedl et al., An open-label study to evaluate the long-term safety and efficacy of lanadelumab for prevention of attacks in hereditary angioedema: design of the HELP study extension. Clin Transl Allergy. Oct. 6, 2017;7:36. doi: 10.1186/s13601-017-0172-9.
Robbins et al., Hemostasis and Thrombosis, Chapter 21, 2nd Edition, Basic Principles and Clinical Practice: 340-357 (1987).
Roberts et al., "Chemistry for peptide and protein PEGylation", Advanced Drug Delivery Reviews, 54, pp. 459-476, 2002.
Roberts et al., "Directed evolution of a protein: selection of potent neutrophil elastase inhibitor displayed on M13 fusion phage," PNAS USA, vol. 89, pp. 2429-2433 (1992).
Roberts et al., "Protease inhibitor display M13 phage: selection of high-affinity neutrophil elastase inhibitors," Gene, vol. 121, pp. 9-15 (1992).
Rossi et al., The Synthetic Peptide DX88 Binds to Endothelial Cells In Vitro and Retains the Inhibitory Activity on Kallikrein, International Immunopharmacology 2(9):1313, Abstract 142 (2002).
Rudikoff et al., Single amino acid substitution altering antigen-binding specificity. Proc Natl Acad Sci U S A. Mar. 1982;79(6):1979-83.
Sainz et al., "Fifty years of research on the plasma kallikrein-kinin system: from protein structure and function to cell biology and in-vivo pathophysiology" Thromb Haemost 98, 77-83, 2007.
Sartor et al., "Selective Kallikrein-Kinin System Activation in Inbred Rats Differentially Susceptible to Granulomatous Enterocolitis," Gastroenterology, 110:1467-1481 (1996).
Scarff et al., "Targeted disruption of SP13/Serpinb6 does not result in development of growth defects, leukocyte dysfunction, or susceptibility to stroke," Molecular and Cellular Biology, May 2004, pp. 4075-4082.
Scatchard, The Attractions of Proteins for Small Molecules and Ions, Ann. NY Acad. Sci, 51:660-672 (1949).
Schaffirzel et al., "Ribosome display: an in vitro method for selection and evolution of antibodies from libraries" J Immunol Methods. 231(1-2):119-35 (1999).
Schechter et al., On the Active Site of Proteases, III Mapping the Active Site of Papain; Specific Peptide Inhibitors of Papain, Biochemical and Biophysical Research Communications 32(5):898-902 (1968).
Schechter et al., On the Size of the Active Site on Proteases, I Papain, Biochemical and Biophysical Research Communications 27(2):157-162 (1967).
Schmaier et al., Hemostasis and Thrombosis, Chapter 2, 2nd Edition, Basic Principals and Clinical Practice: 18-38 (1987).
Schmaier, "Assembly, activation, and physiologic influence of the plasma kallikrein/kinin system" (2008) Int Immunopharmaco18, 161-165. Author manuscript.
Schmid-Elsaesser et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70(1989).
Schmidt et al., "A male accessory gland peptide with protease inhibitory activity in *Drosophila funebris*," J Biol Chem. Jun. 15, 1989;264(17):9745-9.
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.
Schofield et al., "Monoclonal antibodies that neutralize HEV recognize an antigenic site at the carboxyterminus of an ORF2 protein vaccine" Vaccine (2003) 22(2):257-67.
Schoonbroodt et al., Human antibodies selected by phage display as potent and selective protease inhibitors. Human Antibodies. 2007;16(1-2):18-22.
Schoonooghe et al., "Efficient production of human bivalent and trivalent anti-MUC1 Fab-scFv antibodies in Pichia pastoris", BMC Biotechnol. Aug. 11, 2009;9:70.
Schopf, "IDEC-114 (IDEC)" Curr Opin Investig Drugs, 2(5):635-8 (2001). (Abstact only).
Schultz et al. "SMART, a simple modular architecture research tool: identification of signaling domains" (1998) Proc. Natl. Acad. Sci. USA 95:5857-5864.
Schultz et al., "SMART: a web-based tool for the study of genetically mobile domains" (2000) Nucl. Acids Res 28:231-234.
Schwartz et al., "Stability studies on derivatives of the bovine trypsin inhibitor," Biochemistry, vol. 26, pp. 3544-3551 (1987).
Sekiguchi et al., "Experimental spinal stenosis: relationship between degree of cauda equina compression, neuropathology, and pain" Spine 29, 1105-1111 (2004)).
Sela-Culang et al., The structural basis of antibody-antigen recognition. Front Immunol. Oct. 8, 2013;4:302. doi: 10.3389/fimmu.2013.00302.
Sexton et al., Comparison of Plasma Kallikrein Inhibition by the Endogenous C1-Inhibitor Versus DX-2930, a Monoclonal Antibody Inhibitor. Blood. 2013; 122:1066. Abstract only.
Sexton et al., Discovery and characterization of fully human monoclonal antibody inhibitor of plasma kallikrein for the treatment of plasma kallikrein-mediated edema. J Allergy Clin Immunol. Feb. 2013;131(2):AB32. Suppl S. Annual meeting of the American Academy of Allergy, Asthma, and Immunology. San Antonio, TX, USA; Feb. 22-26.
Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.
Shariat-Madar et al., Assembly and activation of the plasma kallikrein/kinin system: a new interpretation. Int Immunopharmacol. Dec. 2002;2(13-14):1841-9.
Sharma et al., "The kinin antagonist hoe 140 reduces acute paw oedema in rats caused by carrageenan, bradykinin and kaolin" Inflammopharmacology 6,9-17 (1998).
Shearwater Corporation, Polyethylene Glycol and Derivatives for Biomedical Applications, pp. 1-17, catalogue—2001.
Shearwater Polymers, Inc., Polyethylene Glycol and Derivatives, pp. 1-50, catalogue—Jul. 1997.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.
Sheppard et al., Acid-Labile Resin Linkage Agents for Use in Solid Phase Peptide Synthesis, Int. J. Peptide Protein Res., 20:451-454 (1982).
Sheridan et al., A Multicenter Trial of the Use of the Proteolytic Enzyme Inhibitor Aprotinin in Colorectal Surgery, Dis. Colon Rectum, 32:505-508 (1989).
Shibuya et al., "Primary Structure of Guinea Pig Plasma Prekallikrein", Immunopharmacology, vol. 45 (1-3), p. 127-134, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Silverberg et al. "The Contact System and Its Disorders," in Blood: Principles and Practice of Hematology, Handin R. et al., eds. J B. Lippincott Co., Philadelphia, (1995).
Singer et al., "A porcine burn model" Methods Mol Med. 78: 107-19 (2003).
Skolnick et al., "From genes to protein structure and function: novel applications of computational approaches in the genomic era," Trends in Biotech., 2000, vol. 18, No. 1, pp. 34-39.
Slootstra et al., "Structural aspects of antibody-antigen interaction revealed through small random peptide libraries", Molecular Diversity,1, 87-96 (1996).

(56) References Cited

OTHER PUBLICATIONS

Smith et al. "Prolonged in vivo residence times of antibody fragments associated with albumin" Bioconjug Chem 12(5):750-756 (2001).
Smith, "Filamentous fusion phage: novel expression vectors that display cloned antigens on the virion surface" Science 228:1315-1317 (1985).
Sonhammer et al., "Pfam: a comprehensive database of protein domain families based on seed alignments" (1997) Proteins 28(3):405-420.
Sonis et al., "An animal model for mucositis induced by cancer chemotherapy" (1990) Oral Surg Oral Med Oral Pathol. 69:437-43.
Sonis et al., "Validation of a new scoring system for the assessment of clinical trial research of oral mucositis induced by radiation or chemotherapy. Mucositis Study Group." (1999) Cancer 85:2103-13.
Sprecher et al., "Molecular Cloning, Expression, and Partial Characterization of a Second Human Tissue-Factor-Pathway Inhibitor," Proc. Natl. Acad. Sci. USA, 91:3353-3357 (1994).
Stadnicki et al., "Activation of plasma contact and coagulation systems and neutrophils in the active phase of ulcerative colitis," Digestive Diseases and Sciences, 1997, vol. 42, No. 1, pp. 2356-2366.
Stadnicki et al., "Activation of the contact system and circulating neutrophil elastase in ulcerative colitis patients" 10th World Congress of Gastroenterology, p. 1166, 1994.
Stadnicki et al., "Activation of the Kallikrein-Kinin System in Indomethacin-Induced Entercolitis in Genetically Susceptible Rats," J. Invest. Med., 44:299A (1996).
Stadnicki et al., "Selective Plasma Kallikrein Inhibitor Attenuates Acute Intestinal Inflammation in Lewis Rat," Dig. Dis. Sci., 41:912-920 (1996).
Stevenson et al., "A mouse model of burn wounding and sepsis" Methods Mol Med. 78:95-105 (2003).
Stewart et al., Solid-Phase Peptide Synthesis (W.H. Freeman Co., San Francisco 1989). 6 pages.
Stultz et al., "Structural analysis based on state-space modeling." Protein Sci. 2:305-314 (1993).
Sunkureddi et al., "Clinical signs of gout," Hospital Physician, 2006, pp. 39-41. Retrieved from the internet <http://citeseerx.ist.psu.edu/viewdoc/download?doi=10.1.1.643.7808&rep=rep1&type=pdf> on Aug. 1, 2018.
Taby et al., "Inhibition of activated protein C by aprotinin and the uses of the insolubilized inhibitor for its purification," Thrombosis Research, 1990, vol. 59, pp. 27-35.
Taggart et al., "Inactivation of human-b-defensins 2 and 3 by elastolytic cathepsins1," The Journal of Immunology, 2003, vol. 170, pp. 931-937.
Takahashi et al., "Production of humanized Fab fragment against human high affinity IgE receptor in Pichia pastoris" Biosci Biotechnol Biochem 64(10):2138-44 (2000).
Tamura et al., "Focal cerebral ischaemia in the rat: 1. Description of technique and early neuropathological consequences following middle cerebral artery occlusion" J Cereb Blood Flow Metab 1: 53-60 (1981).
Tanaka et al. "A novel rat model of abdominal aortic aneurysm using a combination of intraluminal elastase infusion and extraluminal calcium chloride exposure" J Vasc Surg. 50(6):1423-32 (2009).
Tang et al., Expression, crystallization, and three-dimensional structure of the catalytic domain of human plasma kallikrein. J Biol Chem. Dec. 9, 2005;280(49):41077-89. Epub Sep. 3, 20050.
The Merck Index, 11th edition, 1989. pp. 145, 146, 263, 427, 428, 1183, and 1184. 9 pages.
Tian et al., Synthesis of optically pure C alpha-methyl-arginine. Int J Pept Protein Res. Aug. 1992;40(2):119-26.
Timmerman et al., "Functional reconstruction and synthetic mimicry of a conformational epitope using Clips Tm technology" J. Mol. Recognit. 20:283-99 (2007).
Tomlinson et al. "Structural repertoire of the human Vk domain" EMBO J. 14(18):4628-3 (1995).
Tomlinson et al. "The repertoire of human germline VH sequences reveals about 50 groups of VH segments with different hypervariable loops" J. Mol. Biol. 227:776-798 (1992).
Travis et al., "Pulmonary perspective: potential problems in designing elastase inhibitors for therapy," Am. Rev. Respir. Dig., 1991, vol. 143, pp. 1412-1415.
Tremblay et al., "Anti-inflammatory activity of neutrophil elastase inhibitors," Current Opinion in Investigational Drugs, 2003, vol. 4, No. 5, pp. 556-565.
Tschesche et al., "Semisynthetic engineering of proteinase inhibitor homologues," Biochim. Biophys. Acta, vol. 913, pp. 97-101 (1987).
Uebel, Die Behandlung von Kniegelenksarthrosen mit Trasylol [The treatment of arthroses of the knee joint with Trasylol]. Langenbacks Arch. Chir., vol. 325, pp. 356-358 (1969).
Urlaub et al., "Isolation of Chinese hamster cell mutants deficient in dihydrofolate reductase activity", Proc. Natl. Acad. Sci. USA 77:4216-4220 (1980).
Vajdos et al., Comprehensive functional maps of the antigen-binding site of an anti-ErbB2 antibody obtained with shotgun scanning mutagenesis. J Mol Biol. Jul. 5, 2002;320(2):415-28.
Van Der Logt et al., "Intron-Exon Organization of the Human Gene Coding for the Lipoprotein-associated Coagulation Inhibitor: The Factor Xa Dependent of Inhibitor of the Extrinsic Pathway of Coagulation," Biochemistry, 30:1571-1577 (1991).
Van Dijl et al., "Signal Peptidase 1 of Bacillus subtillis: Patterns of Conserved Amino Acids in Prokaryotic and Eukaryotic Type 1 Signal Peptidases," The EMBO Journal, 11:2819-2828 (1992).
Varadi et al., "Location of Plasminogen-Binding Sites in Human Fibrin(ogen)," Biochemistry, 22:2440-2446 (1983).
Varadi et al., Segment of Fibrinogen Is in a Region Essential for Plasminogen Binding by Fibrin Fragment E, Biochemistry, 23:2108-2112 (1984).
Vedvick et al., "High-Level Secretion of Biologically Active Aprotinin from the Yeast Pichia pastoris," J. Ind. Microbiol., 7:197-201 (1991).
Veloso et al., A monoclonal anti-human plasma prekallikrein antibody that inhibits activation of prekallikrein by factor XIIa on a surface. Blood. Oct. 1987;70(4):1053-62.
Veronese, "Peptide and protein PEGylation: a review of problems and solutions," Biomaterials, Mar. 1, 2001, vol. 22, No. 5, pp. 405-417.
Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.
Vidal et al., "Making sense of antisense," European Journal of Cancer, 2005, vol. 41, pp. 2812-2818.
Viswanathan et al., "Engineered protein protease inhibitors", Current Enzyme Inhibition, Jan. 1, 2009, pp. 87-98, vol. 5, No. 2, Betham Science Publishers Ltd., Hilversum, NL.
Volpe-Junior et al., "Augmented plasma and tissue kallikrein like activity in synovial fluid of patients with inflammatory articular diseases," Inflamm. Res., 1996, vol. 45, pp. 198-202.
Wade et al., Solid-phase synthesis of alpha-human atrial natriuretic factor: comparison of the Boc-polystyrene and Fmoc-polyamide methods. Biopolymers. 1986;25 Suppl:S21-37.
Wagner et al., High level expression, purification, and characterization of the Kunitz-type protease inhibitor domain of protease nexin-2/amyloid beta-protein precursor. Biochem Biophys Res Commun. Jul. 31, 1992;186(2):1138-45.
Walpole et al., The weight of nations: an estimation of adult human biomass. BMC Public Health. Jun. 18, 2012;12:439. doi: 10.1186/1471-2458-12-439.
Wang et al., "Monitoring of heparin-induced anticoagulation with kaolin-activated clotting time in cardiac surgical patients treated with aprotinin," Anesthesiology, vol. 77, pp. 1080-1084 (1992).
Wang et al., Antibody structure, instability, and formulation. J Pharm Sci. Jan. 2007;96(1):1-26. doi: 10.1002/jps.20727.
Ward et al. "Binding activities of a repertoire of single immunoglobulin variable domains secreted from *Escherichia coli*" (1989) Nature 341:544-546.

(56) References Cited

OTHER PUBLICATIONS

Wark et al., Latest technologies for the enhancement of antibody affinity. Adv Drug Deliv Rev. Aug. 7, 2006;58(5-6):657-70. Epub May 22, 2006.
Wark, "DX-890 (Dyax)", iDrugs, 5, pp. 586-589, Jun. 2002.
Watson et al., "Induction of reproducible brain infarction by photochemically initiated thrombosis" Ann Neurol17: 497-504 (1985).
Weaver, Animal studies paint misleading picture. Nature International Weekly Journal of Science. Published online Mar. 30, 2010. Retrieved on Aug. 1, 2017 from http://www.nature.com/news.2010.158.html.
Wedi, Lanadelumab to treat hereditary angioedema. Drugs Today (Barc). 2019.
Wedner et al., Modeling and Analyses to Identify Potential Dosing Regimens of DX-2930 for the Long-Term Prophylaxis of Hereditary Angioedema. J All Clin Immunol. Feb. 1, 2016;137(2):AB252.
Wei et al., "Production and characterization of ectoine by *Marinococcus* sp. ECT1 isolated from a high-salinity environment." J Biosci Bioeng. Mar. 2011;111(3):336-42. Epub Dec. 15, 2010.
Wellington et al., "Tranexamic Acid: A review of its use in the management of menorrhagia", Drugs, vol. 63, No. 13, pp. 1417-1433, 2003.
Wells, "Addivity of Mutational Effects in Proteins", Biochemistry, vol. 29 (37), pp. 8509-8517 (1990).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Williams et al. "Collagen-induced arthritis as a model for rheumatoid arthritis" Methods Mol Med. 98:207-16 (2004).
Wilson et al., "An animal model of chronic inflammatory pain: pharmacological and temporal differentiation from acute models" Eur J Pain. 10(6):537-49 (2006).
Wilson et al., "The Calculation and Synthesis of a Template Molecule," Tetrahedron, 49:3655-3663 (1993).
Wood, "Hemostatic Drugs" New England Journal of Medicine, Drug Therapy, 339(4):245-253 (1998).
Worthy et al., Kallikreins and kinins: mediators in inflammatory joint disease? Int J Exp Pathol. Aug. 1990;71(4):587-601.
Wu et al., Humanization of a murine monoclonal antibody by simultaneous optimization of framework and CDR residues. J Mol Biol. Nov. 19, 1999;294(1):151-62.
Wu, Lanadelumab for the treatment of hereditary angioedema. Expert Opin Biol Ther. Dec. 2019; 19(12):1233-1245. doi: 10.1080/14712598.2019.1685490. Epub Nov. 4, 2019.
Wun et al., "Cloning and Characterization of a cDNA Coding for the Lipoprotein-associated Coagulation Inhibitor Shows that it Consists of Three Tandem Kunitz-type Inhibitory Domains," J. Biol. Chem. 263:6001-6004 (1988).
Yetkin et al., "The healing effect of TGF-[alpha] on gastric ulcer induced by acetylsalicylic acid in rats", International Journal of Pharmaceutics, vol. 277, No. 1-2, Jun. 1, 2004, pp. 163-172.
Zuraw et al., "Clinical practice. Hereditary angioedema" N Engl J Med 359, 1027-1036, (2008).
Zuraw, Hae therapies: past present and future. Allergy Asthma Clin Immunol. Jul. 28, 2010;6(1):23. doi: 10.1186/1710-1492-6-23.
U.S. Appl. No. 16/199,453, filed Nov. 26, 2018, Nixon et al.
U.S. Appl. No. 16/445,304, filed Jun. 19, 2019, Sexton et al.
U.S. Appl. No. 16/411,242, filed May 14, 2019, Sexton et al.
U.S. Appl. No. 17/010,354, filed Sep. 2, 2020, Sexton et al.
U.S. Appl. No. 17/345,033, filed Jun. 11, 2021, Conley et al.
U.S. Appl. No. 16/061,103, filed Jun. 11, 2018, Adelman et al.
U.S. Appl. No. 17/672,748, filed Feb. 16, 2022, Adelman et al.
U.S. Appl. No. 16/556,524, filed Aug. 30, 2019, Lu et al.
U.S. Appl. No. 16/817,671, filed Mar. 13, 2020, Mendivil Medina.
PCT/US2016/024921, Jun. 30, 2016, International Search Report and Written Opinion.
PCT/US2016/024921, Oct. 12, 2017, International Preliminary Report on Patentability.
EP 16774069.5, Jul. 19, 2018, Partial Supplementary European Search Report.
EP 16774069.5, Oct. 26, 2018, Supplementary European Search Report.
EP 21167802.4, Oct. 29, 2021, Extended European Search Report.
[No Author Listed], Health Canada has authorized TAKHZYRO(TM) (lanadelumab injection), a first-of-its-kind monoclonal antibody treatment for the prevention of hereditary angioedema (HAE) attacks. Takeda. Sep. 20, 2018. https://www.takeda.com/newsroom/shire-news-releases/2018/fv80a5/ [last accessed Oct. 16, 2023]. 10 pages.
[No Author Listed], Prescribing Information for TAKHZYRO(TM). FDA. Aug. 24, 2018. https://www.accessdata.fda.gov/drugsatfda_docs/label/2018/761090s000lbl.pdf [last accessed Oct. 16, 2023]. 20 pages.
Abdel-Magid A.F., Plasma Kallikrein Inhibitors as Potential Treatment for Diabetic Macular Edema, Retinal Vein Occlusion, Hereditary Angioedema and Other Related Diseases. ACS Med Chem Lett. Jan. 17, 2023;14(2):129-130. doi: 10.1021/acsmedchemlett.2c00526.
Bowen et al., 2010 International consensus algorithm for the diagnosis, therapy and management of hereditary angioedema. Allergy Asthma Clin Immunol. Jul. 28, 2010;6(1):24(1-13). doi: 10.1186/1710-1492-6-24.
Chyung et al., P289: Pharmacologic Modeling to Guide the DX-2930 Dosing Regimen in Investigating Long-Term Prophylaxis of Hereditary Angioedema. Ann Allergy Asthma Immunol. Nov. 2014;113(5):A106.
Frank et al., Management of Children With Hereditary Angioedema Due to C1 Inhibitor Deficiency. Pediatrics. Nov. 2016;138(5):e20160575(1-11). doi: 10.1542/peds.2016-0575.
Kenniston et al., Discovery and Characterization of a Highly Specific Antibody Inhibitor of Plasma Kallikrein. Blood 2013;122:1067. Abstract only.
MacGinnitie AJ. Pediatric hereditary angioedema. Pediatr Allergy Immunol. Aug. 2014;25(5):420-7. doi: 10.1111/pai.12168. Epub Dec. 9, 2013.
Mould et al., Pharmacokinetics and pharmacodynamics of monoclonal antibodies: concepts and lessons for drug development. BioDrugs. Feb. 1, 2010;24(1):23-39. doi: 10.2165/11530560-000000000-00000.
Palm et al., The Importance of the Concentration-Temperature-Viscosity Relationship for the Development of Biologics. BioProcess International. Mar. 10, 2015. https://bioprocessintl.com/manufacturing/monoclonal-antibodies/importance-concentration-temperature-viscosity-relationship-development-biologics/ [last accessed Mar. 2, 2022]. 7 pages.
Riedl et al., 322: Attack-free status of patients with hereditary angioedema (HAE) during extended treatment with lanadelumab in the HELP OLE study. Journal of Allergy and Clinical Immunology. Feb. 1, 2020;145(2):AB104.
Riedl et al., Lanadelumab demonstrates rapid and sustained prevention of hereditary angioedema attacks. Allergy. Nov. 2020;75(11):2879-2887. doi: 10.1111/all.14416. Epub Jul. 6, 2020.
Tinning et al., Make your Best Guess: an updated method for paediatric weight estimation in emergencies. Emerg Med Australas. Dec. 2007;19(6):528-34. doi: 10.1111/j.1742-6723.2007.01026.x.
[No Author Listed], DX-2930, A New Drug for Hereditary Angioedema, Received Breakthrough Pharmaceutical Qualification From FDA. Journal of Guangdong Pharmaceutical University. Aug. 25, 2015;31:534. Source: BioValley Jul. 8, 2015.
Yao et al., Progress in the Research of Prophylaxis and Treatment for Hereditary Angioedema. J Diagn Ther Dermato-Venereol. Feb. 28, 2018;25(1):53-6.
Zuraw et al., Lanadelumab Exposure During Steady State: Achievement of Effective Concentrations in Patients in the HELP Study. Poster. American College of Asthma, Allergy & Immunology Annual Scientific Meeting. Seattle, WA. Nov. 2018.
[No Author Listed], Efficacy and Safety Study of DX-2930 to Prevent Acute Angioedema Attacks in Patients with Type I and Type II HAE. Study NCT02586805. ClinicalTrials.gov Oct. 26, 2015. 7pgs.

(56) References Cited

OTHER PUBLICATIONS

[No Author Listed], Long-term Safety and Efficacy Study of DX-2930 (SHP643) to Prevent Acute Angioedema Attacks in Patients With Type I and Type II HAE. NCT02741596. U.S. National Library of Medicine, ClinicalTrials.gov. Version 12: May 25, 2018. (Version 1 posted Apr. 15, 2016). https://clinicaltrials.gov/study/NCT02741596#more-information. 15 pages.
Boyles, Novel Kallikrein Inhibitor Promising for HAE Prophylaxis, MedPage Today. Feb. 22, 2017. https://www.medpagetoday.com/pulmonology/generalpulmonary/63342.
Iaboni et al., Impact of lanadelumab in hereditary angioedema: a case series of 12 patients in Canada. Allergy Asthma & Clin Immunol. Jul. 23, 2021;17(1):78.
Ruggieri et al., Successful private-public funding of paediatric medicines research: lessons from the EU programme to fund research into off-patent medicines. Eur J Pediatr. Apr. 2015;174(4):481-91. doi: 10.1007/s00431-014-2398-z. Epub Sep. 23, 2014.
Tachdjian et al., Lanadelumab efficacy after switching from placebo: results from the HELP and HELP open-label extension studies. Ann Allergy Asthma Immunol. Nov. 2018;121(5):S38.
[No Author Listed], ClinicalTrials.gov Identifier: NCT02093923. A Double-Blind, Multiple Ascending Dose Study to Assess Safety, Tolerability and Pharmacokinetics of DX-2930 in Hereditary Angioedema Participants. Oct. 16, 2014. https://clinicaltriais.gov/ct2/show/NCT62093923 [last accessed Sep. 10, 2025]. 5 pages.
[No Author Listed], Creatine Kinase (CK). Cleveland Clinic. Last accessed from: https://my.clevelandclinic.org/health/diagnostics/22692-creatine-kinase-ck on Sep. 17, 2024. 13 pages.
[No Author Listed], Creatine Phosphokinase (CPK). Johns Hopkins Lupus Center. Last accessed from: https://www.hopkinslupus.org/lupus-tests/clinical-tests/creatine-phosphokinase-cpk/ on Jul. 25, 2025. 1 page.
[No Author Listed], HAE International, "Dyax presents Phase 1b data for DX-2930" dated Jun. 8, 2015. Last accessed from: https://haei.org/fa/dyax-presents/ on Jun. 27, 2025. 3 pages.
[No Author Listed], Prescribing Information for TAKHZYRO(TM). FDA. Feb. 3, 2023. Reference ID: 5120543. https://www.accessdata.fda.gov/drugsatfda_docs/label/2023/761090s010lbl.pdf [last accessed Aug. 18, 2025]. 21 pages.
[No Author Listed], What is Hereditary Angioedema (HAE)? The US Hereditary Angioedema Association (HAEA). Last accessed from: https://www.haea.org/pages/p/what_is_hae on Jul. 25, 2025. 4 pages.
Bygum et al., Disease Severity, Activity, Impact, and Control and How to Assess Them in Patients with Hereditary Angioedema. Front Med (Lausanne). Dec. 4, 2017;4:212. doi: 10.3389/fmed.2017.00212.
Dai et al., Role of Bradykinin in the Pathogenesis of Allergic Diseases. Chin J Allergy Clin Immunol. Dec. 30, 2014;8(4):306-11.
Kokoye et al., A Comparison of the Effects of Factor XII Deficiency and Prekallikrein Deficiency on Thrombus Formation. Thromb Res. Apr. 2016;140:118-124. doi: 10.1016/j.thromres.2016.02.020. Epub Feb. 18, 2016. Author Manuscript, 19 pages.
Maurer et al. Lanadelumab in Patients 2 to Less Than 12 Years Old With Hereditary Angioedema: Results From the Phase 3 SPRING Study. J Allergy Clin Immunol Pract. Jan. 2024;12(1):201-11.e6. doi: 10.1016/j.jaip.2023.09.009. Epub Sep. 18, 2023.
Torzewski et al., Animal Models of C-Reactive Protein. Mediators Inflamm. 2014; 2014:683598. doi: 10.1155/2014/683598. Epub Apr. 24, 2014.
Van Der Vekens et al., Human and equine cardiovascular endocrinology: beware to compare. Cardiovascular Endocrinology. Dec. 2013; 2(4):67-76. doi: 10.1097/XCE.0000000000000009.
Khayat et al., Animal Models of Retinal Vein Occlusion. Invest Ophthalmol Vis Sci. Dec. 1, 2017;58(14):6175-6192. doi: 10.1167/iovs.17-22788.
Lambert et al., Laser-induced choroidal neovascularization model to study age-related macular degeneration in mice. Nat Protoc. Nov. 2013;8(11):2197-211. doi: 10.1038/nprot.2013.135. Epub Oct. 17, 2013.
Luyt et al., Virus-induced acute respiratory distress syndrome: epidemiology, management and outcome. Presse Med. Dec. 2011;40(12 Pt 2):e561-8. doi: 10.1016/j.lpm.2011.05.027. Epub Nov. 16, 2011.
Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.
Reyns et al., Selection Strategy of In Vivo Models for Ophthalmic Drug Development in Diabetic Retinopathy. J Mol Genet Med. 2016;10(1):1000202. doi: 10.4172/1747-0862.1000202. 18 pages.
Shah et al., A Mouse Model for Laser-induced Choroidal Neovascularization. J Vis Exp. Dec. 27, 2015;(106):e53502. doi: 10.3791/53502.
Sun et al., Why 90% of clinical drug development fails and how to improve it? Acta Pharm Sin B. Jul. 2022;12(7):3049-3062. doi: 10.1016/j.apsb.2022.02.002. Epub Feb. 11, 2022.

A.

B.

A.

B.

C.

D.

E.

F.

SEQUENCE LISTING

```
<160> NUMBER OF SEQ ID NOS: 12

<210> SEQ ID NO 1
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 1

Met Gly Trp Ser Cys Ile Leu Phe Leu Val Ala Thr Ala Thr Gly Ala
1               5                   10                  15
```

-continued

```
His Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Phe Thr Phe Ser
        35                  40                  45

His Tyr Ile Met Met Trp Val Arg Gln Ala Pro Gly Lys Gly Leu Glu
    50                  55                  60

Trp Val Ser Gly Ile Tyr Ser Ser Gly Gly Ile Thr Val Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Tyr Arg Arg Ile Gly Val Pro Arg Arg Asp Glu Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430
```

```
Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465


<210> SEQ ID NO 2
<211> LENGTH: 231
<212> TYPE: PRT
<213> ORGANISM: Artificial Sequence
<220> FEATURE:
<223> OTHER INFORMATION: Synthetic Polypeptide

<400> SEQUENCE: 2

Met Gly Trp Ser Cys Ile Leu Phe Leu Val Ala Thr Ala Thr Gly Ala
1               5                   10                  15

His Ser Asp Ile Gln Met Thr Gln Ser Pro Ser Thr Leu Ser Ala Ser
            20                  25                  30

Val Gly Asp Arg Val Thr Ile Thr Cys Arg Ala Ser Gln Ser Ile Ser
        35                  40                  45

Ser Trp Leu Ala Trp Tyr Gln Gln Lys Pro Gly Lys Ala Pro Lys Leu
    50                  55                  60

Leu Ile Tyr Lys Ala Ser Thr Leu Glu Ser Gly Val Pro Ser Arg Phe
65                  70                  75                  80

Ser Gly Ser Gly Ser Gly Thr Glu Phe Thr Leu Thr Ile Ser Ser Leu
                85                  90                  95

Gln Pro Asp Asp Phe Ala Thr Tyr Tyr Cys Gln Gln Tyr Asn Thr Tyr
            100                 105                 110

Trp Thr Phe Gly Gln Gly Thr Lys Val Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205

Tyr Ala Cys Glu Val Thr His Gln Gly Leu Ser Ser Pro Val Thr Lys
    210                 215                 220

Ser Phe Asn Arg Gly Glu Cys
225                 230


<210> SEQ ID NO 3
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30
```

```
Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110

Gly Gln Gly Thr Met Val Thr Val Ser Ser
        115                 120


<210> SEQ ID NO 4
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys
            100                 105


<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

His Tyr Ile Met Met
1               5


<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Gly Ile Tyr Ser Ser Gly Gly Ile Thr Val Tyr Ala Asp Ser Val Lys
1               5                   10                  15

Gly
```

<210> SEQ ID NO 7
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 7

```
Arg Arg Ile Gly Val Pro Arg Arg Asp Glu Phe Asp Ile
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 8

```
Arg Ala Ser Gln Ser Ile Ser Ser Trp Leu Ala
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

```
Lys Ala Ser Thr Leu Glu Ser
1               5
```

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 10

```
Gln Gln Tyr Asn Thr Tyr Trp Thr
1               5
```

<210> SEQ ID NO 11
<211> LENGTH: 451
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Tyr Arg Arg Ile Gly Val Pro Arg Arg Asp Glu Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 12
<211> LENGTH: 213
<212> TYPE: PRT
<213> ORGANISM: Artificial Sequence
<220> FEATURE:
<223> OTHER INFORMATION: Synthetic

<400> SEQUENCE: 12

-continued

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

METHOD FOR PREVENTING HEREDITARY ANGIOEDEMA ATTACK

RELATED APPLICATIONS

This application is a continuation of U.S. application Ser. No. 15/562,671, filed Sep. 28, 2017, which is a national stage filing under 35 U.S.C. § 371 of international application number PCT/US2016/024921, filed Mar. 30, 2016, which was published under PCT Article 21(2) in English and claims the benefit under 35 U.S.C. § 119(e) of U.S. provisional application No. 62/140,277, filed Mar. 30, 2015, U.S. provisional application No. 62/214,293, filed Sep. 4, 2015 and U.S. provisional application No. 62/140,289, filed Mar. 30, 2015, the contents of each of which are herein incorporated by reference in its entirety.

REFERENCE TO AN ELECTRONIC SEQUENCE LISTING

The contents of the electronic sequence listing (D061770107US03-SUBSEQ-EMB.txt; Size: 15,996 bytes; and Date of Creation: May 9, 2024) is herein incorporated by reference in its entirety.

BACKGROUND

Plasma kallikrein is a serine protease component of the contact system and a potential drug target for different inflammatory, cardiovascular, infectious (sepsis) and oncology diseases (Sainz I. M. et al., Thromb Haemost 98, 77-83, 2007). The contact system is activated by either factor XIIa upon exposure to foreign or negatively charged surfaces or on endothelial cell surfaces by prolylcarboxypeptidases (Sainz I. M. et al., Thromb Haemost 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., N Engl J Med 359, 1027-1036, 2008).

SUMMARY

The present disclosure is, in part, based on the results derived from clinical studies showing that doses of DX-2930, an antibody binding to the active form of human plasma kallikrein, (e.g., 30 mg, 100 mg, 300 mg or 400 mg administered every two weeks) showed unexpected effectiveness in preventing HAE attack or reducing the rate of HAE attack in human patients. Further, DX-2930 treatment did not show evidence of dose-limiting toxicity when administered to humans. Overall, the results obtained from the instant study were unexpected since DX-2930 is the first completely specific plasma kallikrein inhibitor that has shown high efficacy in HAE treatment. This demonstrates that plasma kallikrein is central to disease pathogenesis.

Accordingly, one aspect of the present disclosure features a method of preventing HAE attack or reducing the rate of HAE attack (e.g., type I, II, or III HAE), the method comprising administering to a subject in need thereof an antibody binding to the active form of human plasma kallikrein (e.g., DX-2930) in an effective amount (e.g., about 30 mg-400 mg, about 100 mg-400 mg, about 100 mg-300 mg, or about 300 mg-400 mg). In some embodiments, the antibody is administered every two to four weeks for at least two times. In some embodiments, the antibody is administered at 300 mg or 400 mg every 2 weeks to four weeks (e.g., every two weeks or every four weeks).

In any one of the methods described herein, the antibody can be administered by subcutaneous administration. In some embodiments, the subject is a human patient experiencing at least two HAE attack per year (e.g., at least one HAE attack within 6 month prior to the first administration, at least 2 HAE attacks within 3 months prior to the first administration, or at least 9 HAE attacks within 3 months prior to the first administration). The HAE can be type I HAE or type II HAE. For example, the method described herein is for prophylactic treatment of HAE.

The antibody used in any of the methods described herein may be an antibody (e.g., a full-length antibody or an antigen-binding fragment) that binds the same epitope as DX-2930 or competes against DX-2930 for binding to active human plasma kallikrein. In some embodiments, the antibody comprises the same heavy chain and light chain CDRs. In one example, the antibody is DX-2930. Any of the antibody as described herein (e.g., DX-2930) may be formulated in a pharmaceutical composition, which comprises a pharmaceutically acceptable carrier. In some examples, the pharmaceutical composition comprises sodium phosphate, citric acid, histidine, sodium chloride, and Tween 80. In one example, the antibody (e.g., DX-2930) is formulated in 30 mM sodium phosphate, 8.6 mM citric acid, 50 mM histidine, 90 mM sodium chloride, and 0.01% Tween 80, pH 6.0.

In yet other aspects, the present disclosure features a method of treating HAE (e.g., type I, II, or III), the method comprising administering to a subject in need thereof an antibody binding to the active form of human plasma kallikrein (e.g., DX-2930) in an effective amount (e.g., 100-400 mg, 100-300 mg, 150 mg or 300 mg), wherein the DX-2930 antibody is administered in a dosage regimen having a loading period (e.g., first administered every week such as for at least one week), a maintenance period (e.g., subsequently administered every two to four weeks), and optionally a follow-on period.

In some embodiments, the antibody is administered to the subject at 100 to 300 mg (e.g., 150 mg or 300 mg) during the loading period. The loading period may be two weeks. The antibody may be administered at day 0, day 7, and day 14 at, e.g., 150 mg or 300 mg.

Alternatively or in addition, the antibody is administered to the subject at 100 to 300 mg (e.g., 150 mg or 300 mg) during the maintenance period. The maintenance period may last for 10 weeks. The antibody can be administered at day 28, day 42, day 56, day 70 and day 84.

In any of the methods described herein, the method may further comprise administering to the subject the antibody after the maintenance period once every two to four weeks (e.g., every two weeks or every four weeks). In some examples, the antibody is administered at 100 to 400 mg (e.g., 100 mg to 300 mg, for example, 150 mg or 300 mg).

In some embodiments of any one of the methods described herein, the antibody can be administered by subcutaneous administration. In some embodiments, the subject is a human patient suffering from, suspected of having, or at risk for HAE attack. For example, the method described herein is for prophylactic treatment of HAE. The subject may be a human patient who experienced at least 2 attacks per year (e.g., at least one attack per 4 weeks) prior to the treatment. In some embodiments, the antibody is administered for preventing HAE attack or for reducing the rate of HAE attack.

In some embodiments, the antibody (e.g., DX-2930) is first administered every week for one, two or three weeks and subsequently administered every two, three or four weeks. In some embodiments, the antibody (e.g., DX-2930) is subsequently administered every two weeks for ten weeks. In some embodiments, the subject has at least one attack every four weeks prior to the first administration.

The antibody to be used in any of the methods described herein may be an antibody that binds the same epitope as DX-2930 or competes against DX-2930 for binding to active human plasma kallikrein. In some embodiments, the antibody comprises the same heavy chain and light chain CDRs. In one example, the antibody is DX-2930.

Also within the scope of the present disclosure are (a) pharmaceutical compositions for use in treating HAE (e.g., preventing HAE attack or reducing the rate of HAE attack), the pharmaceutical composition comprising any of the anti-kallikrein antibodies described herein and a pharmaceutically acceptable carrier, wherein the pharmaceutical composition is administered to a subject following any of the treatment regimens described herein; and (b) use of the pharmaceutical composition for manufacturing a medicament for the treatment of HAE. Use of the antibodies for the intended purposes could be performed under the treating regimens as described herein.

The details of one or more embodiments of the invention are set forth in the description below. Other features or advantages of the present invention will be apparent from the following drawings and detailed description of several embodiments, and also from the appended claims.

DETAILED DESCRIPTION

Definitions

Figure 1:
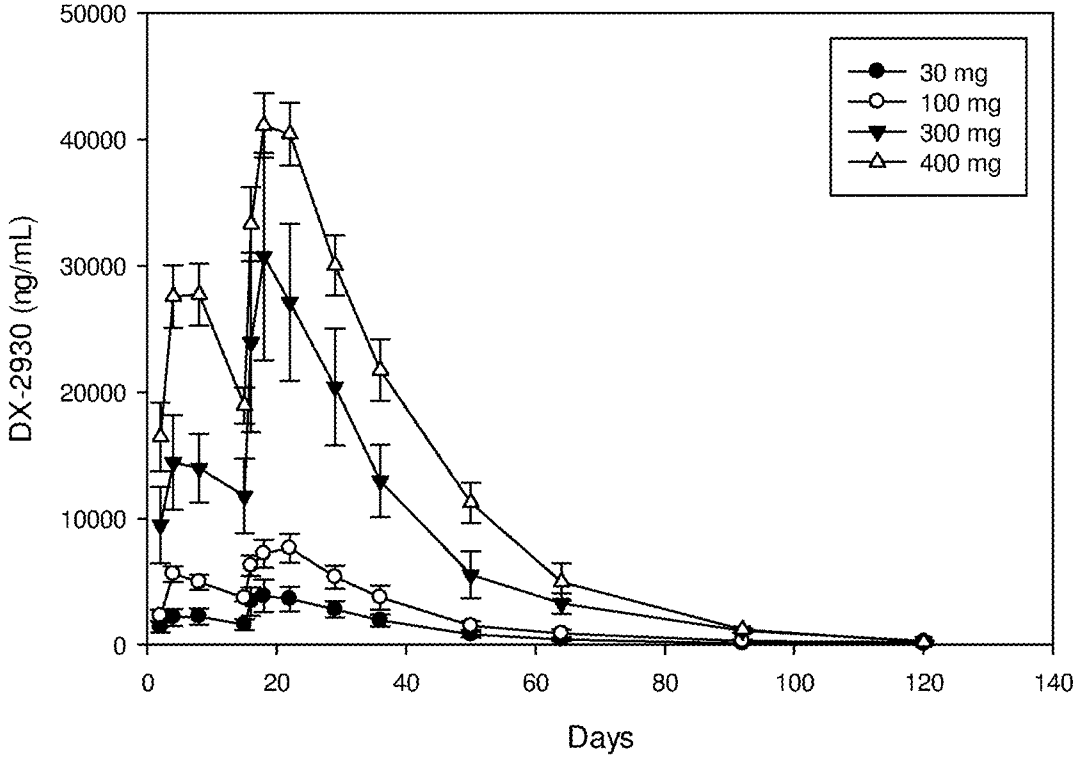
FIG. 1 shows DX-2930 plasma drug levels following subcutaneous dosing in HAE patients in the phase 1b study.

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

The term "antibody" refers to a protein that includes at least one immunoglobulin variable domain (variable region) or immunoglobulin variable domain (variable region) sequence. For example, an antibody can include a heavy (H) chain variable region (abbreviated herein as VH or HV), and a light (L) chain variable region (abbreviated herein as VL or LV). In another example, an antibody includes two heavy (H) chain variable regions and two light (L) chain variable regions. The term "antibody" encompasses antigen-binding fragments of antibodies (e.g., single chain antibodies, Fab and sFab fragments, $F(ab')_2$, Fd fragments, Fv fragments, scFv, and domain antibodies (dAb) fragments (de Wildt et al., Eur J Immunol. 1996; 26(3):629-39)) as well as complete antibodies. An antibody can have the structural features of IgA, IgG, IgE, IgD, IgM (as well as subtypes thereof). Antibodies may be from any source, but primate (human and non-human primate) and primatized are preferred.

The VH and VL regions can be further subdivided into regions of hypervariability, termed "complementarity determining regions" ("CDRs"), interspersed with regions that are more conserved, termed "framework regions" ("FRs"). The extent of the framework region and CDRs have been defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with plasma kallikrein.

The $V_H$ or $V_L$ chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and/or LC CDR3. Each of the light chain (LC) and/or heavy chain (HC) CDRs can be human. HC CDR3 can be human. One or more of the framework regions can be human, e.g., FR1, FR2, FR3, and/or FR4 of the HC and/or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, and/or CL1), or the entire antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody and that retain functionality include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See, e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refers to a preparation of antibodies or fragments thereof of single molecular composition, irrespective of how the antibody was generated.

Antibodies are "germlined" by reverting one or more non-germline amino acids in framework regions to corresponding germline amino acids of the antibody, so long as binding properties are substantially retained.

The inhibition constant (Ki) provides a measure of inhibitor potency; it is the concentration of inhibitor required to reduce enzyme activity by half and is not dependent on enzyme or substrate concentrations. The apparent Ki (Ki,app) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent Ki value. The Ki is obtained from the y-intercept extracted from a linear regression analysis of a plot of Ki,app versus substrate concentration.

$$v = v_o - v_o\left(\frac{(K_{i,app} + I + E) - \sqrt{(K_{i,app} + I + E)^2 - 4 \cdot I \cdot E}}{2 \cdot E}\right) \quad \text{Equation 1}$$

Where v=measured velocity; v0=velocity in the absence of inhibitor; Ki,app=apparent inhibition constant; I=total inhibitor concentration; and E=total enzyme concentration.

As used herein, "binding affinity" refers to the apparent association constant or KA. The KA is the reciprocal of the dissociation constant (KD). A binding antibody may, for example, have a binding affinity of at least 105, 106, 107, 108, 109, 1010 and 1011 M-1 for a particular target molecule, e.g., plasma kallikrein. Higher affinity binding of a binding antibody to a first target relative to a second target can be indicated by a higher KA (or a smaller numerical value KD) for binding the first target than the KA (or numerical value KD) for binding the second target. In such cases, the binding antibody has specificity for the first target (e.g., a protein in a first conformation or mimic thereof) relative to the second target (e.g., the same protein in a second conformation or mimic thereof, or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or 105 fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N \cdot [\text{Free}]/((1/KA) + [\text{Free}]).$$

It is not always necessary to make an exact determination of KA, though, since sometimes it is sufficient to obtain a quantitative measurement of affinity, e.g., determined using a method such as ELISA or FACS analysis, is proportional to KA, and thus can be used for comparisons, such as determining whether a higher affinity is, e.g., 2 fold higher, to obtain a qualitative measurement of affinity, or to obtain an inference of affinity, e.g., by activity in a functional assay, e.g., an in vitro or in vivo assay.

The term "binding antibody" (or "binding protein" used interchangeably herein) refers to an antibody that can interact with a target molecule. This term is used interchangeably with "ligand." A "plasma kallikrein binding antibody" refers to an antibody that can interact with (e.g., bind) plasma kallikrein, and includes, in particular, antibodies that preferentially or specifically interact with and/or inhibit plasma kallikrein. An antibody inhibits plasma kallikrein if it causes a decrease in the activity of plasma kallikrein as compared to the activity of plasma kallikrein in the absence of the antibody and under the same conditions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is possible for one or more framework and/or CDR amino acid residues of a binding protein to include one or more mutations (e.g., substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs, and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity, can be predicted, e.g., by evaluating whether the mutation is conservative or by the method of Bowie, et al. (1990) Science 247:1306-1310.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A first binding antibody "binds to the same epitope" as a second binding antibody if the first binding antibody binds to the same site on a target compound that the second binding antibody binds, or binds to a site that overlaps (e.g., 50%, 60%, 70%, 80%, 90%, or 100% overlap, e.g., in terms of amino acid sequence or other molecular feature (e.g., glycosyl group, phosphate group, or sulfate group)) with the site that the second binding antibody binds.

A first binding antibody "competes for binding" with a second binding antibody if the binding of the first binding antibody to its epitope decreases (e.g., by 10%, 20%, 30%, 40%, 50%, 60%, 70%, 80%, 90%, 100%, or more) the amount of the second binding antibody that binds to its epitope. The competition can be direct (e.g., the first binding antibody binds to an epitope that is the same as, or overlaps with, the epitope bound by the second binding antibody), or indirect (e.g., the binding of the first binding antibody to its epitope causes a steric change in the target compound that decreases the ability of the second binding antibody to bind to its epitope).

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In a preferred embodiment, the length of a reference sequence aligned for comparison purposes is at least 30%, preferably at least 40%, more preferably at least 50%, even more preferably at least 60%, and even more preferably at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

An "isolated" antibody refers to an antibody that is removed from at least 90% of at least one component of a natural sample from which the isolated antibody can be obtained. Antibodies can be "of at least" a certain degree of purity if the species or population of species of interest is at least 5, 10, 25, 50, 75, 80, 90, 92, 95, 98, or 99% pure on a weight-weight basis.

A "patient," "subject" or "host" (these terms are used interchangeably) to be treated by the subject method may mean either a human or non-human animal.

The terms "prekallikrein" and "preplasma kallikrein" are used interchangeably herein and refer to the zymogen form of active plasma kallikrein, which is also known as prekallikrein.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In some embodiments, a plasma kallikrein binding antibody can have about 85%, 90%, 91%, 92%, 93%, 94%, 95%, 96%, 97%, 98%, 99% or higher sequence identity to an antibody described herein. In some embodiments, a plasma kallikrein binding antibody can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to an antibody described herein (e.g., DX-2930). In some embodiments, a plasma kallikrein binding antibody can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to an antibody described herein (e.g., DX-2930). In some embodiments, a plasma kallikrein binding antibody can have about 85%, 90%, 91%, 92%, 93%, 94%, 95%, 96%, 97%, 98%, 99% or higher sequence identity in the constant region (e.g., CH1, CH2, CH3, and/or CL1) to an antibody described herein (e.g., DX-2930).

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding that are statistically significant (e.g., P value <0.05 or 0.02). The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

A "therapeutically effective dosage" preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

The term "treating" as used herein refers to the application or administration of a composition including one or more active agents to a subject, who has an allergic disease, a symptom of the allergic disease, or a predisposition toward the allergic disease, with the purpose to cure, heal, alleviate, relieve, alter, remedy, ameliorate, improve, or affect the disease, the symptoms of the disease, or the predisposition toward the disease. "Prophylactic treatment," also known as "preventive treatment," refers to a treatment that aims at protecting a person from, or reducing the risk for a disease to which he or she has been, or may be, exposed.

The term "preventing" a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. "Preventing" a disease may also be referred to as "prophylaxis" or "prophylactic treatment."

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Antibodies Specific to Plasma Kallikrein

Plasma kallikrein binding antibodies for use in the methods described herein can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment. The binding antibody can include two heavy chain immunoglobulins and two light chain immunoglobulins, or can be a single chain antibody. Plasma kallikrein binding antibodies can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding antibody is a monoclonal antibody.

In one aspect, the disclosure features an antibody (e.g., an isolated antibody) that binds to plasma kallikrein (e.g., human plasma kallikrein and/or murine kallikrein) and includes at least one immunoglobulin variable region. For example, the antibody includes a heavy chain (HC) immunoglobulin variable domain sequence and/or a light chain (LC) immunoglobulin variable domain sequence. In one embodiment, the antibody binds to and inhibits plasma kallikrein, e.g., human plasma kallikrein and/or murine kallikrein.

The antibody can include one or more of the following characteristics: (a) a human CDR or human framework region; (b) the HC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a HC variable domain described herein; (c) the LC immunoglobulin variable domain sequence comprises one or more (e.g., 1, 2, or 3) CDRs that are at least 85, 88, 89, 90, 91, 92, 93, 94, 95, 96, 97, 98, 99, or 100% identical to a CDR of a LC variable domain described herein; (d) the LC immunoglobulin variable domain sequence is at least 85, 88, 89, 90, 91, 92, 93, 94, 95, 96, 97, 98, 99, or 100% identical to a LC variable domain described herein (e.g., overall or in framework regions or CDRs); (e) the HC immunoglobulin variable domain sequence is at least 85, 88, 89, 90, 91, 92, 93, 94, 95, 96, 97, 98, 99, or 100% identical to a HC variable domain described herein (e.g., overall or in framework regions or CDRs); (f) the antibody binds an epitope bound by an antibody described herein, or competes for binding with an antibody described herein; (g) a primate CDR or primate framework region; (h) the HC immunoglobulin variable domain sequence comprises a CDR1 that differs by at least one amino acid but by no more than 2 or 3 amino acids from the CDR1 of a HC variable domain described herein; (i) the HC immunoglobulin variable domain sequence comprises a CDR2 that differs by at least one amino acid but by no more than 2, 3, 4, 5, 6, 7, or 8 amino acids from the CDR2 of a HC variable domain described herein; (j) the HC immunoglobulin variable domain sequence comprises a CDR3 that differs by at least one amino acid but by no more than 2, 3, 4, 5, or 6 amino acids from the CDR3 of a HC variable domain described herein; (k) the LC immunoglobulin variable domain sequence comprises a CDR1 that differs by at least one amino acid but by no more than 2, 3, 4, or 5 amino acids from the CDR1 of a LC variable domain described herein; (l) the LC immunoglobulin variable domain sequence comprises a CDR2 that differs by at least one amino acid but by no more than 2, 3, or 4 amino acids from the CDR2 of a LC variable domain described herein; (m) the LC immunoglobulin variable domain sequence comprises a CDR3 that differs by at least one amino acid but by no more than 2, 3, 4, or 5 amino acids from the CDR3 of a LC variable domain described herein; (n) the LC immunoglobulin variable domain sequence differs by at least one amino acid but by no more than 2, 3, 4, 5, 6, 7, 8, 9, or 10 amino acids from a LC variable domain described herein (e.g., overall or in framework regions or CDRs); and (o) the HC immunoglobulin variable domain sequence differs by at least one amino acid but by no more than 2, 3, 4, 5, 6, 7, 8, 9, or 10 amino acids from a HC variable domain described herein (e.g., overall or in framework regions or CDRs).

The plasma kallikrein binding protein may be an isolated antibody (e.g., at least 70, 80, 90, 95, or 99% free of other proteins). In some embodiments, the plasma kallikrein binding antibody, or composition thereof, is isolated from antibody cleavage fragments (e.g., DX-2930) that are inactive or partially active (e.g., bind plasma kallikrein with a Ki, app of 5000 nM or greater) compared to the plasma kallikrein binding antibody. For example, the plasma kallikrein binding antibody is at least 70% free of such antibody cleavage fragments; in other embodiments the binding antibody is at least 80%, at least 90%, at least 95%, at least 99% or even 100% free from antibody cleavage fragments that are inactive or partially active.

The plasma kallikrein binding antibody may additionally inhibit plasma kallikrein, e.g., human plasma kallikrein.

In some embodiments, the plasma kallikrein binding antibody does not bind prekallikrein (e.g., human prekallikrein and/or murine prekallikrein), but binds to the active form of plasma kallikrein (e.g., human plasma kallikrein and/or murine kallikrein).

In certain embodiments, the antibody binds at or near the active site of the catalytic domain of plasma kallikrein, or a fragment thereof, or binds an epitope that overlaps with the active site of plasma kallikrein.

In some aspects, the antibody binds the same epitope or competes for binding with an antibody described herein.

The antibody can bind to plasma kallikrein, e.g., human plasma kallikrein, with a binding affinity of at least $10^5$, $10^6$, $10^7$, $10^8$, $10^9$, $10^{10}$ and $10^{11}$ $M^{-1}$. In one embodiment, the antibody binds to human plasma kallikrein with a $K_{off}$ slower than $1\times10^{-3}$, $5\times10^{-4}$ $s^{-1}$, or $1\times10^{-4}$ $s^{-1}$. In one embodiment, the antibody binds to human plasma kallikrein with a $K_{on}$ faster than $1\times10^2$, $1\times10^3$, or $5\times10^3$ $M^{-1}s^{-1}$. In one embodiment, the antibody binds to plasma kallikrein, but does not bind to tissue kallikrein and/or plasma prekallikrein (e.g., the antibody binds to tissue kallikrein and/or plasma prekallikrein less effectively (e.g., 5-, 10-, 50-, 100-, or 1000-fold less or not at all, e.g., as compared to a negative control) than it binds to plasma kallikrein.

In one embodiment, the antibody inhibits human plasma kallikrein activity, e.g., with a Ki of less than $10^{-5}$, $10^{-6}$, $10^{-7}$, $10^{-8}$, $10^{-9}$, and $10^{-10}$ M. The antibody can have, for example, an $IC_{50}$ of less than 100 nM, 10 nM, 1, 0.5, or 0.2 nM. For example, the antibody may modulate plasma kallikrein activity, as well as the production of Factor XIIa (e.g., from Factor XII) and/or bradykinin (e.g., from high-molecular-weight kininogen (HMWK)). The antibody may inhibit plasma kallikrein activity, and/or the production of Factor XIIa (e.g., from Factor XII) and/or bradykinin (e.g., from high-molecular-weight kininogen (HMWK)). The affinity of the antibody for human plasma kallikrein can be characterized by a $K_D$ of less than 100 nm, less than 10 nM, less than 5 nM, less than 1 nM, less than 0.5 nM. In one embodiment, the antibody inhibits plasma kallikrein, but does not inhibit tissue kallikrein (e.g., the antibody inhibits tissue kallikrein less effectively (e.g., 5-, 10-, 50-, 100-, or 1000-fold less or not at all, e.g., as compared to a negative control) than it inhibits plasma kallikrein.

In some embodiments, the antibody has an apparent inhibition constant ($K_{i,app}$) of less than 1000, 500, 100, 5, 1, 0.5 or 0.2 nM.

Plasma kallikrein binding antibodies may have their HC and LC variable domain sequences included in a single polypeptide (e.g., scFv), or on different polypeptides (e.g., IgG or Fab).

In one embodiment, the HC and LC variable domain sequences are components of the same polypeptide chain. In another, the HC and LC variable domain sequences are components of different polypeptide chains. For example, the antibody is an IgG, e.g., IgG1, IgG2, IgG3, or IgG4. The antibody can be a soluble Fab. In other implementations the antibody includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the antibody is a human or humanized antibody or is non-immunogenic in a human. For example, the antibody includes one or more human antibody framework regions, e.g., all human framework regions, or framework regions at least 85, 88, 89, 90, 91, 92, 93, 94, 95, 96, 97, 98, 99% identical to human framework regions. In one embodiment, the antibody includes a human Fc domain, or an Fc domain that is at least 95, 96, 97, 98, or 99% identical to a human Fc domain.

In one embodiment, the antibody is a primate or primatized antibody or is non-immunogenic in a human. For example, the antibody includes one or more primate antibody framework regions, e.g., all primate framework regions, or framework regions at least 85, 88, 89, 90, 91, 92, 93, 94, 95, 96, 97, 98, 99% identical to primate framework regions. In one embodiment, the antibody includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers.

In some embodiments, the affinity of the primate antibody for human plasma kallikrein is characterized by a $K_D$ of less than 1000, 500, 100, 10, 5, 1, 0.5 nM, e.g., less than 10 nM, less than 1 nM, or less than 0.5 nM.

In certain embodiments, the antibody includes no sequences from mice or rabbits (e.g., is not a murine or rabbit antibody).

In some embodiments, the antibody used in the methods described herein may be DX-2930 as described herein or a functional variant thereof, or an antibody that binds the same epitope as DX-2930 or competes against DX-2930 for binding to active plasma kallikrein.

In one example, a functional variant of DX-2930 comprises the same complementary determining regions (CDRs) as DX-2930, as determined by the same method. In another example, the functional variants of DX-2930 may contain one or more mutations (e.g., conservative substitutions) in the FRs of either the $V_H$ or the $V_L$ as compared to those in the $V_H$ and $V_L$ of DX-2930. Preferably, such mutations do not occur at residues which are predicted to interact with one or more of the CDRs, which can be determined by routine technology. In other embodiments, the functional variants described herein contain one or more mutations (e.g., 1, 2, or 3) within one or more of the CDR regions of DX-2930. Preferably, such functional variants retain the same regions/residues responsible for antigen-binding as the parent. In yet other embodiments, a functional variant of DX-2930 may comprise a $V_H$ chain that comprises an amino acid sequence at least 85% (e.g., 90%, 92%, 94%, 95%, 96%, 97%, 98%, or 99%) identical to that of the $V_H$ of DX-2930 and/or a $V_L$ chain that has an amino acid sequence at least 85% (e.g., 90%, 92%, 94%, 95%, 96%, 97%, 98%, or 99%) identical to that of the $V_L$ of DX-2930. These variants are capable of binding to the active form of plasma kallikrein and preferably do not bind to prekallikrein.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the antibody used in the methods and compositions described herein may be the DX-2930 antibody. The heavy and light chain full and variable sequences for DX-2930 are provided below, with signal sequences in italics. The CDRs are boldfaced and underlined (based on the Kabat numbering scheme).

DX-2930 Heavy Chain Amino Acid Sequence (451 amino acids, 49439.02 Da)

(SEQ ID NO: 1)

*MGWSCILFLVATATGAHS*EVQLLESGGGLVQPGGSLRLSCAASGFTFSHY

IMMWVRQAPGKGLEWVSGIYSSGGITVYADSVKGRFTISRDNSKNTLYLQ

MNSLRAEDTAVYYCAYRRIGVPRRDEFDIWGQGTMVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPG

DX-2930 Light Chain Amino Acid Sequence (213 amino acids, 23419.08 Da)

(SEQ ID NO: 2)

*MGWSCILFLVATATGAHS*DIQMTQSPSTLSASVGDRVTITCRASQSISSW

LAWYQQKPGKAPKLLIYKASTLESGVPSRFSGSGSGTEFTLTISSLQPDD

FATYYCQQYNTYWTFGQGTKVEIKRTVAAPSVFIFPPSDEQLKSGTASVV

CLLNNFYPREAKVQWKVDNALQSGNSQESVTEQDSKDSTYSLSSTLTLSK

ADYEKHKVYACEVTHQGLSSPVTKSFNRGEC

-continued

DX-2930 Heavy Chain Variable Domain Amino Acid Sequence (SEQ ID NO: 3)

EVQLLESGGGLVQPGGSLRLSCAASGFTFSHYIMMWVRQAPGKGLEWVSG
IYSSGGITVYADSVKGRFTISRDNSKNTLYLQMNSLRAEDTAVYYCAYRR
IGVPRRDEFDIWGQGTMVTVSS

DX-2930 Light Chain Variable Domain Amino Acid Sequence (SEQ ID NO: 4)

DIQMTQSPSTLSASVGDRVTITCRASQSISSWLAWYQQKPGKAPKLLIYK
ASTLESGVPSRFSGSGSGTEFTLTISSLQPDDFATYYCQQYNTYWTFGQG
TKVEIK

TABLE 1

CDRs for DX-2930.

| CDR | Amino acid sequence |
|---|---|
| Heavy chain CDR1 | HYIMM (SEQ ID NO: 5) |
| Heavy chain CDR2 | GIYSSGGITVYADSVKG (SEQ ID NO: 6) |
| Heavy chain CDR3 | RRIGVPRRDEFDI (SEQ ID NO: 7) |
| Light chain CDR1 | RASQSISSWLA (SEQ ID NO: 8) |
| Light chain CDR2 | KASTLES (SEQ ID NO: 9) |
| Light chain CDR3 | QQYNTYWT (SEQ ID NO: 10) |

Antibody Preparation

An antibody as described herein (e.g., DX-2930) can be made by any method known in the art. See, for example, Harlow and Lane, (1988) Antibodies: A Laboratory Manual, Cold Spring Harbor Laboratory, New York and Greenfield, (2013) Antibodies: A Laboratory Manual, Second edition, Cold Spring Harbor Laboratory Press.

The sequence encoding the antibody of interest, e.g., DX-2930, may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of PKal. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated or synthesized. The DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Alternatively, techniques described for the production of single chain antibodies (U.S. Pat. Nos. 4,946,778 and 4,704, 692) can be adapted to produce a phage or yeast scFv library and scFv clones specific to a PKal can be identified from the library following routine procedures. Positive clones can be subjected to further screening to identify those that inhibits PKal activity.

Some antibodies, e.g., Fabs, can be produced in bacterial cells, e.g., *E. coli* cells (see e.g., Nadkarni, A. et al., 2007 Protein Expr Purif 52(1):219-29). For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, J. Immunol. Methods. 251:123-35; Schoonooghe S. et al., 2009 BMC Biotechnol. 9:70; Abdel-Salam, H A. et al., 2001 Appl Microbiol Biotechnol 56(1-2):157-64; Takahashi K. et al., 2000 Biosci Biotechnol Biochem 64(10):2138-44; Edqvist, J. et al., 1991 J Biotechnol 20(3):291-300), *Hanseula*, or *Saccharomyces*. One of skill in the art can optimize antibody production in yeast by optimizing, for example, oxygen conditions (see e.g., Baumann K., et al. 2010 BMC Syst. Biol. 4:141), osmolarity (see e.g., Dragosits, M. et al., 2010 BMC Genomics 11:207), temperature (see e.g., Dragosits, M. et al., 2009 J Proteome Res. 8(3):1380-92), fermentation conditions (see e.g., Ning, D. et al. 2005 J. Biochem. and Mol. Biol. 38(3): 294-299), strain of yeast (see e.g., Kozyr, A V et al. 2004 Mol Biol (Mosk) 38(6): 1067-75; Horwitz, A H. et al., 1988 Proc Natl Acad Sci USA 85(22):8678-82; Bowdish, K. et al. 1991 J Biol Chem 266(18):11901-8), overexpression of proteins to enhance antibody production (see e.g., Gasser, B. et al., 2006 Biotechol. Bioeng. 94(2):353-61), level of acidity of the culture (see e.g., Kobayashi H., et al., 1997 FEMS Microbiol Lett 152(2):235-42), concentrations of substrates and/or ions (see e.g., Ko J H. et al., 2996 Appl Biochem Biotechnol 60(1): 41-8). In addition, yeast systems can be used to produce antibodies with an extended half-life (see e.g., Smith, B J. et al. 2001 Bioconjug Chem 12(5):750-756), In one preferred embodiment, antibodies are produced in mammalian cells.

Preferred mammalian host cells for expressing the clone antibodies or antigen-binding fragments thereof include Chinese Hamster Ovary (CHO cells) (including dhfr− CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NS0 myeloma cells and SP2 cells, COS cells, HEK293T cells (J. Immunol. Methods (2004) 289(1-2):65-80), and a cell from a transgenic animal, e.g., a transgenic mammal. For example, the cell is a mammary epithelial cell.

In some embodiments, plasma kallikrein binding antibodies are produced in a plant or cell-free based system (see e.g., Galeffi, P., et al., 2006 J Transl Med 4:39).

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, Adv. Immunol. 51:1-84; Jefferis et al., 1998, Immunol. Rev. 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Pharmaceutical Compositions

An antibody as described herein (e.g., DX-2930) can be present in a composition, e.g., a pharmaceutically acceptable composition or pharmaceutical composition. The antibody as described herein (e.g., DX-2930) can be formulated together with a pharmaceutically acceptable carrier. In some embodiments, 30 mg-400 mg of DX-2930 antibody are present in a composition, optionally with a pharmaceutically acceptable carrier, e.g., a pharmaceutically acceptable composition or pharmaceutical composition. In some embodiments, 30 mg, 100 mg, 150 mg, 300 mg, or 400 mg of DX-2930 antibody are present in a composition optionally with a pharmaceutically acceptable carrier, e.g., a pharmaceutically acceptable composition or pharmaceutical composition.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for subcutaneous, intravenous, intramuscular, parenteral, spinal, or epidermal administration (e.g., by injection or infusion), although carriers suitable for inhalation and intranasal administration are also contemplated. In some embodiments, the pharmaceutically acceptable carrier is one or more of sodium phosphate, citric acid, histidine, sodium chloride, and Tween 80. In some embodiments, the pharmaceutically acceptable carrier is sodium phosphate, citric acid, histidine, sodium chloride, and Tween 80. In some embodiments, the antibody, such as DX-2930, is formulated in 30 mM sodium phosphate, 8.6 mM citric acid, 50 mM histidine, 90 mM sodium chloride, 0.01% Tween 80, pH 6.0. In some embodiments, the composition comprises or consists of 100 mg DX-2930 per 1 mL solution of 30 mM sodium phosphate, 8.6 mM citric acid, 50 mM histidine, 90 mM sodium chloride, 0.01% Tween 80.

A pharmaceutically acceptable salt is a salt that retains the desired biological activity of the compound and does not impart any undesired toxicological effects (see e.g., Berge, S. M., et al., 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the plasma kallikrein binding protein is administered by intravenous infusion or injection. In another preferred embodiment, the plasma kallikrein binding protein is administered by intramuscular or subcutaneous injection. In another preferred embodiment, the plasma kallikrein binding protein is administered by intraperitoneal injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An antibody as described herein (e.g., DX-2930) can be administered by a variety of methods, including intravenous injection or infusion. For example, for some therapeutic applications, the antibody can be administered by intravenous infusion at a rate of less than 30, 20, 10, 5, or 1 mg/min to reach a dose of about 1 to 100 $mg/m^2$ or 7 to 25 $mg/m^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an antibody as described herein (e.g., DX-2930) can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, J. Clin. Pharmacol. 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody as described herein (e.g., DX-2930) is 30 mg to 400 mg, or any integer in between, for example, 100-400 mg, 100-300 mg, or 300-400 mg. In some embodiments, the therapeutically or prophylactically effective amount is 30 mg, 100 mg, 150 mg, 200 mg, 250 mg, 300 mg, 350 mg, or 400 mg.

In some embodiments, the therapeutically or prophylactically effective amount of an antibody described herein (e.g., DX-2930) is 30 mg, 100 mg, 150 mg, 300 mg, or 400 mg. In some embodiments, the therapeutically or prophylactically effective amount is 150 mg. In some embodiments, the therapeutically or prophylactically effective amount is 300 mg. In some embodiments, the therapeutically or prophylactically effective amount is 400 mg.

In some embodiments, the therapeutically or prophylactically effective amount is administered at least two times, at least three times, at least four times, at least five times, at least six times, at least seven times, at least eight times, at least nine times, at least ten times, or more. In some embodiments, the therapeutically or prophylactically effective amount is administered every other week (i.e., every two weeks). In some embodiments, the therapeutically or prophylactically effective amount is 300 mg or 400 mg and the amount is administered every two weeks. In some embodiments, the therapeutically or prophylactically effective amount is 300 mg and this amount of the antibody is administered every two weeks. In some embodiments, the therapeutically or prophylactically effective amount is 400 mg and this amount of the antibody is administered every two weeks.

In some embodiments, treatment of any of the anti-pKal antibody such as DX-2930 involves a treatment regimen comprising at least a loading period and a maintenance period. In some embodiments, the therapeutically or prophylactically effective amount of the antibody for the loading period is 100 to 300 mg (e.g., 150 mg or 300 mg) per each administration. During this period, the antibody may be administered every week (e.g., every week for one, two or three weeks). In one example, the loading period is 2 weeks and the antibody is administered at day 0, day 7, and day 14.

Alternatively or in addition, the therapeutically or prophylactically effective amount for the maintenance period is about 100 to 300 mg (e.g., 150 mg or 300 mg) per each administration. During this period, the antibody can be administered every other week (i.e., every two weeks), every three weeks, or every four weeks (e.g., every two weeks for ten weeks, resulting in delivery of 5 doses total). In one example, the maintenance period may last for 10 weeks and the antibody is administered at day 28, day 42, day 56, day 70, and day 84.

In some embodiments, the anti-pKal antibody such as DX-2930 is administered at 150 mg or 300 mg and the amount is first administered every week for a suitable period (e.g., every week for one, two or three weeks) and subsequently administered every two to four weeks (e.g., every two, three or four weeks) for a suitable period.

In any of the methods described herein, the treatment regimen may further comprise a follow-up period after the maintenance period. In the follow-up period, the antibody such as DX-2930 may be administered every 2-4 weeks at 100-300 mg, for example 300 mg. In some instances, the dosage may increase to 400 mg in one or more of the loading period, the maintenance period, and the follow-up period.

The pharmaceutical compositions disclosed herein may include a "therapeutically effective amount" or a "prophylactically effective amount" of an antibody as described herein (e.g., DX-2930).

Kits

An antibody as described herein (e.g., DX-2930) can be provided in a kit, e.g., as a component of a kit. For example, the kit includes (a) a DX-2930 antibody, e.g., a composition (e.g., a pharmaceutical composition) that includes the antibody, and, optionally (b) informational material. The informational material can be descriptive, instructional, marketing or other material that relates to a method described herein and/or the use of an antibody as described herein (e.g., DX-2930), e.g., for a method described herein. In some embodiments, the kit comprises one or more doses of DX-2930. In some embodiments, the one or more doses are 30 mg, 100 mg, 150 mg, 300 mg or 400 mg.

The informational material of the kit is not limited in its form. In one embodiment, the informational material can include information about production of the compound, molecular weight of the compound, concentration, date of expiration, batch or production site information, and so forth. In one embodiment, the informational material relates to using the antibody to treat, prevent, or diagnosis of disorders and conditions, e.g., a plasma kallikrein associated disease or condition.

In one embodiment, the informational material can include instructions to administer n antibody as described herein (e.g., DX-2930) in a suitable manner to perform the methods described herein, e.g., in a suitable dose, dosage form, mode of administration or dosing schedule (e.g., a dose, dosage form, dosing schedule or mode of administration described herein). In another embodiment, the informational material can include instructions to administer an antibody as described herein (e.g., DX-2930) to a suitable subject, e.g., a human, e.g., a human having, or at risk for, a plasma kallikrein associated disease or condition. For example, the material can include instructions to administer an antibody as described herein (e.g., DX-2930) to a patient with a disorder or condition described herein, e.g., a plasma kallikrein associated disease, e.g., according to a dosing schedule described herein. The informational material of the kits is not limited in its form. In many cases, the informational material, e.g., instructions, is provided in print but may also be in other formats, such as computer readable material.

An antibody as described herein (e.g., DX-2930) can be provided in any form, e.g., liquid, dried or lyophilized form. It is preferred that an antibody be substantially pure and/or sterile. When an antibody is provided in a liquid solution, the liquid solution preferably is an aqueous solution, with a sterile aqueous solution being preferred. When an antibody is provided as a dried form, reconstitution generally is by the addition of a suitable solvent. The solvent, e.g., sterile water or buffer, can optionally be provided in the kit.

The kit can include one or more containers for the composition containing an antibody as described herein (e.g., DX-2930). In some embodiments, the kit contains separate containers, dividers or compartments for the composition and informational material. For example, the composition can be contained in a bottle, vial, or syringe, and the informational material can be contained in association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an antibody as described herein (e.g., DX-2930). For example, the kit includes a plurality of syringes, ampules, foil packets, or blister packs, each containing a single unit dose of an antibody as described herein (e.g., DX-2930). The containers of the kits can be air tight, waterproof (e.g., impermeable to changes in moisture or evaporation), and/or light-tight.

The kit optionally includes a device suitable for administration of the composition, e.g., a syringe, or any such delivery device. In one embodiment, the device is an implantable device that dispenses metered doses of the antibody. The disclosure also features a method of providing a kit, e.g., by combining components described herein.

Treatment

In some aspects, the disclosure provides the use of an antibody as described herein (e.g., DX-2930) in treating HAE.

Hereditary Angioedema

Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called erythema *marginatum* during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III, all of which can be treated by the methods described herein. It is estimated that HAE affects 1 in 50,000 people, that type I accounts for about 85 percent of cases, type II accounts for about 15 percent of cases, and type III is very rare. Patients having type I or type II HAE are typically deficient in C1-INH. Such patients either have a defective C1-INH gene and thus do not produce C1-INH, or produce atypical C1-INH proteins. Type III is the most newly described form and was originally thought to occur only in women, but families with affected males have been identified. Type III HAE is believed to be unassociated with C1-INH. Patients having type III HAE may have normal C1-INH proteins.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., J Allergy Clin Immunol, 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. Cinryze (ViroPharma), which is nanofiltered, was approved by the F.D.A. in 2008 for prophylaxis. Rhucin (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®, DX-88, Dyax) inhibits plasma kallikrein and has been approved in the U.S.. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., J Allergy Clin Immunol, 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. Patient. 2012; 5(2):113-26.

Treating HAE with Anti-PKal Antibodies

The disclosure provides methods of treating (e.g., ameliorating, stabilizing, or eliminating one or more symptoms) of hereditary angioedema (HAE) by administering an antibody described herein (e.g., a therapeutically effective amount of an antibody described herein) to a subject having or suspected of having HAE, e.g., according to a dosing schedule described herein. Additionally provided are methods of treating HAE by administering an antibody described herein (e.g., a therapeutically effective amount of an antibody described herein), e.g., according to a dosing schedule described herein, or in combination with a second therapy, e.g., with one other agent, e.g., described herein. The disclosure also provides methods of preventing HAE or a symptom thereof by administering an antibody described herein (e.g., a prophylactically effective amount of an antibody described herein) to a subject at risk of developing HAE (e.g., a subject having a family member with HAE or a genetic predisposition thereto), e.g., according to a dosing schedule described herein. In some examples, the subject may be a human patient who has no HAE symptoms at the time of the treatment.

Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

Methods of administering DX-2930 antibodies are also described in "Pharmaceutical Compositions." Suitable dosages of the antibody used can depend on the age and weight of the subject and the particular drug used. The antibody can be used as competitive agents to inhibit, reduce an undesirable interaction, e.g., between plasma kallikrein and its substrate (e.g., Factor XII or HMWK). The dose of the antibody can be the amount sufficient to block 90%, 95%, 99%, or 99.9% of the activity of plasma kallikrein in the patient, especially at the site of disease. This may require 30 mg, 100 mg, 300 mg, or 400 mg, e.g., administered every two weeks.

In one embodiment, the antibodies are used to inhibit an activity (e.g., inhibit at least one activity of plasma kallikrein, e.g., reduce Factor XIIa and/or bradykinin production) of plasma kallikrein, e.g., in vivo. The binding proteins can be used by themselves or conjugated to an agent, e.g., a cytotoxic drug, cytotoxin enzyme, or radioisotope.

The antibodies can be used directly in vivo to eliminate antigen-expressing cells via natural complement-dependent cytotoxicity (CDC) or antibody dependent cellular cytotoxicity (ADCC). The antibodies described herein can include complement binding effector domain, such as the Fc portions from IgG1, -2, or -3 or corresponding portions of IgM which bind complement. In one embodiment, a population of target cells is ex vivo treated with an antibody described herein and appropriate effector cells. The treatment can be supplemented by the addition of complement or serum containing complement. Further, phagocytosis of target cells coated with an antibody described herein can be improved by binding of complement proteins. In another embodiment target, cells coated with the antibody which includes a complement binding effector domain are lysed by complement.

Methods of administering DX-2930 antibodies are described in "Pharmaceutical Compositions." Suitable dosages of the molecules used will depend on the age and weight of the subject and the particular drug used. The antibodies can be used as competitive agents to inhibit or reduce an undesirable interaction, e.g., between a natural or pathological agent and the plasma kallikrein.

A therapeutically effective amount of an antibody as described herein, can be administered to a subject having, suspected of having, or at risk for HAE, thereby treating (e.g., ameliorating or improving a symptom or feature of a disorder, slowing, stabilizing and/or halting disease progression) the disorder.

The antibody described herein can be administered in a therapeutically effective amount. A therapeutically effective amount of an antibody is the amount which is effective, upon single or multiple dose administration to a subject, in treating a subject, e.g., curing, alleviating, relieving or improving at least one symptom of a disorder in a subject to a degree beyond that expected in the absence of such treatment.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

In some embodiments, the DX-2930 antibody is administered by multiple doses such as once every 2 weeks, once every 3 weeks, once every four weeks, once every 6 weeks, once every 8 weeks or less frequent. Each of the multiple doses can be 30 mg, 100 mg, 150 mg, 300 mg, 350 mg. or 400 mg. In some instances, a patient may be given multiple doses once every 2 weeks, for a suitable period of time. In some embodiments, DX-2930 can be administered at 300 mg or 400 mg every two weeks. In other embodiments, DX-2930 can be administered at 300 mg or 400 mg every four weeks. In yet other embodiments, DX-2930 can be administered at 150 mg every four weeks. In any of the methods described herein, a subject treated by DX-2930 for multiple doses as described herein may be followed up with a maintenance treatment.

In any of the methods described herein, a subject may be treated by DX-2930 for multiple doses in a loading period and then followed up with a maintenance period. In the loading period, the subject may be treated with DX-2930 at about 100 mg to about 400 mg (e.g., 100-300 mg or 150-300 mg, for example, 100 mg, 150 mg, 200 mg, 300 mg, or 400 mg) once every 2-4 weeks (for example, every 2 weeks, every 3 weeks, or every 4 weeks) for a suitable period. In the loading period, the subject may be treated with DX-2930 at about 100 mg to about 300 mg (e.g., 100-300 mg or 150-300 mg, for example, 100 mg, 150 mg, 200 mg, or 300 mg) once every 2-4 weeks (for example, every 2 weeks, every 3 weeks, or every 4 weeks) for a suitable period.

In some embodiments, the patient can be monitored for side effects (e.g., elevation of creatine phosphatase levels) and/or inhibition levels of pKal by the antibody (e.g., serum or plasma concentration of the antibody or the pKal activity level) before and after the treatment or during the course of treatment. If adverse effect is observed, the dose of the antibody might be reduced or the treatment might be terminated. If the inhibition level is below a minimum therapeutic level, further doses of the antibody might be administered to the patient.

In some embodiments, the plasma or serum concentration of the antibody (e.g., DX-2930) may be measured during the course of the treatment (e.g., after the initial dosage) for assessing the efficacy of the treatment. If the plasma or serum concentration of the antibody is lower than about 80 nM, a follow-up dosage may be needed, which may be the same or higher than the initial dosage. The plasma or serum concentration of the antibody may be measured by determining the protein level of the antibody in a plasma or serum sample obtained from the subject, e.g., by an immune assay or MS assay. The plasma or serum concentration of the antibody may also be measured by determining the inhibitory level of pKal in a plasma or serum sample obtained from a subject treated with the antibody. Such assays may include the synthetic substrate assay or the Western blot assay for measuring cleaved kininogen as described herein.

Alternatively or in addition, the plasma or serum level of creatine kinase can be monitored during the course of the treatment. If the plasma or serum level of creatine kinase is found to elevate during the treatment, the dosage of the antibody may be reduced or the treatment may be terminated.

In some embodiments, an optimal dosage (e.g., optimal prophylactic dosage or optimal therapeutic dosage) of the antibody (e.g., DX-2930) may be determined as follows. The antibody is given to a subject in need of the treatment at an initial dose. The plasma concentration of the antibody in the subject is measured. If the plasma concentration is lower than 80 nM, the dose of the antibody is increased in a subsequent administration. A dosage of the antibody that maintains the antibody plasma concentration above about 80 nM can be chosen as the optimal dosage for the subject. The creatine phosphokinase level of the subject can be monitored during the course of treatment and the optimal dosage for that subject can be further adjusted based on the creatine phosphokinase level, e.g., the dosage of the antibody might be reduced is elevation of creatine phosphokinase is observed during treatment. In some embodiments, the antibody such as DX-2930 is administered to reduce the level of cleaved kininogen to levels comparable to healthy subjects.

In some embodiments, any of the antibodies disclosed herein, such as DX-2930 and its functional variants, may be used to prevent HAE attack or reduce the rate of HAE attack in human patients having history of HAE attack. In some examples, the human patients experienced at least two HAE attacks per year and optionally at least one within the 6 months prior to the treatment. In other examples, the human patients experienced at least two HAE attacks within 3 months prior to the treatment. In other examples, the human patients had at least 9 HAE attacks within 3 months prior to the treatment and optionally at least 25 attacks (e.g., 36 attacks) within 12 months prior to the treatment.

Combination Therapies

An antibody as described herein (e.g., DX-2930) can be administered in combination with one or more of the other therapies for treating a disease or condition associated with plasma kallikrein activity, e.g., a disease or condition described herein. For example, an antibody as described herein (e.g., DX-2930) can be used therapeutically or prophylactically with surgery, another anti-plasma kallikrein Fab or IgG (e.g., another Fab or IgG described herein), another plasma kallikrein inhibitor, a peptide inhibitor, or small molecule inhibitor. Examples of plasma kallikrein inhibitors that can be used in combination therapy with a plasma kallikrein binding antibodies described herein include plasma kallikrein inhibitors described in, e.g., WO 95/21601 or WO 2003/103475.

One or more plasma kallikrein inhibitors can be used in combination with an antibody as described herein (e.g., DX-2930). For example, the combination can result in a lower dose of the inhibitor being needed, such that side effects are reduced.

An antibody as described herein (e.g., DX-2930) can be administered in combination with one or more current therapies for treating HAE. For example, DX-2930 antibody can be co-used with a second anti-HAE therapeutic agent such as ecallantide, a C1 esterase inhibitor (e.g., CINRYZE™), aprotinin (TRASYLOL®), and/or a bradykinin B2 receptor inhibitor (e.g., icatibant (FIRAZYR®)).

The term "combination" refers to the use of the two or more agents or therapies to treat the same patient, wherein the use or action of the agents or therapies overlaps in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of a plasma kallikrein binding antibody described herein can also be used to reduce the dosage of another therapy, e.g., to reduce the side effects associated with another agent that is being administered. Accordingly, a combination can include administering a second agent at a dosage at least 10, 20, 30, or 50% lower than would be used in the absence of the plasma kallikrein binding antibody.

A combination therapy can include administering an agent that reduces the side effects of other therapies. The agent can be an agent that reduces the side effects of a plasma kallikrein associated disease treatment.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: A Phase 1b, Double-Blind, Multiple Ascending Dose Study to Assess Safety, Tolerability and Pharmacokinetics of DX-2930 in Hereditary Angioedema Subjects A phase 1b trial was conducted to assess safety and tolerability of multiple subcutaneous administrations of DX-2930 at different dose levels in hereditary angioedema (HAE) subjects. HAE patients included in the study included those with documented diagnosis of HAE (Type I or Type II) based upon all of the following: documented clinical history consistent with HAE (subcutaneous or mucosal, nonpruritic swelling episodes without accompanying urticaria), C1 inhibitor (C1-INH) antigen or functional level <40% of the normal level (Subjects with antigen or functional C1-INH level 40-50% of the normal level were enrolled if they also had a C4 level below the normal range and a family history consistent with HAE Type I or II), age at reported onset of first angioedema symptoms ≤30 years or a family history consistent with HAE Type I or II, and experiencing ≥2 HAE attacks per year, with at least 1 attack in the past 6 months reported by the subject. HAE patients enrolled were randomized in a 2:1 ratio of active drug to placebo and administered subcutaneous doses of DX-2930 at 30 mg (n=4), 100 mg (n=4), 300 mg (n=5), and 400 mg (n=11) or placebo (n=13) in two doses separated by 14 days. One patient in the 400 mg group received only one dose and then was unavailable for the second dose and was replaced. The replacement patient was also unable to complete the study for reasons not related to the study, resulting a total of 10 patients completing the 400 mg dose and being included in the assessment. Plasma was collected at time points following administration out to day 120 (15 weeks), except in the group that received the 400 mg dose, where data was available up to day 50. Analyses included safety, pharmacokinetics, pharmacodynamics (biomarkers), and efficacy. The drug group and the placebo group were baled in terms of age, race, ethnicity, and BMI, although there were slightly more females present in the DX-2930 (67%) vs placebo (54%) groups.

Pharmacokinetics of DX-2930

DX-2930 drug levels were measured in plasma by a validated immunoassay that used an anti-idiotypic antibody against DX-2930 (M293-D02). From the plot of mean plasma drug levels for each dose group versus days following DX-2930 administration, it was evident that drug levels were dose dependent and exhibited a prolonged half-life, typical of a human monoclonal antibody. Key pharmacokinetic observations are summarized in Table 2 and FIG. 1. First, $C_{max}$ drug levels increased with increasing dose, as expected. In addition, the $T_{max}$ following the second dose was about 20 days and the half-life was approximately 14 days. These parameters were consistent with values obtained in a phase 1a study in healthy volunteers and supported either once or twice a month dosing.

TABLE 2

| Pharmacokinetic observations | | | |
|---|---|---|---|
| Doses | $C_{max}$ (ng/ml) | $T_{max}$ (days) | $t^{1/2}$ (days) |
| 30 mg | 3895.0 (2159.8) | 17.9 (1.1) | 14.2 (0.8) |
| 100 mg | 7890.0 (2058.4) | 18.0 (0.5) | 14.6 (3.4) |
| 300 mg | 27460.0 (14542.5) | 18.2 (1.5) | 13.8 (3.3) |
| 400 mg | 45322.2 (8704.6) | 17.7 (1.0) | 15.0 (2.4) |

Values presented are the mean values for the evaluated patients with the standard deviation in parentheses.

Pharmacodynamic Activity of DX-2930: Fluorogenic Activity Assay

Figure 2:
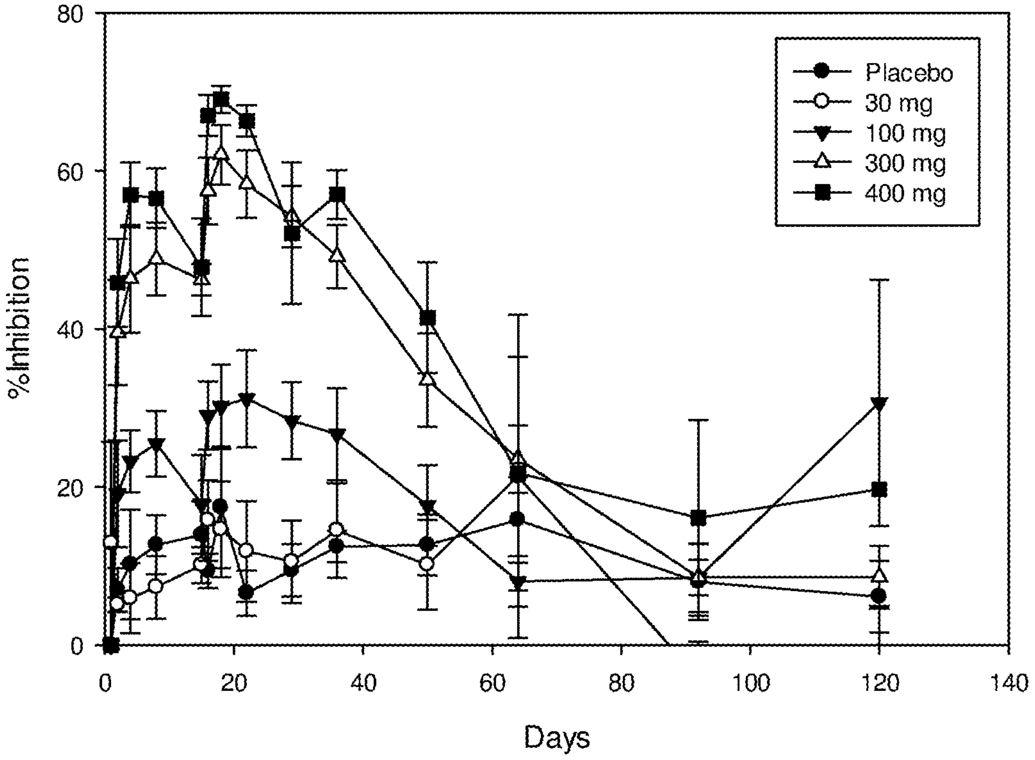
FIG. 2 shows fluorogenic activity assay of HAE patient samples from the phase 1b study.

Two different biomarker assays were used to investigate the pharmacodynamic (PD) activity of DX-2930 in HAE patient plasma. The first PD assay is referred to as the Fluorogenic Activity assay, and it provides a measure of the bioactivity of DX-2930 in citrated plasma obtained from treated patients at the same time points following dosing as used to determine the pharmacokinetic properties of DX-2930. This assay measured the amount of active plasma kallikrein that is generated in diluted plasma after activation of the contact pathway. Specifically, dilute plasma was spiked with active Factor XIIa (FXIIa) which propagates the enzymatic cascade of the contact pathway, after 2 minutes the FXIIa inhibitor Corn Trypsin Inhibitor was added to stop the reaction, and the amount of active plasma kallikrein present in the sample was measured by its ability to hydrolyze a pro-fluorescent synthetic peptide substrate. The presence of increasing levels of DX-2930 in the plasma of treated healthy volunteers (phase 1a study) or HAE patients (phase 1b study) was associated with a dose dependent reduction in the observed plasma kallikrein enzymatic rate (FIG. 2). The percent inhibition observed at each time point was calculated relative to the amount of plasma kallikrein activity in the pre-dose samples for each patient. The observed bioactivity in FIG. 2 was well correlated with the pharmacokinetic properties of DX-2930 in FIG. 1. Marked inhibition was observed in the 300 and 400 mg doses following dosing. Intermediate inhibition was observed in the 100 mg dose and no apparent inhibition was evident in the 30 mg dose.

Pharmacodynamic Activity of DX-2930: Western Blot Assay

HAE patients are deficient in C1-Inhibitor, the endogenous inhibitor of plasma kallikrein. As a result, these patients have elevated active plasma kallikrein, which converts its 1-chain high molecular weight kininogen substrate to 2-chain and bradykinin, the key mediator of pain and edema in HAE. DX-2930 is a highly potent inhibitor of active plasma kallikrein that blocks 2-chain and bradykinin generation.

Figure 3:
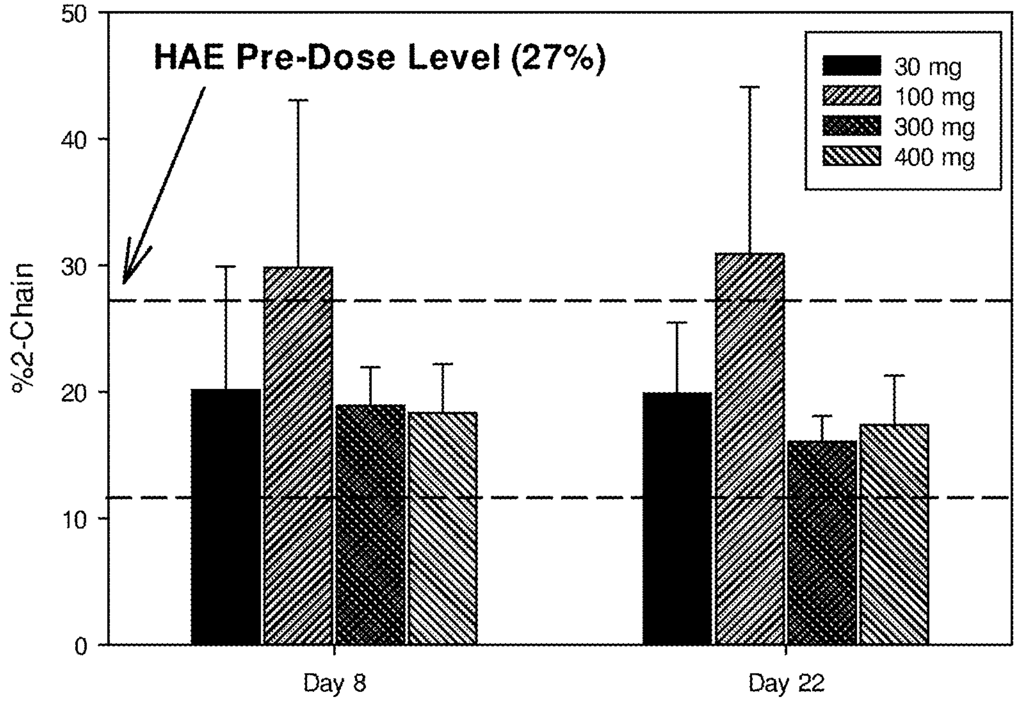
FIG. 3 is a Western blot analysis of SCAT169 plasma from HAE patients from the phase 1b study.

A Western blot assay was developed to measure the relative amounts of 1-chain and 2-chain high molecular weight kininogen in plasma in different plasma anti-coagulants and treatment conditions. FIG. 3 shows the %2-chain that was observed in HAE patient plasma collected in the presence of protease inhibitors (SCAT169 plasma). The presence of SCAT169 plasma prevented the activation of the contact system and subsequent 2-chain generation that can occur during blood collection and processing to plasma. Hence, this level of 2-chain was expected to closely match that of endogenous levels in HAE patients in in the phase 1b trial (27%) and in healthy volunteers (12%). DX-2930 treated HAE patients exhibited lower 2-chain levels as measured in samples collected either 8 or 22 days after dosing.

Figure 4:
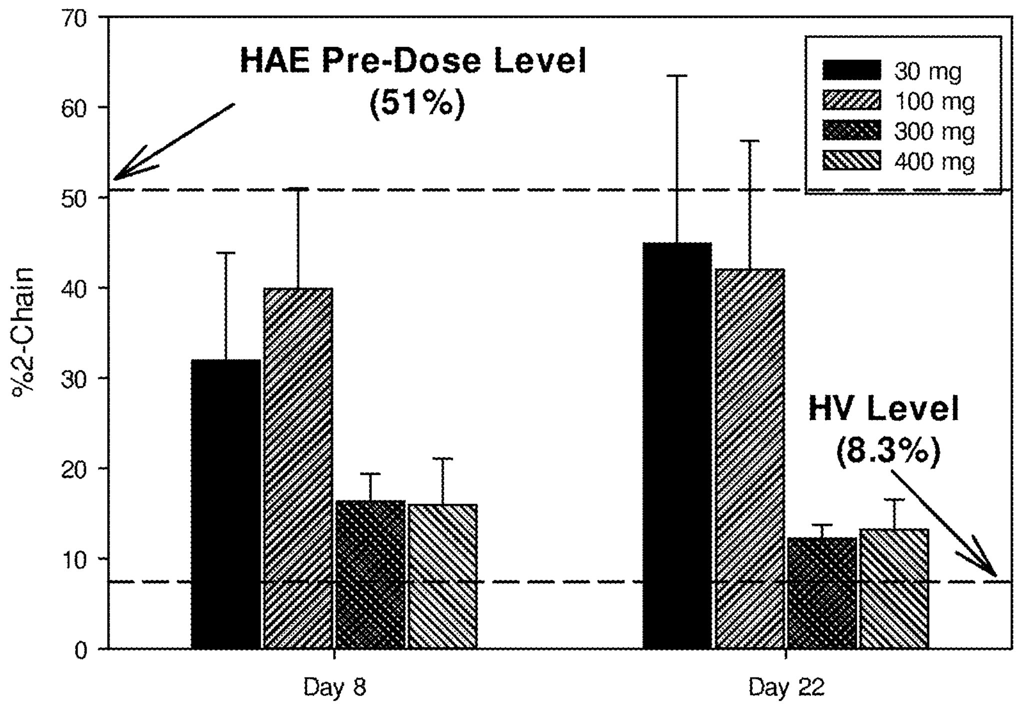
FIG. 4 is a Western blot analysis of citrated plasma from HAE patients from the phase 1b study.

In FIG. 4, pre-dose citrated plasma obtained from the HAE patients in the phase 1b trial contained approximately 52% 2-chain. In contrast, citrated plasma samples from healthy volunteers obtained in a phase 1a study contained approximately 8% 2-chain. Mean 2-chain levels in plasma of phase 1b subjects collected on days 8 and 22 were also investigated and are shown in FIG. 4. The statistically significant reduction in 2-chain levels in the 300 and 400 mg dose groups versus pre-dose levels demonstrated pharmacodynamic activity of DX-2930.

Figure 5:
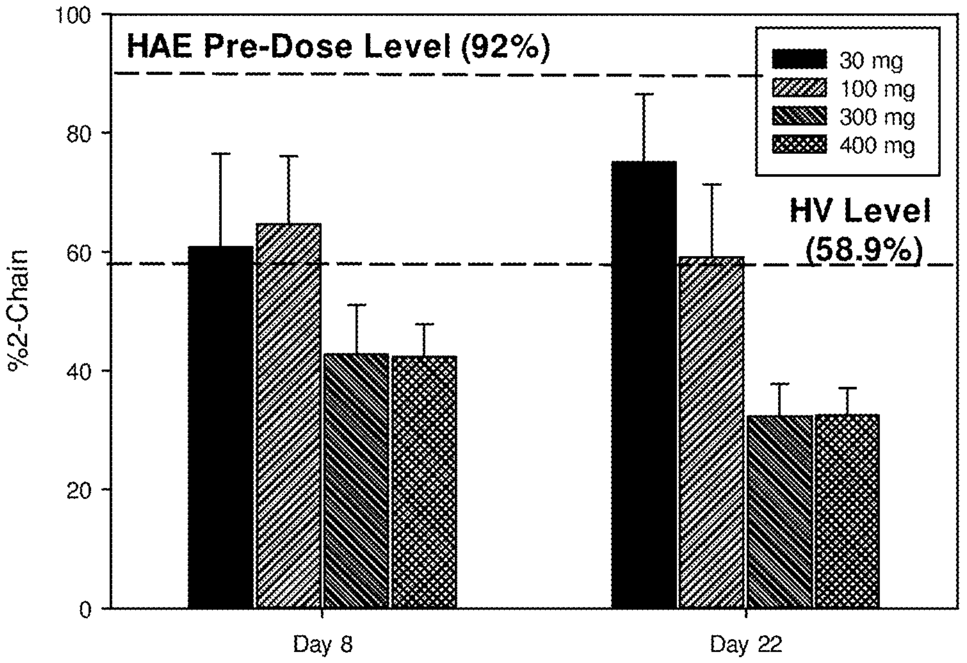
FIG. 5 is a Western blot analysis of citrated plasma activated ex vivo with FXIIa from HAE patients from the phase 1b study.

FIG. 5 shows that citrated plasma from DX-2930 dosed HAE patients exhibited less 2-chain following ex vivo activation with coagulation factor XIIa (FXIIa). The 300 and 400 mg dose groups reduced the amount of 2-chain to a level below that observed in healthy volunteers. This ex vivo activation may be considered an in vitro model of a severe HAE attack.

Both of these PD biomarker assays supported dose selection that would achieve drug levels obtained at the 300 and 400 mg dose groups.

Safety

A summary of adverse events is shown in Table 3 below. There was no imbalance in treatment emergent adverse events (TEAEs) that would indicated a safety concern of DX-2930. Most common AEs were HAE attacks, injection site pain, and headache. There were 3 severe TEAEs (injection site pain lasting 1 min, worsening headache lasting 1 minute and night sweats). No safety signals were identified for clinical laboratory abnormalities or changes from baseline, vital signs or physical examinations, or abnormalities or changes in electrocardiogram (ECG). These results suggest that DX-2930 appears to be well tolerated in HAE patients at doses up to 400 mg.

Immunogenicity 5 patients were anti-drug antibody positive (2 of the 5 had intermittent, fluctuating results). However, no positive samples were neutralizing, there was no clinical evidence of hypersensitivity, and no apparent effects on pharmacokinetics or biomarkers.

Efficacy Assessment

Figure 6:
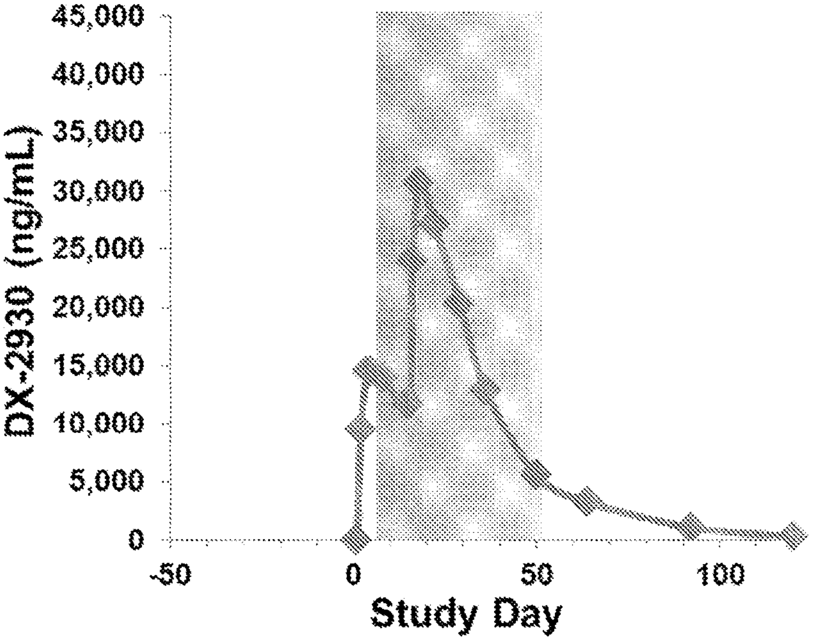
FIG. 6 shows the primary efficacy assessment period for patients in different dosing cohorts. A.: 300 mg cohort. B.: 400 mg cohort. Red bars show the interval assessed for efficacy.
Figure 6:
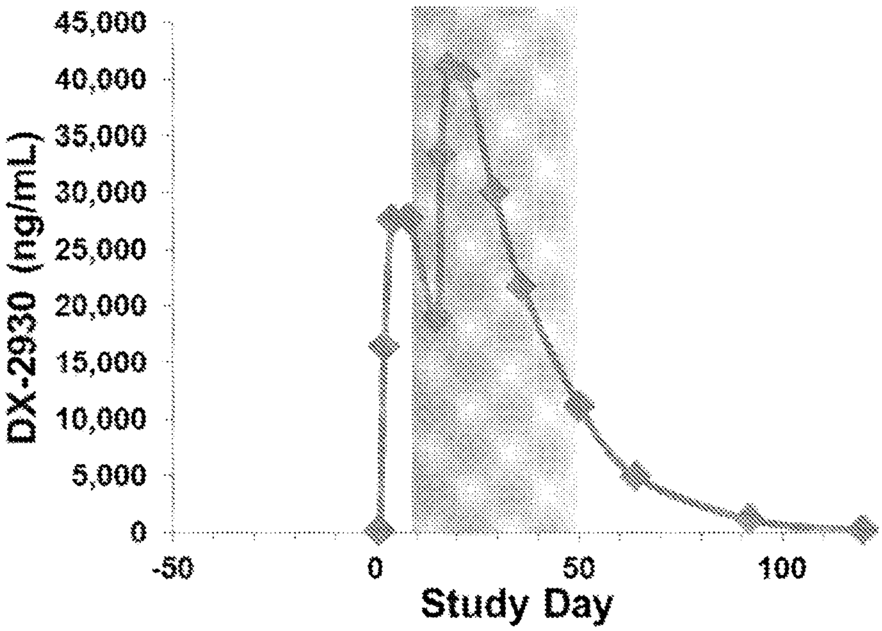

A prospective primary efficacy analysis was performed, which focused on the 300 and 400 mg doses of DX-2930, individually and combined, compared to placebo. A six week primary assessment period (Day 8 to Day 50) was used (FIGS. 6A and 6B), as PK modeling from phase 1a suggested notable drug exposure during this time interval. The primary analysis focused upon subjects with a minimum baseline history of at least 2 attacks in the past 3 months. Most of the subjects fulfilled the minimum required baseline history of at least 2 attacks in the past 3 months. Of the 13 placebo subjects, 11 met this requirement. Of the 16 subjects treated with 300 or 400 mg DX-2930, 15 met this requirement. The baseline HAE attack rates in the placebo, 300 mg, and 400 mg groups were 0.39, 0.33, and 0.55 attacks per week, respectively. The baseline rate in the combined 300 and 400 mg group was 0.49 attacks per week.

The primary approach was an intent-to-treat (ITT) analysis. A model of repeated measurements was used, with an analysis of variance (ANOVA) employing baseline attack rates as a covariate. The read-out was expressed as a percent reduction in HAE attacks by DX-2930 in comparison to the placebo attack rates, and p values were calculated.

Figure 7:
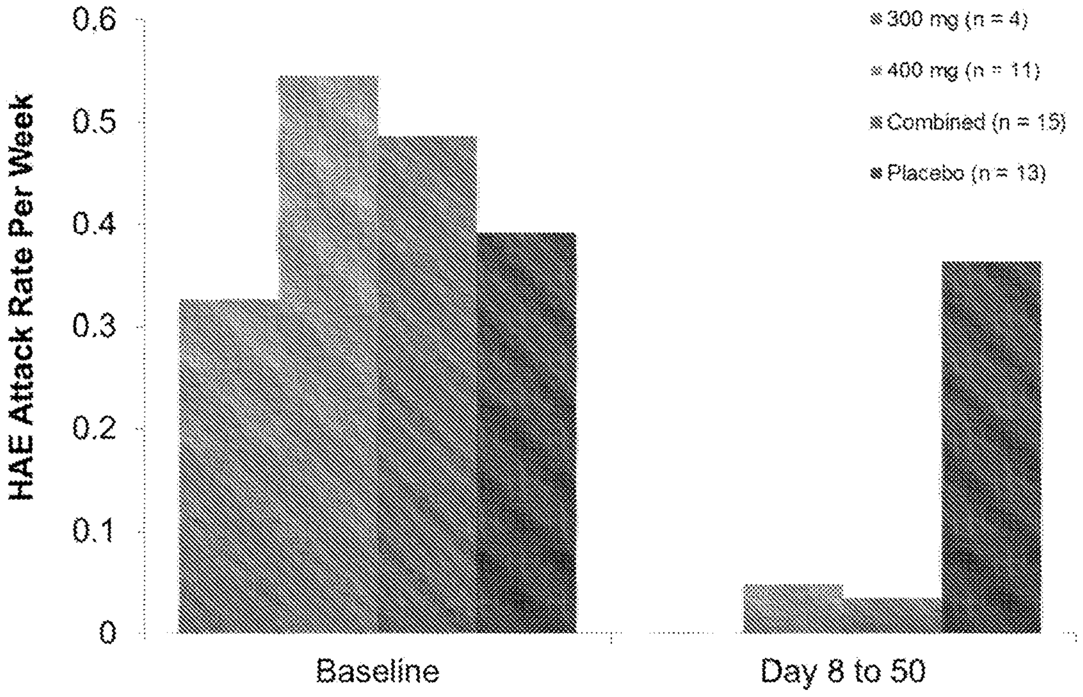
FIG. 7 shows the reduction in HAE attack rate in patients treated with 300 mg, 400 mg, combined (300 and 400 mg) or placebo. Baseline was defined as historical HAE attacks over last 3 months prior to dosing. The data includes patients with a baseline rate of ≥2 attacks in the last 3 months. Day 8 to 50 attack rates were unadjusted for baseline rates. Percent reduction in HAE attack rate over placebo and p-value were calculated based upon Mixed Model Repeated Measurements with Analysis of Variance (baseline attack rate as covariate) and assuming Poisson distribution.

Results of the efficacy assessment are shown in Table 4 and 5 and in FIG. 7, which both show a reduction in HAE attack rate with the 300 and 400 mg doses of DX-2930, individually and combined, compared to the placebo. In particular, 13 of the 15 DX-2930 subjects treated with 300 or 400 mg were attack-free for the duration of the study, whereas for the placebo group, only 3 of the 11 subjects were attack-free.

TABLE 3

Summary of treatment adverse events

| | DX-2930 30 mg (N = 4) | DX-2930 100 mg (N = 4) | DX-2930 300 mg (N = 5) | DX-2930 400 mg (N = 11) | All DX-2930 treated (N = 24) | Placebo (N = 13) |
|---|---|---|---|---|---|---|
| TEAEs* | 1 | 3 | 2 | 8 | 14 (58%) | 10 (77%) |
| Deaths or subject discontinuations | 0 | 0 | 0 | 0 | 0 | 0 |
| Serious adverse events | 0 | 0 | 0 | 0 | 0 | 1 (8%) |
| Severe TEAEs | 1 | 0 | 2 | 2 | 5 (21%) | 5 (39%) |
| Related TEAEs** | 1 | 2 | 0 | 4 | 7 (29%) | 5 (39%) |

*TEAE: Treatment Emergent Adverse Events. An AE is treatment emergent if the onset time is after administration of study drug through the Day 120 post dose final follow-up visit, or in the event that onset time precedes study drug administration, the AE increases in severity during the 120 day post dose follow-up period.

**Treatment-related AEs: Relatedness of AEs to study drug was assessed by a blinded investigator.

TABLE 4

| Reduction in HAE attack rate from day 8 to 50 | DX-2930 300 mg (N = 4) | DX-2930 400 mg (N = 11) | DX-2930 Combined 300 and 400 mg (N = 15) |
|---|---|---|---|
| % Reduction vs placebo | 100 | 88 | 91 |
| P-value vs placebo* | <0.0001 | 0.005 | 0.0012 |

Note:
Only subjects who have a baseline attack rate of at least 2 attacks in the last 3 months were included.
*Mixed Model Repeated Measurements with Analysis of Variance (baseline attack frequency as covariate) and assuming Poisson distribution.

TABLE 5

| Proportion of subjects who were attack-free | DX-2930 300 mg (N = 4) | DX-2930 400 mg (N = 11) | DX-2930 Combined 300 and 400 mg (N = 15) | Placebo (N = 11) |
|---|---|---|---|---|
| Attack-free subjects (Day 8 to 50) | 4/4 (100%) p = 0.026 | 9/11 (82%) p = 0.030 | 13/15 (87%) p = 0.004 | 3/11 (27%) |

Among the placebo subjects, there were a total of 24 attacks during the primary efficacy assessment period. Of these 24 attacks, the primary attack location was abdominal in 13 and laryngeal in 1 of them. 10 of the attacks were severe and 6 were moderate. Acute treatment for the attacks was received in 22 of the 24 attacks.

Among subjects treated with 300 or 400 mg DX-2930, one subject treated with 400 mg had a single HAE attack. This attack was peripheral, mild, lasted 8 hours, and did not require any acute treatment. The other 400 mg DX-2930-treated subject experiencing attacks had two peripheral attacks. One attack was moderate and the other was severe; both attacks were treated with acute therapy. A summary of the characteristics of the HAL attacks is shown in Table 6.

TABLE 6

| Characteristics of HAE attacks (Day 8 to 50) | DX-2930 300 mg (N = 4) | DX-2930 400 mg (N = 11) | Placebo (N = 11) |
|---|---|---|---|
| Attacks | 0 | 3 | 24 |
| Primary Attack Location | | | |
| Peripheral | 0 | 3 | 10 |
| Abdominal | 0 | 0 | 13 |
| Laryngeal | 0 | 0 | 1 |
| Attack Severity | | | |
| Mild | 0 | 1 | 8 |
| Moderate | 0 | 1 | 6 |
| Severe | 0 | 1 | 10 |
| Acute attacks requiring treatment | 0 | 2 | 22 |

Next, a modified intent-to-treat (mITT) post-hoc analysis was undertaken. The ITT population was used except 2 subjects were excluded (one subject that did not receive 2 administrations and 1 subject that did not have HAL type 1 or type 2). Results of the modified analysis are shown in Table 7. In this modified intent-to-treat analysis, from Day 8 to Day 50 in comparison to placebo, the 300 mg DX-2930 group had a 100% reduction in attacks with a p value of less than 0.0001. The 400 mg DX-2930 group had a 95% reduction in attacks with a p value of 0.0022. The combined 300 and 400 mg DX-2930 group had a 97% reduction in HAE attacks, with a p value of 0.0007.

TABLE 7

| Primary efficacy analysis (Day 8 to 50) (modified intent-to-treat analysis) | DX-2930 300 mg (N = 4) | DX-2930 400 mg (N = 9) | DX-2930 Combined 300 and 400 mg (N = 13) |
|---|---|---|---|
| % Reduction vs placebo | 100 | 95 | 97 |
| P-value vs placebo* | <0.0001 | 0.0022 | 0.0007 |

Note:
Only subjects who have a baseline attack rate of at least 2 attacks in the last 3 months are included. MITT population excludes 2 subjects, one subject without type I or II HAE and one subject who received only 1 administration of DX-2930.
*Mixed Model Repeated Measurements with Analysis of Variance (baseline attack frequency as covariate) and assuming Poisson distribution.

The incidence of HAE attacks in relation to drug exposure over time was also evaluated. Without wishing to be bound by theory, the hypothesis was that higher drug levels should be correlated with prevention of HAE attacks, meaning (a) that before dosing as well as in the few days after dosing, attacks should be observed, (b) that as drug levels accumulate, attacks should become rare or even absent, and (c) that as the drug levels decline, attacks should re-emerge. The results of this evaluation are shown in FIGS. 8-13.

Figure 8:
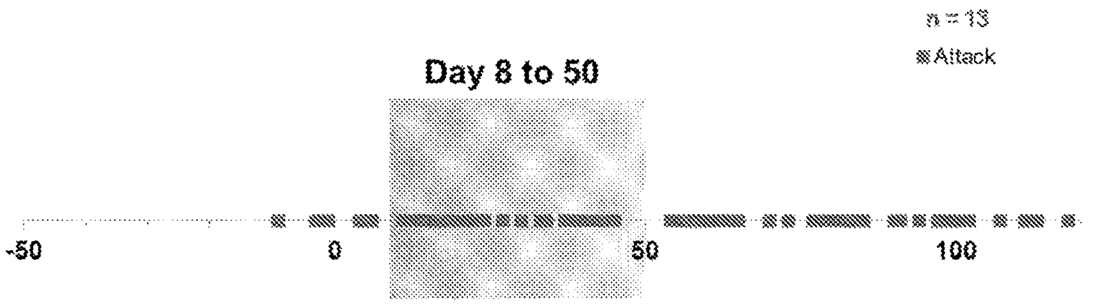
FIG. 8 shows the incidence of HAE attacks in placebo-treated subjects. The X-axis shows the study day number.

In the placebo group high incidence of attacks was evident (FIG. 8). These events were distributed throughout the entire duration of the study without any particular pattern.

Figure 9:
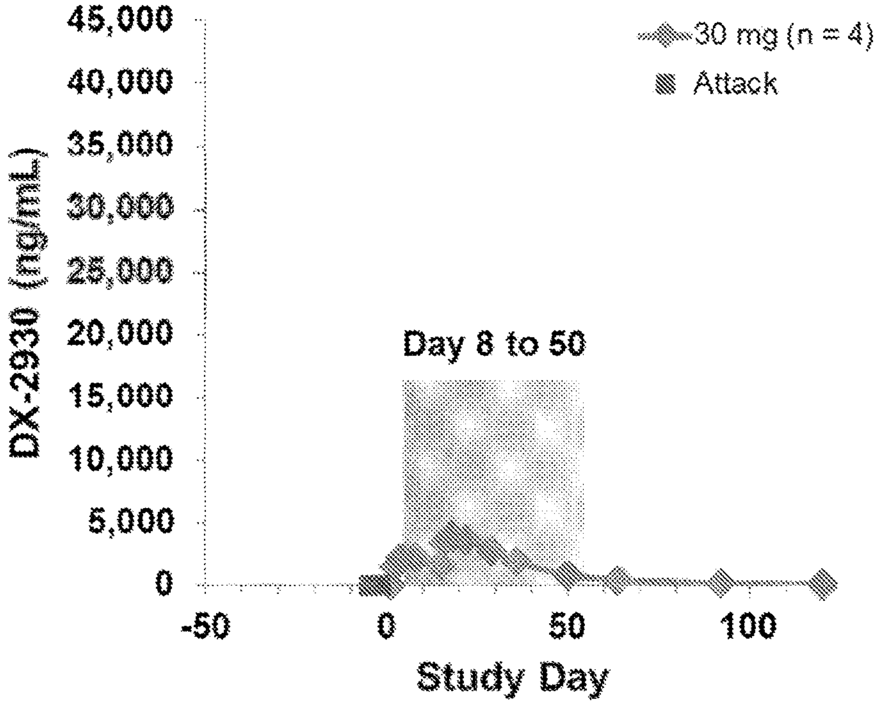
FIG. 9 shows the mean DX-2930 concentration and HAE attack incidence following 30 mg dosage.
Figure 10:
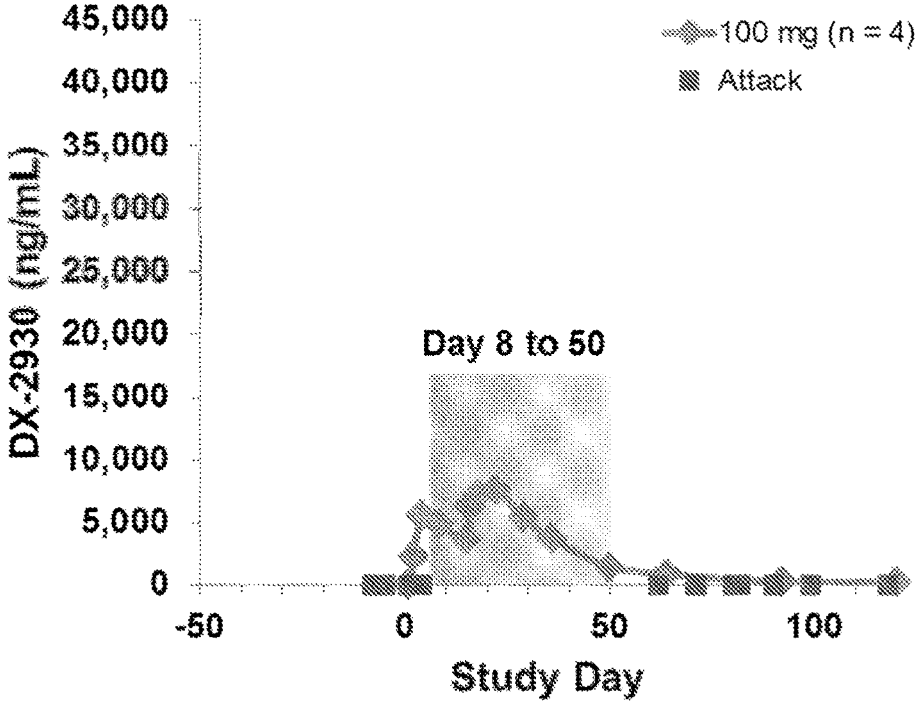
FIG. 10 shows the mean DX-2930 concentration and HAE attack incidence following 100 mg dosage.
Figure 11:
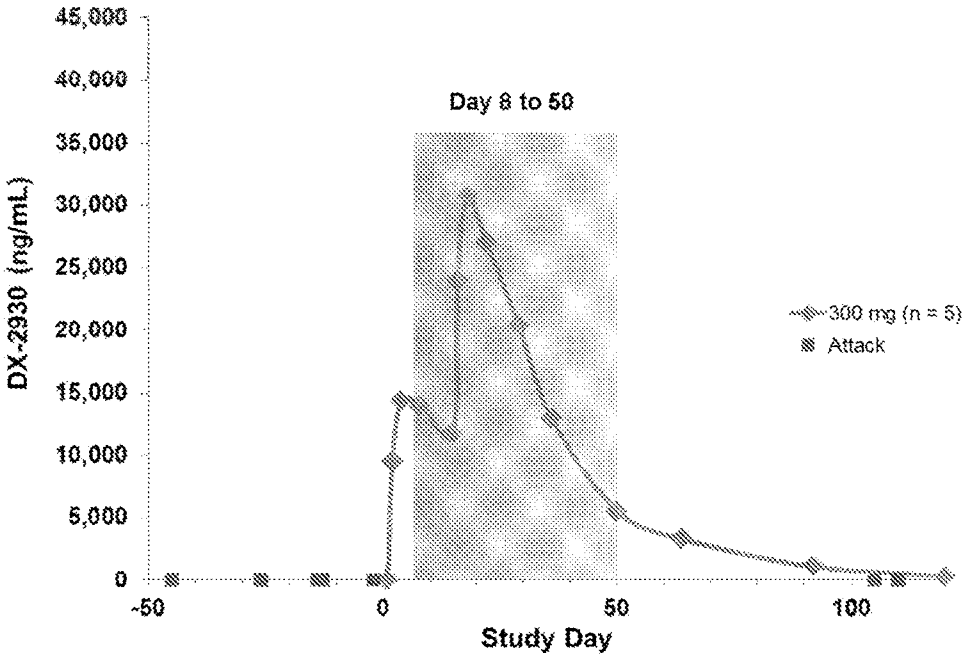
FIG. 11 shows the mean DX-2930 concentration and HAE attack incidence following 300 mg dosage.
Figure 12:
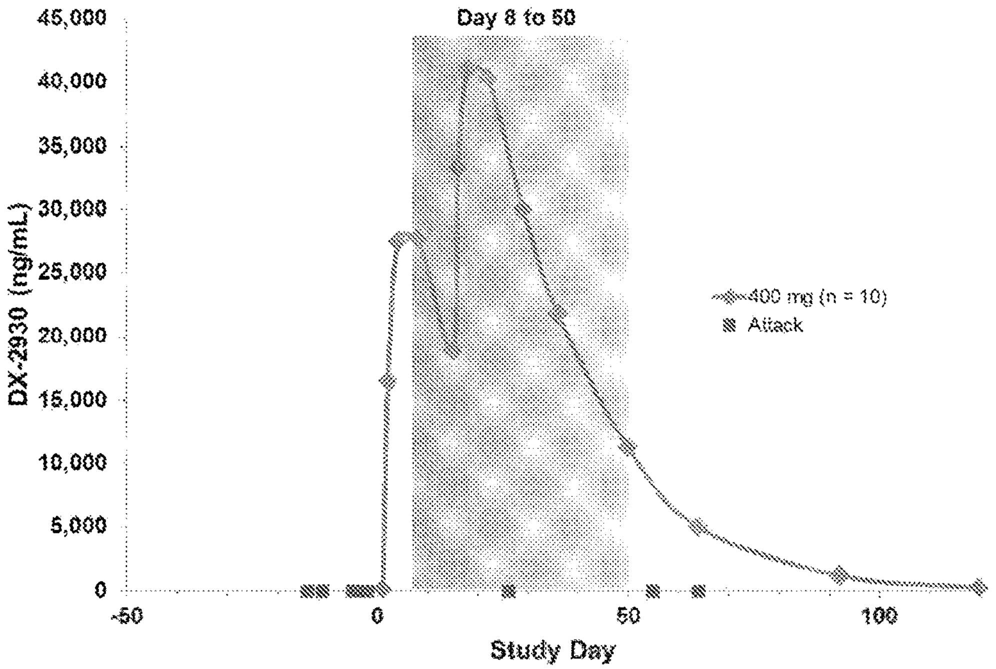
FIG. 12 shows the mean DX-2930 concentration and HAE attack incidence following 400 mg dosage. Excludes one patient who received only one dose (in order to derive the mean pharmacokinetic curve).

In the 30 and 100 mg DX-2930 groups, no attacks occurred from Day 8 to Day 50 (FIGS. 9 and 10). However, the baseline attack rates for these groups were relatively lower and the pharmacodynamic effect for the 30 mg group was not appreciably different from that for placebo. In the 300 mg DX-2930 group, there were attacks that occurred prior to dosing. As drug levels rose, the subjects became attack-free and as drug levels declined, attacks re-emerged (FIG. 11). A similar pattern was also observed in the 400 mg DX-2930 group (FIG. 12). Attack incidence substantially decreased during a period of notable drug exposure, particularly within the Day 8 to Day 50 time interval. This period was bracketed by attacks occurring during times of lower drug exposure, either prior to drug accumulation or as drug levels waned. These results show that there is a clear association between DX-2930 drug exposure and prevention of HAE attacks.

To further assess the efficacy of DX-2930, the therapeutic effects of DX-2930 were also observed in HAE patients with high baseline attack rates were explored. Subjects with at least 9 attacks in the past 3 months prior to dosing were identified and evaluated. There were 6 such subjects—1 treated with placebo, 1 treated with 300 mg DX-2930, and 4 treated with 400 mg DX-2930.

Figure 13:
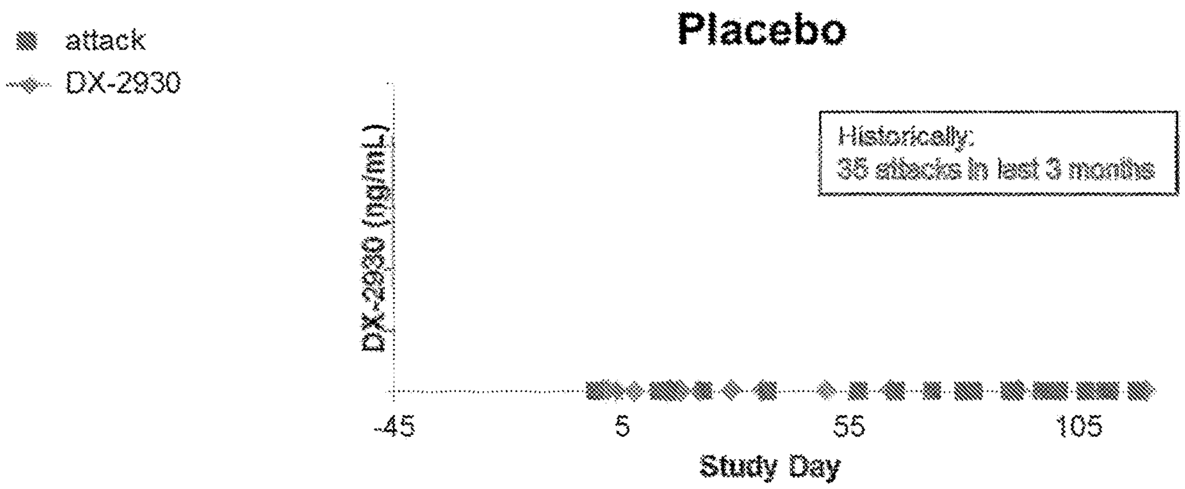
FIG. 13 shows DX-2930 concentration and HAE attacks in patients with historical attack rate ≥9 attacks/3 months. A.: a placebo patient. B.: a patient treated with 300 mg. and C.-F.: patients treated with 400 mg.
Figure 13:
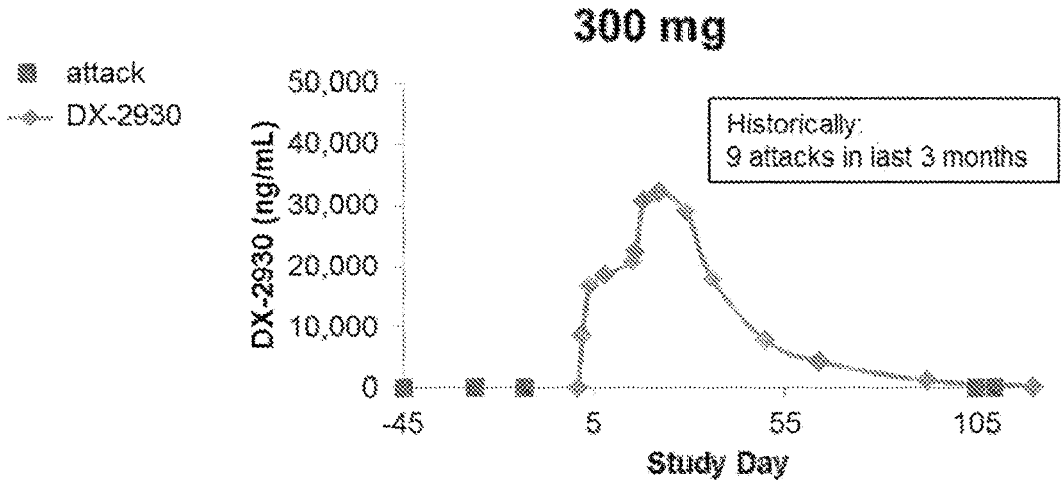
Figure 13:
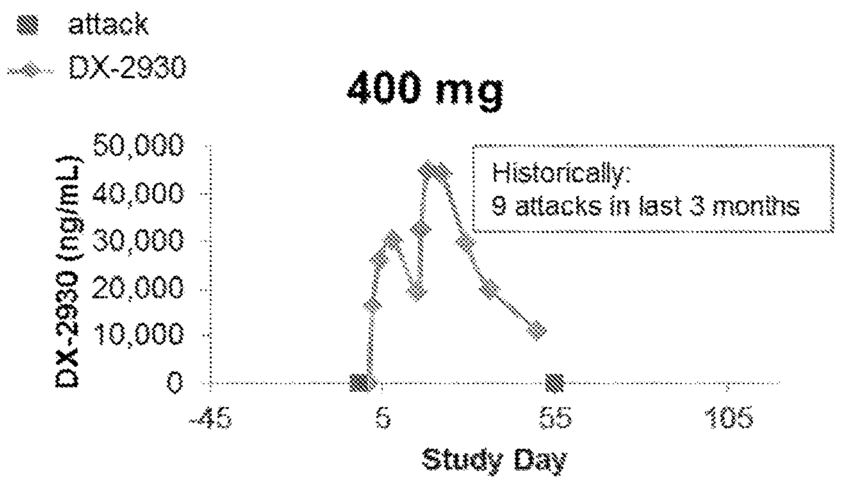
Figure 13:
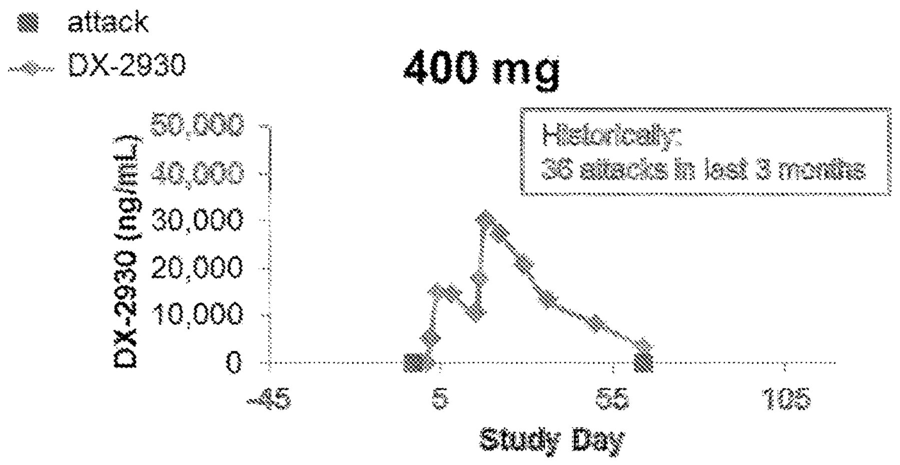
Figure 13:
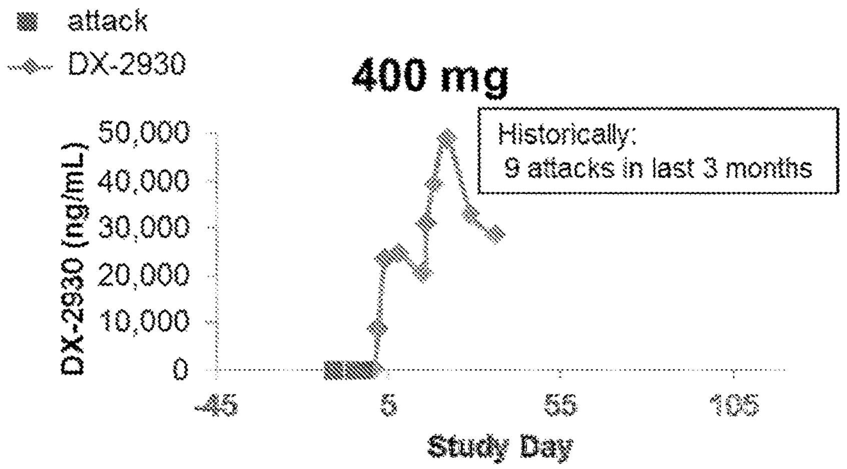
Figure 13:
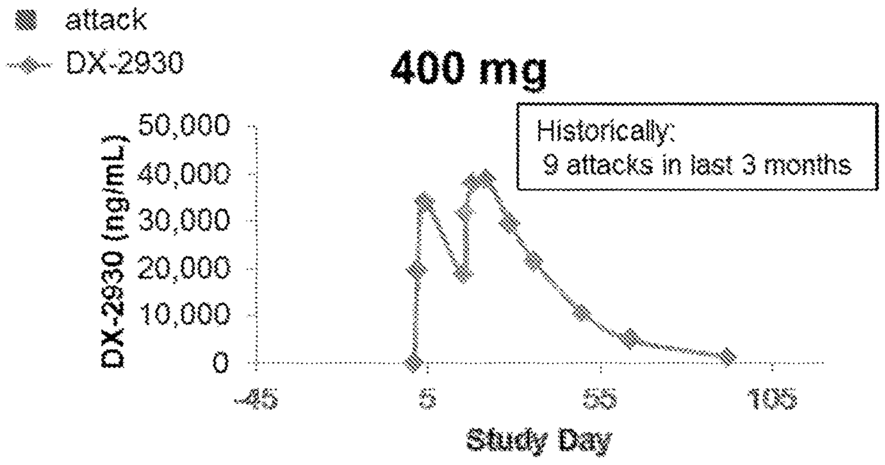

In the placebo subject, attacks occurred throughout the observation period at a high rate (FIG. 13, panel A). In contrast, the subject treated with 300 mg DX-2930 was attack-free when drug levels were high. (FIG. 13, panel B).

In the four subjects with high baseline attack rates who were treated with 400 mg DX-2930, all four of these subjects were attack-free during the Day 8 to Day 50 time interval (FIGS. 13, panels C-F). This included one subject with a very high baseline rate of 36 attacks in the past 3 months. The pattern of attacks in these DX-2930-treated subjects was consistent with that seen in the 300 and 400 mg groups overall. These individuals did not experience any attacks when drug levels were high. Attacks only occurred when drug levels were low, either prior to meaningful drug accumulation or after drug levels declined.

From these data, it was observed that the therapeutic effect of DX-2930 was also evident in HAE patients with high baseline attack rates.

In summary, this study shows (a) that there were no apparent safety signals for DX-2930, (b) that the PK profile was consistent overall with a monoclonal antibody and supported a regimen of dosing once every 2 weeks or even less frequently, (c) that pharmacodynamic data demonstrated that DX-2930 normalizes the aberrant instability of HAE plasma, at least in the context of the kininogen biomarker assays, and (d) that a highly statistically significant finding of HAE attack prevention by DX-2930 was observed. Specifically, in comparison to placebo, there were 100% and 88% reduction in attacks by the 300 and 400 mg DX-2930 treatment groups respectively. This clinical effect was logically associated with drug exposure over time and was also observed in the subset of patients with high baseline attack rates.

These data demonstrate proof of concept for DX-2930 in long-term prophylaxis against HAE attacks.

Example 2: Pharmacodynamic Effect of DX-2930 on Plasma Kallikrein in Hereditary Angioedema Patients Attacks of hereditary angioedema (HAE) result from uncontrolled contact system activation which generates a burst of plasma kallikrein (pKal) that cleaves high-molecular-weight kininogen (HMWK) to produce 2-chain HMWK and the edema-inducing peptide, bradykinin. DX-2930 is a human monoclonal antibody inhibitor of pKal in development for the prevention of HAE attacks. The pharmacodynamic bioactivity of DX-2930 was assessed in subjects with HAE.

As described in Example 1 above, the phase 1b multi-center, double-blind study, randomized subjects with Type 1 or 2 HAE to receive 2 subcutaneous doses of DX-2930 in dose groups of 30, 100, 300 or 400 mg (n=4, 4, 5, 11) or placebo (n=13). Blood samples were obtained prior to and following administration of study drug (Days 1, 8, 22, 64, 92, 120). The ability of DX-2930 to inhibit pKal in basal and FXIIA-activated citrated plasma was assessed using Western blot for 2-chain HMWK.

The results obtained from this study showed that mean 2-chain HMWK levels were significantly reduced and essentially normalized in the 300 and 400 mg dose groups on Days 8 and 22, and on Days 8, 22 and 50, respectively, when compared to placebo treated subjects. Treatment with 300 or 400 mg DX-2930 also attenuated the burst in 2-chain generation to levels at or below that observed in healthy individuals in FXIIA-activated samples. Levels of 2-chain HMWK did not differ from pre-dose plasma samples in either activated or inactivated samples collected on Days 64, 92 or 120 following DX-2930, which correspond to periods of low drug exposure.

In sum, this study indicates that DX-2930 inhibits pKal in a dose and time-dependent manner in HAE patients.

Example 3: Relationship Between Drug Exposure and Clinical Response Observed in the Phase 1b Study of DX-2930 in Subjects with Hereditary Angioedema DX-2930 is a human monoclonal antibody inhibitor of plasma kallikrein in development for the prevention of hereditary angioedema (HAE) attacks. Data from the phase 1b study of DX-2930 in HAE subjects as described in Example 1 above was analyzed to characterize the relationship between drug exposure and clinical response.

This phase 1b multi-center, double-blind study, randomized subjects with Type 1 or 2 HAE to receive 2 subcutaneous doses of DX-2930 in dose groups of 30, 100, 300 or 400 mg (n=4, 4, 5, 11) or placebo (n=13). In this post-hoc analysis, the incidence of HAE attacks was evaluated in relation to drug exposure over time. In addition, a post-hoc modified intent-to-treat efficacy analysis (MITT) was conducted to assess clinical effect in the context of subjects receiving the full dose regimen of DX-2930.

Placebo-treated subjects reported HAE attacks throughout the study (9 subjects, 65 HAE attacks). In the 300 and 400 mg dose groups, HAE attacks were reported prior to or just after initial dosing. When drug levels were high (Day 8 to 50), all but 1 subject was attack-free. As drug levels waned, attacks re-emerged. In the MITT efficacy analysis, from Day 8 to 50 in comparison to placebo, the 300 and 400 mg DX-2930 groups had a 100% ($P<0.0001$) and 95% ($P=0.0022$) reduction in attacks, respectively.

Thus, this study indicates that HAE attacks were substantially decreased or were eliminated during periods of notable drug exposure consistent with the suggestion that higher drug levels should correlate with HAE attack prevention.

Example 4: Modeling and Analyses to Identify Potential Dosing Regimens of DX-2930 for the Long-Term Prophylaxis of Hereditary Angioedema DX-2930 is a human monoclonal antibody inhibitor of plasma kallikrein in development for the prevention of hereditary angioedema (HAE) attacks. Data from the Phase 1 studies of DX-2930 as described in Example 1 above were modeled and analyzed to identify potential dosing regimens.

Pharmacokinetic, pharmacodynamic and efficacy data from the Phase 1 clinical studies were examined. The incidence of HAE attacks was evaluated in relation to plasma drug concentrations to estimate steady-state trough drug levels necessary to prevent attacks.

Dosing regimens of 300 mg DX-2930 every 2 (q2) or 4 (q4) weeks, and 150 mg q4 weeks are being considered for the pivotal efficacy study. Pharmacokinetic modeling predicts steady-state trough plasma concentrations of 27,000, 9,500, and 4,750 ng/mL, respectively. In the Phase 1b study, at 27,000 ng/mL (corresponding to approximate drug levels at Day 22 for 300 mg DX-2930), 2-chain high-molecular-weight kininogen was suppressed to a level approximating that observed in healthy subjects. Three-hundred mg q2 is therefore predicted to normalize the instability of HAE plasma at steady state. As successful HAE prophylaxis may not require such a high level of pharmacodynamic effect, an analysis of clinical effect in relation to plasma drug concentrations was also conducted. In the Phase 1b study following DX-2930 treatment, 24/25 attacks (96%), 21/25 (84%), and 18/25 attacks (72%) occurred below plasma concentrations of 27,000, 9,500, and 4,750 ng/mL, respectively, suggesting a meaningful range of clinical response is associated with this range of drug exposure.

In this analysis, potential dosing regimens of DX-2930 were identified for further clinical investigation in the pivotal efficacy study.

Example 5: Hereditary Angioedema is Associated with Neuropathic Pain, Systemic Lupus Erythematosis and Systemic Mastocytosis in an Analysis of a Health Analytics Claims Database The plasma kallikrein kinin system (KKS) has been associated with a variety of diseases in addition to being a key mediator of hereditary angioedema (HAE). It was explored in this study whether HAE patients were predisposed to develop such KKS associated diseases: abdominal aortic aneurysm, anaphylaxis, cardiac vasoplegia syndrome, Crohn's disease, diabetic macular edema, idiopathic anaphylaxis, neuropathic pain, psoriasis, psoriatic arthritis, retinopathy, rheumatoid arthritis, systemic lupus erythematosus (SLE), system mastocytosis, systemic vasculitis, thrombotic cerebrovascular accident, and ulcerative colitis.

The Truven MarketScan Database containing individual-level claims data from medical payers and Medicare supplemental plans for 80 million lives in the U.S. from January 2010 through July 2014 was utilized in this study. Within this dataset, an HAE population (n=1063) and 2 control populations: an angioedema population (n=138,851) and the general population (n=79,971,098) exclusive of HAE patients were defined using a combination of ICD-9 and prescription drug codes. Claims for comorbid diseases were identified and compared across the populations with calculated odds ratios and 95% confidence intervals (CI).

As shown in the Table 8 below, in the HAL population, SLE was observed 2.3 times more often (OR 2.30, 95% CJ: 1.47-3.59) than the angioedema control population. Neuropathic pain was observed 1.45 times (OR 1.45, 95% CJ: 1.01-2.09) and systemic mastocytosis 4.79 times (OR 4.79, 95% CJ: 1.51-15.18) more often than the angioedema control population.

TABLE 8

Association between HAE and Other KSS-related Diseases

| Associated Disease | HAE Population N = 1063 | % | Angioedema Control N = 138,851 | % | Odds Ratio (95% CI) |
|---|---|---|---|---|---|
| Abnormal aortic aneurysm (AAA) | 6 | 0.56 | 583 | 0.42 | 1.35 (0.60, 3.02) |
| Anaphylaxis | 86 | 8.09 | 15,293 | 11.01 | 0.72 (0.57, 0.89) |
| Cardiac vasoplegia syndrome | 2 | 0.19 | 88 | 0.06 | 2.97 (0.73, 12.09) |
| Crohn's disease | 6 | 0.56 | 848 | 0.61 | 0.92 (0.41, 2.07) |
| Diabetic macular edema | 2 | 0.19 | 140 | 0.10 | 1.87 (0.46, 7.55) |
| Idiopathic anaphylaxis | 59 | 5.55 | 8,442 | 6.08 | 0.91 (0.70, 1.18) |
| Neuropathic pain | 30 | 2.82 | 2,726 | 1.96 | 1.45 (1.01, 2.09) |
| Psoriasis | 14 | 1.32 | 2,182 | 1.57 | 0.84 (0.49, 1.42) |
| Psoriatic arthritis | 4 | 0.38 | 382 | 0.28 | 1.37 (0.51, 3.67) |
| Retinopathy | 2 | 0.19 | 85 | 0.06 | 3.08 (0.76, 12.52) |
| Rheumatoid arthritis | 30 | 2.82 | 3,093 | 2.23 | 1.27 (0.89, 1.84) |
| Systemic lupus erythematosus | 20 | 1.88 | 1,148 | 0.83 | 2.30 (1.47, 3.59) |
| Systemic mastocytosis | 3 | 0.28 | 82 | 0.06 | 4.79 (1.51, 15.18) |
| Systemic vasculitis | 2 | 0.19 | 189 | 0.14 | 1.38 (0.34, 5.58) |
| Thrombo cerebrovasc accident (CVA) | 2 | 0.19 | 375 | 0.27 | 0.70 (0.17, 2.80) |
| Ulcerative colitis | 9 | 0.85 | 902 | 0.65 | 1.31 (0.68, 2.53) |

In sum, an analysis of a large longitudinal claims database revealed that comorbid diseases of SLE, neuropathic pain and systemic mastocytosis had a greater representation in HAE patients than other types of angioedema, suggesting that activity of the KKS may be contributing to the manifestations of these diseases. Accordingly, patients having or at risk for HAE may be predisposed to KKS-associated diseases, including neuropathic pain, systemic lupus erythrmatosus, and systemic mastocytosis. Thus, treatment with a pKal inhibitor, such as DX-2930 may reduce the risk for the development of such a KKS-associated disease.

Figure 14:
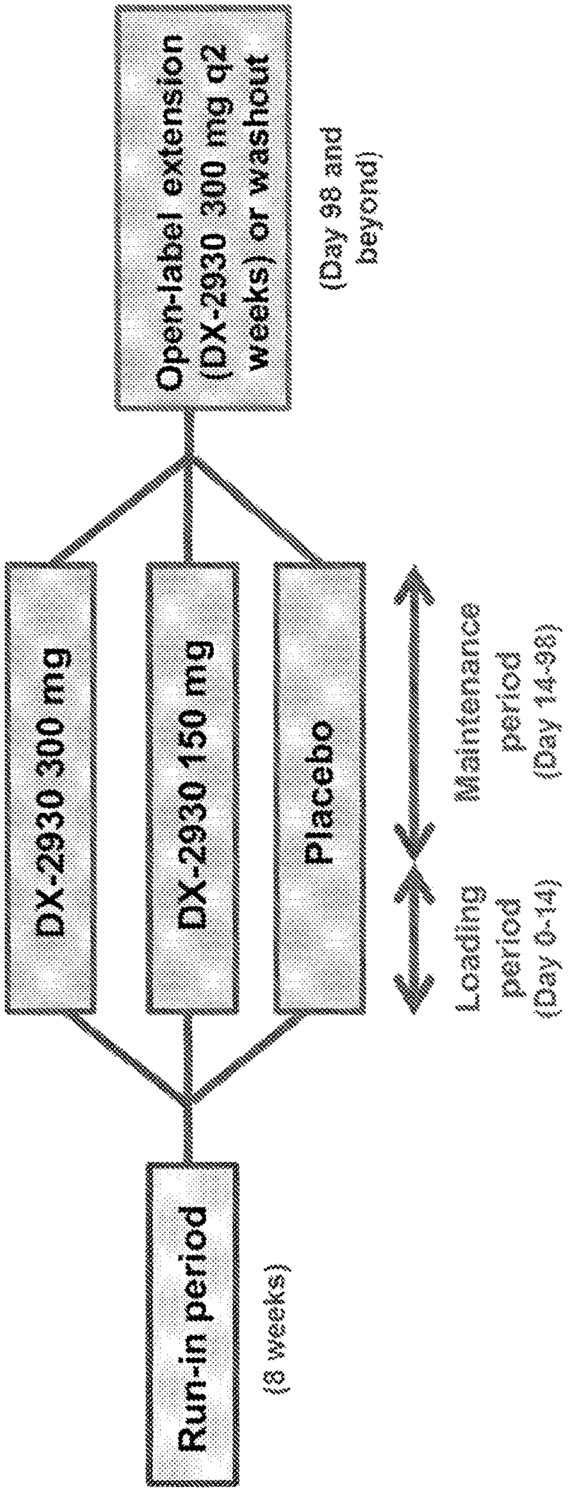
FIG. 14 shows an exemplary dosing regimen comprising a loading period and a maintenance period, which may be followed by an extended treatment period or a washout period.

Example 6: A Double-Blind Study Including a Load Period and a Maintenance Period A randomized, double-blind, placebo-controlled, parallel arm study is carried out. Patients are selected for having HAE type I or II patients with at least 1 attack per 4 weeks. A run-in period is used to evaluate baseline HAE attack rate. The patients are subjected to a 1:1:1 randomization into 3 different treatment arms (300 mg DX-2930, 150 mg DX-2930, or placebo) which are administered by subcutaneous injection. The study is designed with a load period and a maintenance period (FIG. 14). Subjects are treated on Days 0, 7, and 14 during the loading period, followed by dosing every 2 weeks during the maintenance period (Days 28, 42, 56, 70, and 84).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of preventing hereditary angioedema (HAE) attack or reducing the rate of HAE attack, the method comprising:

administering to a subject in need thereof 300 mg of an antibody that binds to active plasma kallikrein, wherein the antibody comprises a heavy chain complementarity determining region (HC CDR) 1 set forth in SEQ ID NO: 5, a HC CDR2 set forth in SEQ ID NO: 6, a HC CDR3 set forth in SEQ ID NO: 7, a light chain CDR (LC CDR) 1 set forth in SEQ ID NO: 8, a LC CDR2 set forth in SEQ ID NO: 9, and LC CDR3 set forth in SEQ ID NO: 10, wherein the antibody is formulated in 30 mM sodium phosphate, citric acid, 50 mM histidine, 90 mM sodium chloride, and 0.01% Tween 80, pH 6.0, wherein the antibody is administered every two to four weeks for at least two times, wherein the subject is a human patient who has experienced at least nine HAE attacks within three months prior to the first administration of the antibody, and wherein administration of the antibody reduces cleaved kininogen of the subject to a level comparable to or below the level of healthy subjects.

2. The method of claim 1, wherein the antibody comprises a heavy chain variable region set forth in SEQ ID NO: 3 and a light chain variable region set forth in SEQ ID NO: 4.

3. The method of claim 1, wherein the antibody is a full length antibody or an antigen-binding fragment thereof.

4. The method of claim 3, wherein the antibody comprises a heavy chain set forth as EVQLLESGGGLVQPGGSLRLS-CAASGFTFSHYIMMWVRQAPGKGLEWVSGIYSSG-GITV YADSVKGRFTISRDNSKNTLYLQMNSLRAED-TAVYYCAYRRIGVPRRDEFDIWGQGTM VTVSSASTKGPSVFPLAPSSKSTSGGTAAL-GCLVKDYFPEPVTVSWNSGALTSGVHTFPA VLQSSG-LYSLSSVVTVPSSSLGTQTYICNVNHKPSNTKVD KRVEPKSCDKTHTCPPCPAP ELLGGPSVFLFPPKPKDTLMISRTPE-VTCVVVDVSHEDPEVKFNWYVDGVEVHNAKTKP REEQYNSTYRVVSVLTVLHQDWLNGKEYKCK VSNKALPAPIEKTISKAKGQPREPQVY TLPPSREEMT-KNQVSLTCLVKGFYPSDIAVEWESNGQPEN-NYKTTPPVLDSDGSFFL YSK LTVDKSRWQQGNVFSCSVMHEALHNHYTQKSLSL-SPG (SEQ ID NO: 11) and a light chain set forth as DIQMTQSPSTLSASVGDRVTITCRASQSISS-WLAWYQQKPGKAPKLLIYKASTLESGVPS RFSGSGSGTEFTLTISSLQPDDFA-TYYCQQYNTYWTFGQGTKVEIKRTVAAPSVFIFPPSD EQLKSGTASVVCLLNNFYPREAKVQWKVD-NALQSGNSQESVTEQDSKDSTYSLSSTLTL SKADYEKHKVYACEVTHQGLSSPVTKSFNRGEC (SEQ ID NO: 12).

5. The method of claim 1, wherein the antibody is administered subcutaneously.

6. The method of claim 1, wherein the subject is a human patient having type I or type II HAE.

7. The method of claim 1, wherein the antibody is administered to the subject every two weeks or every four weeks.

8. A method of treating hereditary angioedema (HAE), the method comprising:

administering to a subject in need thereof 300 mg of an antibody that binds to active plasma kallikrein, wherein the antibody comprises a heavy chain complementarity determining region (HC CDR) 1 set forth in SEQ ID NO: 5, a HC CDR2 set forth in SEQ ID NO: 6, a HC CDR3 set forth in SEQ ID NO: 7, a light chain CDR (LC CDR) 1 set forth in SEQ ID NO: 8, a LC CDR2 set forth in SEQ ID NO: 9, and LC CDR3 set forth in SEQ ID NO: 10, wherein the antibody is formulated in 30 mM sodium phosphate, citric acid, 50 mM histidine, 90 mM sodium chloride, and 0.01% Tween 80, pH 6.0, and the antibody being first administered for a loading period, and then for a maintenance period;

wherein in the loading period, the antibody is administered once every week, and wherein in the maintenance period, the antibody is administered once every two to four weeks;

wherein the subject is a human patient who has experienced at least nine HAE attacks within three months prior to the first administration of the antibody; and wherein administration of the antibody reduces cleaved kininogen of the subject to a level comparable to or below the level of healthy subjects.

9. The method of claim 8, the antibody comprises a heavy chain variable region set forth in SEQ ID NO: 3 and a light chain variable region set forth in SEQ ID NO:4.

10. The method of claim 8, wherein the antibody is a full length antibody or an antigen-binding fragment thereof.

11. The method of claim 10, wherein the antibody comprises a heavy chain set forth as EVQLLESGGGLVQPGGSLRLSCAASGFTFSHYIMMWVRQAPGKGLEWVSGIYSSGGITV YADSVKGRFTISRDNSKNTLYLQMNSLRAEDTAVYYCAYRRIGVPRRDEFDIWGQGTM VTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVY TLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 11) and a light chain set forth as DIQMTQSPSTLSASVGDRVTITCRASQSISSWLAWYQQKPGKAPKLLIYKASTLESGVPSRFSGSGSGTEFTLTISSLQPDDFATYYCQQYNTYWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 12).

12. The method of claim 8, wherein the antibody is administered subcutaneously.

13. The method of claim 8, wherein the subject is a human patient having HAE, suspected of having HAE, or at risk for HAE.

14. The method of claim 8, wherein the antibody is administered for preventing HAE attack or reducing the rate of HAE attack.

15. The method of claim 8, wherein the subject has HAE type I or type II.

16. The method of claim 8, wherein:

(i) the loading period is two weeks and the antibody is administered at day 0, day 7, and day 14 and/or (ii) the maintenance period is 10 weeks and the antibody is administered at day 28, day 42, day 56, day 70, and day 84.

17. The method of claim 8, wherein the method further comprises administering to the subject the antibody at 300 mg after the maintenance period once every two to four weeks.

* * * * *